United States Patent
Yee et al.

(10) Patent No.: US 9,830,700 B2
(45) Date of Patent: Nov. 28, 2017

(54) ENHANCED COMPUTED-TOMOGRAPHY COLONOGRAPHY

(71) Applicants: Judy Yee, San Francisco, CA (US); Yu Zhang, Concord, MA (US); Sergio Aguirre-Valencia, Santa Clara, CA (US)

(72) Inventors: Judy Yee, San Francisco, CA (US); Yu Zhang, Concord, MA (US); Sergio Aguirre-Valencia, Santa Clara, CA (US)

(*) Notice: Subject to any disclaimer, the term of this patent is extended or adjusted under 35 U.S.C. 154(b) by 0 days.

(21) Appl. No.: 15/007,216

(22) Filed: Jan. 27, 2016

(65) Prior Publication Data
US 2016/0163048 A1    Jun. 9, 2016

Related U.S. Application Data

(63) Continuation-in-part of application No. 14/120,519, filed on May 28, 2014, now Pat. No. 9,384,528, and
(Continued)

(51) Int. Cl.
*G06T 15/00*    (2011.01)
*G06T 7/00*    (2017.01)
(Continued)

(52) U.S. Cl.
CPC .......... *G06T 7/0012* (2013.01); *A61B 6/032* (2013.01); *A61B 6/50* (2013.01); *G06F 3/016* (2013.01);
(Continued)

(58) Field of Classification Search
CPC .......... G06F 3/016; G06T 19/00; G06T 2207/30004; G06T 2210/41;
(Continued)

(56) References Cited

U.S. PATENT DOCUMENTS

| | | | | |
|---|---|---|---|---|
| 8,922,552 B2 * | 12/2014 | Rouet et al. | .......... | G06T 7/0083 345/419 |
| 9,361,684 B2 * | 6/2016 | Aguirre-Valencia | . | G06T 7/0028 |
| 9,384,528 B2 * | 7/2016 | Aguirre-Valencia | ..... | G06T 3/20 |

OTHER PUBLICATIONS

Li, L., Chen, D., Lakare, S., Kreeger, K., Bitter, I., Kaufman, A. E., . . . & Liang, Z. (Apr. 2002). Image segmentation approach to extract colon lumen through colonic material tagging and hidden markov random field model for virtual colonoscopy. In Medical Imaging 2002 (pp. 406-411). International Society for Optics and Photonics.*

* cited by examiner

*Primary Examiner* — Phu K Nguyen
(74) *Attorney, Agent, or Firm* — Steven Stupp

(57) ABSTRACT

A computer system that segments a colon for a computed tomography colonography (CTC) is described. During operation, the computer system accesses imaging data having a spatial resolution. Then, the computer system identifies the colon lumen based on probabilities for different tissue classes in the imaging data. Moreover, the computer system segments the colon into subsegments based on an articulated object model that fits a tortuosity of the colon along a centerline of the colon, where the articulated object model includes values of an orthonormal basis set, curvature and torsion along the centerline, and where boundaries between subsegments are based on the curvature and the torsion. For example, a given boundary between a pair of subsegments may corresponds to or may be related to a minimum value of the curvature and a maximum value of the torsion over a length of the colon.

20 Claims, 41 Drawing Sheets

Related U.S. Application Data a continuation-in-part of application No. 13/999,381, filed on Feb. 18, 2014, now Pat. No. 9,361,684.

(51) Int. Cl.
| | | |
|---|---|---|
| *A61B 6/03* | (2006.01) | |
| *A61B 6/00* | (2006.01) | |
| *G06F 3/01* | (2006.01) | |
| *G06T 19/00* | (2011.01) | |
| *G06T 7/11* | (2017.01) | |

(52) U.S. Cl.
CPC ............... *G06T 7/11* (2017.01); *G06T 19/00* (2013.01); *G06T 2207/10081* (2013.01); *G06T 2207/30004* (2013.01); *G06T 2207/30028* (2013.01); *G06T 2210/41* (2013.01); *G06T 2219/004* (2013.01)

(58) Field of Classification Search
CPC ..... G06T 2219/004; G06T 2207/30028; G06T 7/0081; G06T 2207/10081; A61B 6/032; A61B 6/50
USPC .......................................... 345/419; 382/131
See application file for complete search history.

ENHANCED COMPUTED-TOMOGRAPHY COLONOGRAPHY

CROSS REFERENCE TO RELATED APPLICATION

This application claims priority under 35 U.S.C. §120 as a Continuation-in-Part Patent Application of U.S. patent application Ser. No. 14/120,519, "Image Annotation Using a Haptic Plane," by Sergio Aguirre-Valencia, William Johnsen and Anthony Chen, filed on May 28, 2014; and as a Continuation-in-Part Patent Application of U.S. patent application Ser. No. 13/999,381, "Feature Validation Using Motion Registration," by Sergio Aguirre-Valencia, filed on Feb. 18, 2014, the contents of each of which are herein incorporated by reference.

BACKGROUND

Field

The described embodiments relate to techniques for presenting three-dimensional information associated with a computed tomography colonography (CTC).

Related Art

Many electronic devices include display subsystems that use image-rendering techniques to present visual information to users. For example, many existing display subsystems present visual information using one or more two-dimensional (2D) images (such as a 2D view of an image in a plane) that are displayed on a display.

However, it can be difficult to accurately present three-dimensional (3D) information to the users using 2D images. For example, in many computer-vision applications, a. 2D image or a sequence of 2D images (which is sometimes referred to as '2,5D' images) based on an extracted surface or a volume rendering is often used to specify a single 3D-perspective view projected on to a plane, thereby simulating the appearance of ID information. Nonetheless, the 2.5D images are not typically 3D images. In particular, the 2.5D images do not include image parallax (i.e., they do not provide stereoscopic viewing based on the offset between the left and right eyes of a viewer). Therefore, the 3D-perspective view provided by 2.5D images may not be the same as that provided by an actual 3D image. The differences that occur can result in distortions, which can degrade the accuracy of the viewer's perception of the presented. 3D information (which can result in errors) and may degrade the viewer experience by making it more difficult, time consuming and tiring for the viewer to look at the 3D information.

SUMMARY

One group of the described embodiments includes a computer system that segments a colon for a computed tomography colonography (CTC). During operation, the computer system accesses imaging data having a spatial resolution. Then, the computer system identifies a colon lumen based on probabilities for different tissue classes in the imaging data. Moreover, the computer system segments the colon into subsegments based on an object model that fits a tortuosity of the colon along a centerline of the colon, where the object model includes values, along the centerline, of one of a basis set, curvature and torsion, and a local curvature scale, and where boundaries between subsegments are based on one of: the curvature and the torsion; and the local curvature scale.

Note that the tissue classes may include: air, liquid and or a boundary between air and liquid.

Moreover, identifying the colon lumen may involve identifying, a contrast liquid residing in the colon lumen and aggregating the contrast liquid into a volume mask using a digital subtraction bowel cleaning technique.

Furthermore, the segmenting may be performed iteratively,

Additionally, the subsegments may include at least portions of a rectum, a sigmoid, a descending colon, a transverse colon, an ascending colon and or a cecum.

In some embodiments, the computer system receives navigation information specifying user navigation through the colon, and receives position information specifying a position and an orientation of a head of a user. Then, the computer system provides stereoscopic-acuity-scaled images of the subsegments of the colon with a cut plane across the colon at a pre-specified distance from the centerline based on the navigation information and the position information, where the pre-specified distance reduces an amount of rotation of a given subsegment needed to display the colon lumen. Moreover, the computer system rotates one or more of the subsegments of the colon to bring into view a clipped area of the colon lumen. Next, the computer system receives a bookmark from the user of a region in the colon that includes a potential polyp. Furthermore, the computer system may provide a two-dimensional image of the colon along, a normal direction to the bookmark, and may receive cross-sectional measurements of the potential polyp.

Note that a given boundary between a pair of subsegments may corresponds to or may be related to, over a length of the colon, of one of the curvature and the torsion, and the local curvature scale. For example, the local extremum values may include one of a minimum value of the curvature and a maximum value of the torsion and local minimum and local maximum values of the local curvature scale.

Moreover, the subsegments may be longer than a predefined first length and may be less than a predefined second length. Furthermore, there may be overlap between the subsegments. Additionally, maximum values, over a length of a given subsegment, of one of the curvature and the torsion, and the local curvature scale may be less than predefined values so that the centerline of the green subsegment is approximately linear.

A second group of the described embodiments includes a computer system that facilitates efficient navigation and/or analysis of a colon in a CTC. During operation, the computer System receives navigation information specifying user navigation through the colon, and receives position information specifying a position and an orientation of a head of a user. Then, the computer system provides stereoscopic-acuity-scaled images of subsegments of the colon with a cut plane across the colon at a pre-specified distance from a centerline of the colon based on the navigation information and the position information, where the pre-specified distance reduces an amount of rotation of a given subsegment needed to display the colon lumen. Moreover, the computer system rotates one or more of the subsegments of the colon to bring into view a clipped area of the colon lumen. Next, the computer system receives a bookmark from the user of a region in the colon that includes a potential polyp. Furthermore, the computer system may provide a two-dimensional image of the colon along a normal direction to the bookmark, and may receive cross-sectional measurements of the potential polyp.

Another embodiment provides a computer-program product for use with the computer system. This computer-program product includes instructions for at least some of the operations performed by the computer system, Another embodiment provides a method, which may be performed by the computer system. During the method, the computer system may perform at least sonic of the operations described above.

The preceding summary is provided as an overview of some exemplary embodiments and to provide a basic understanding, of aspects of the subject matter described herein. Accordingly, the above-described features are merely examples and should not be construed as narrowing the scope or spirit of the subject matter described herein in any way. Other features, aspects, and advantages of the subject matter described herein will become apparent from the following Detailed Description, Figures, and Claims.

Table 1 provides pseudo-code for a segmentation calculation at the interface between tissue classes in accordance with an embodiment of the present disclosure.

Table 2 provides a representation of a problem-solving virtual instrument in accordance with an embodiment of the present disclosure.

Table 3 provides pseudo-code for a segmentation calculation at the interface between tissue classes in CTC in accordance with an embodiment of the present disclosure.

Figure 25:
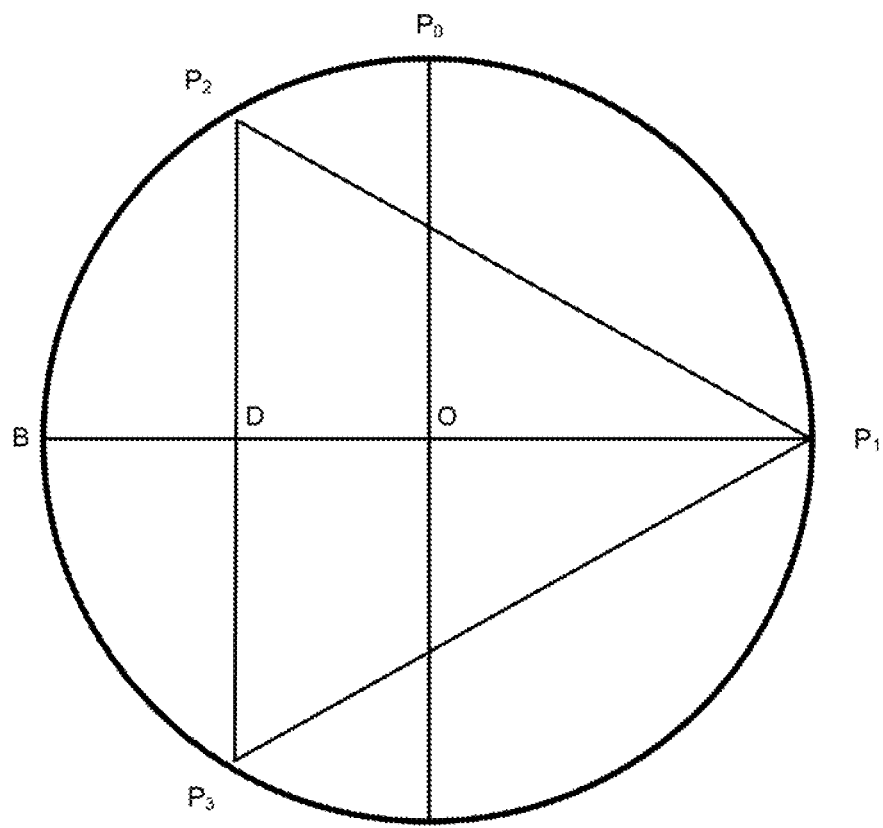
FIG. 25 is a drawing illustrating cut-plane placement in accordance with an embodiment of the present disclosure.

Table 4 provides values of the pre-specified distance from the centerline (D) in different segments of the colon using the geometry of FIG. 25 in accordance with an embodiment of the present disclosure.

Note that like reference numerals refer to corresponding pans throughout the drawings. Moreover, multiple instances of the same part are designated by a common prefix separated from an instance number by a dash.

DETAILED DESCRIPTION

Human perception of information about the surrounding environment contained in visible light (which is sometimes referred to as 'eyesight,' 'sight', or 'vision') is facilitated by multiple physiological components in the human visual system, including senses that provide sensory inputs and the cognitive interpretation of the sensory inputs by the brain. The graphical system in the present application provides rendered images that intuitively facilitate accurate human perception of 3-dimensional (3D) visual information (i.e., the awareness of an object or a scene through physical sensation of the 3D visual information). In particular, the graphical system in the present application provides so-called. True 3D via rendered left-eye and right-eye images that include apparent image parallax (Le., a difference in the position of the object or the scene depicted in the rendered left-eye and the right-eye images that approximates the difference that would occur if the object or the scene were viewed along two different lines of sight associated with the positions of the left and right eyes). This apparent image parallax may provide depth acuity (the ability to resolve depth in detail) and thereby triggers realistic stereopsis in an individual (who is sometimes referred to as a 'user,' a 'viewer' or an 'observer' i.e., the sense of depth (and, more generally, actual 3D information) that is perceived by the individual because of retinal disparity or the difference in the left and right retinal images that occur when the object or the scene is viewed with both eyes or stereoscopically (as opposed to viewing, with one eye or monoscopically).

The True 3D provided by the graphical system may incorporate a variety of additional features to enhance or maximize the depth acuity. In particular, the depth acuity may be enhanced by scaling the objects depicted in left-eye and the right-eye images prior to rendering based on the spatial resolution of the presented 3D visual information and the viewing geometry. Moreover, the graphical system may include motion parallax (the apparent relative motion of a stationary object against a background when the individual moves in a sequence of rendered left-eye and right-eye images so that the displayed visual information is modified based on changes in the position of the individual. This capability may be facilitated by a sensor input to the graphical system that determines or indicates the motion of the individual while the individual views the rendered left-eye and the right-eye images. Furthermore, the sequence of rendered left-eye and right-eye images may include prehension, which, in this context, is the perception by the individual of taking hold, seizing, grasping or, more generally, interacting with the object. This capability may be facilitated by another sensor input to the graphical system that monitors interaction between the individual and the displayed visual information. For example, the individual may interact with the object using a stylus. In addition, the depth acuity offered by the graphical system may be enhanced through the use of monoscopic depth cues, such as: relative sizes/positions for geometric perspective), lighting, shading, occlusion, textural gradients, and/or depth cueing.

In a wide variety of applications, True 3D may allow the individual to combine cognition (i.e., a deliberative conscious mental process by which one achieves knowledge) and intuition (i,e., an unconscious mental process by which one acquires knowledge without inference or deliberative thought). This synergistic combination may limber increase the individual's knowledge allow them to use the graphical system to perform tasks more accurately and more efficiently. For example, this capability may allow a physician to synthesize the emotional function of the right brain with the analytical functions of the left brain to interpret the True 3D images as a more accurate and acceptable approximation of reality. In radiology, this may improve diagnoses or efficacy, and may increase the confidence of radiologists when making decisions. As a consequence, True 3D may allow radiologists to increase their throughput or workflow (e.g., the enhanced depth acuity may result in improved sensitivity to smaller features, thereby reducing, the time needed to accurately resolve features in the rendered images). Alternatively, surgeons can use this capability to plan surgeries or to perform virtual surgeries (for example, to rehearse a surgery) which may otherwise be impossible using existing graphical systems. Furthermore, because the visual information in True 3D intuitively facilitates accurate human perception, it may be easier and less tiring for physicians to view the images provided by the graphical system than those provided by existing graphical systems. Collectively, these features may improve patient outcomes and may reduce the cost of providing medical care.

Figure 1:
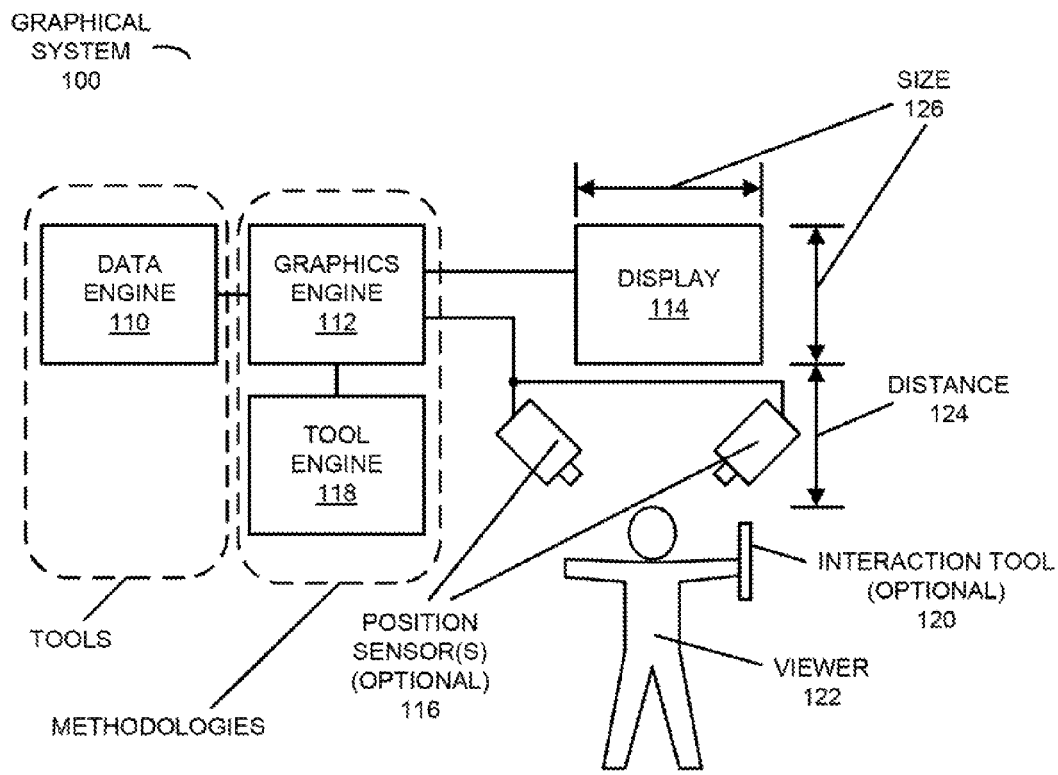
FIG. 1 is a block diagram illustrating, a graphical system in accordance with an embodiment of the present disclosure.

While the embodiments of True 3D may not result in perfect perception of the 3D visual information by all viewers tin principle, this may require additional sensory inputs, such as those related to balance), in general the deviations that occur may not be detected by most viewers. Thus, the graphical system may render images based on a volumetric virtual space that very closely approximates what the individual would see with their own visual system. As described further below in the discussion of applications of the graphical system, the deviations that do occur in the perception of the rendered images may be defined based on a given application, such as how accurately radiologists are able to detect the presence of cancer based on the images provided by the graphical system, Graphical System FIG. 1 presents a block diagram of a graphical system 100, including a data engine 110, graphics (or rendering) engine 112, display 114, one or more optional position sensor(s) 116, and tool engine 118. This graphical system may facilitate close-range stereoscopic viewing, of 3D objects (such as those depicting human anatomy) with unrestricted head motion and hand-directed interaction with the 3D objects, thereby providing a rich holographic experience.

During operation, data engine 110 may receive input data (such as a computed-tomography or CT scan, histology, an ultrasound image, a magnetic resonance imaging or MRI scan, or another type of 2D image slice depicting volumetric information), including dimensions and spatial resolution. In an exemplary embodiment, the input data may include representations of human anatomy, such as input data that is compatible with a Digital Imaging and Communications in Medicine (DICOM) standard. However, a wide variety of types of input data may be used (including non-medical data), which may be obtained using different imaging techniques, different wavelengths of light (microwave, infrared, optical, x-ray), etc.

After receiving the input data, data engine 110 may: define segments in the data (such as labeling tissue versus air); other parameters (such as transfer functions for voxels): identify landmarks or reference objects in the data (such as anatomical features); and identify 3D objects in the data (such as the colon and, more generally, groups of voxels). One or more of these operations may be performed by or may be augmented based on input from a user or viewer 122 of graphical system 100.

As described further below, based on the information output by data engine 110 (including the left and right eye coordinates and distance 124 of viewer 122 from display 114), graphics engine 112 may define, for the identified 3D objects, model matrices (which specify where the objects are in space relative to viewer 122 using a model for each of the objects), view matrices (which specify, relative to a tracking camera in display 114, the location and/or gaze direction of the eyes of viewer 122), and projection or frustum matrices (which specify what is visible to the eves of viewer 122). These model, view and frustum matrices may be used by graphics engine 112 to render images of the 3D objects. For a given eye, the rendered image may provide a 2.5D monoscopic projection view on display 114. By sequentially displaying left-eye and right-eye images that include image parallax (i.e., stereoscopic images), 3D information may be presented on display 114. These images may be appropriately scaled or sized so that the images match the physical parameters of the viewing geometry (including the position of viewer 122 and size 126 of the display 114). This may facilitate the holographic effect for viewer 122. In addition, the left-eye and the right-eye images may be displayed at a monoscopic frequency of at least 90 Hz (or a stereoscopic frequency of at least 45 Hz), which can be viewed by viewer 122 using polarized glasses. Note that this frequency ma be large enough to avoid flicker even in ambient lighting and may he sufficient for viewer 122 to fuse the images to perceive stereopsis and motion.

Moreover, one or more optional position sensors 116 (which may be separate from or integrated into display 114) may dynamically track movement of the head of viewer 122 with up to six degrees of freedom, and this head-tracking information (e,g, the positions of the eyes of viewer 122 relative to display 114) may be used by graphics engine 112 to update the view and frustum matrices and, thus, the rendered left-eye and right-eye images. In this way, the rendered images may be optimal from the viewer perspective and may include motion parallax. In some embodiments, the one or more optional position sensor(s) 116 optionally dynamically track the gaze direction of viewer 122 (such as where viewer 122 is looking). By tracking where viewer 122 is looking, graphics engine 112 may include foveated imaging when rendering images, which can provide additional depth perception. For example, the transfer functions defined by data engine 110 may be used to modify the rendering of voxels in a 3D image (such as the transparency of the voxels) based on the focal plane of viewer 122, Furthermore, tool engine 118 may dynamically track 3D interaction of viewer 122 with an optional physical interaction tool 120 (such as a stylus a mouse or a touch pad that viewer 122 uses to interact with one or mote of the displayed 3D objects) with up to six degrees of freedom. For example, viewer 122 can grasp an object and interact with it using optional interaction tool 120. The detected interaction information provided by tool engine 118 may be used by graphics engine 112 to update the view and frustum matrices and, thus, the rendered left-eye and right-eye images. In this way, the rendered images may update the perspective based on interaction of viewer 122 with one or more of the displayed 3D objects using the interaction tool (and, thus, may provide prehension), which may facilitate hand-eye coordination of viewer 122.

By using image parallax, motion parallax and prehension, graphical system 100 may provide cues that the human brain uses to understand the 31) world. In particular, the image parallax triggers stereopsis, while the motion parallax can enable the viewer to fuse stereoscopic images with greater depth. In addition, the kinesthetic (sensory) input associated with the prehension in conjunction with the stereopsis may provide an intuitive feedback loop between the mind, eves and hand of viewer 122 (i.e., the rich holographic experience).

Note that the one or more optional position sensors 116 may use a wide variety of techniques to track the locations of the eyes of viewer 122 and/or where viewer 122 is looking (such as a general direction relative to display 114). For example, viewer 122 may be provided glasses with reflecting surfaces (such as five reflecting surfaces), and infrared light reflected off of these surfaces may be captured by cameras or imaging sensors (Which may be integrated into or included in display 114). This may allow the 3D coordinates of the reflecting surfaces to be determined. In turn, these 3D coordinates may specify the location and/or the viewing direction of the eyes of viewer 122, and can be used to track head movement Alternatively or additionally, stereoscopic triangulation may be used, such as Leap (from Leap Motion, Inc, of San Francisco, Calif.). For example, two (left/right) camera views of the face of viewer 122 may be used to estimate what viewer 122 is looking at. In particular, image processing of the two camera views may allow the 3D coordinates of the eyes of viewer 122 to be determined. Another technique for tracking head motion may include sensors (such as magnetic sensors) in the glasses that allow the position of the glasses to be tracked. More generally, a gyroscope, electromagnetic tracking (such as that offered by Northern Digital, inc. of Ontario. Canada), a local positioning system and/or a time of flight technique may be used to track the head position of viewer 122, such as Kinect (front Microsoft Corporation of Redmond, Wash.). In the discussion that follows, cameras in display 114 are used as an illustrative example of a technique for tracking the location and/or gaze direction of the eyes of viewer 122.

Furthermore, instead of optional physical interaction tool 120, in some embodiments viewer 122 may interact with displayed objects by using gestures in space (such as by moving one or more fingers on one or more of their hands). For example, a time of flight technique may be used (such as Kinect) and/or stereoscopic triangulation may be used (such as Leap). More generally, the position or motion of optional physical interaction tool 120 may be determined: optically, using magnetic sensors, using electromagnetic tracking, using a gyroscope, using stereoscopic triangulation and/or using a local positioning system.

Note that optional physical interaction tool 120 may provide improved spatial control for viewer 122 (such as a surgeon) when interacting with the displayed objects.

Additionally, a wide variety of displays and display technologies may be used for display 114 In an exemplary embodiment, display 114 integrates the one or more optional position sensors 116. For example, display 114 may be provided by Infinite Z. Inc. (of Mountain View, Calif.) or Leonar3do International, Inc, (of Herceghalom, Hungary). Display 114 may include: a cathode ray tube, a liquid crystal display, a plasma display, a projection display, a holographic display, an organic light-emitting-diode display, an electronic paper display, a ferroelectric liquid display, a flexible display, a head-mounted display, a retinal scan display, and/or another type of display. In an exemplary embodiment, display 114 is a 2D display. However, in embodiments where display includes a holographic display, instead of sequentially (and alternately) displaying left-eye and right-eye images, at a given time a given pair of images (left-eye and right-eye) may concurrently displayed by display 114 or the information in the given pair of images may be concurrently displayed by display 114. Thus, display 114 may be able to display magnitude and/or phase information, Image Processing and Rendering Operations Graphics engine 112 may implement a vertex-graphics-rendering process in which 3D vertices define the corners or intersections of voxels and, more generally, geometric shapes in the input data. In an exemplary embodiment, graphics engine 112 uses a right-handed coordinate system. Graphics engine 112 may use physical inputs (such as the position of the eyes of viewer 122) and predefined parameters (such as those describing size 126 of display 114 in FIG. 1 and the viewing geometry) to define the virtual space based on matrices. Not that graphics engine, 112 'returns' to the physical space when the left-eye and right-eye images are rendered based on the matrices in the virtual space.

In the virtual space, 3D objects may each be represented by a 4×4 matrix with an origin position, a scale and an orientation. These objects may depict images, 30 volumes, 3D surfaces, meshes, lines or points in the input data. For computational simplicity, all the vertices may he treated as three-dimensional homogeneous vertices that include four coordinates, three geometric coordinates (x, y, and z) and a scale w. These four coordinates may define a 4×1 column vector (x, y, z, w)$^T$. Not that if w equals one then the vector (x, y, z, 1) is a position in space; if w equals zero, then the vector (x, y, z, 0) is a position in a direction; and if w is greater than zero, then the homogeneous vertex (x, y, z, w)$^T$ corresponds to the 3D point (x/w, y/w, z/w)$^T$.

Using homogeneous coordinates, a vertex array can represent a 3D object. In particular, an object matrix At may initially be represented as $$\begin{bmatrix} m0 & m4 & m8 & m12 \\ m1 & m5 & m9 & m13 \\ m2 & m6 & m10 & m14 \\ m3 & m7 & m11 & m15 \end{bmatrix},$$

where, by default, (m0, m1, m2) may be the x axis (left) vector (1, 0, 0), (m4, m5, m6) may be the +y axis (up) vector (0, 1, 0), (m8, m9, m10) may be the +z axis (forward) vector (0, 0, 1), m3, m7, and m11 may define the relative scale of these vectors along these axes, m12, m13, m14 specify the position of a camera that tracks the positions of the eyes of viewer 122, and m15 may be one.

By applying a rotation operation (R), a translation operation (T) and a scaling operation (S) across the vertex array of an object (i.e., to all of its (x, y, z, w) vectors), the object can be modified in the virtual space. For example, these operations may be used to change the position of the object based on where viewer 122 is looking, and to modify the dimensions or scale of the object so that the size and proportions of the object are accurate. In particular, a transformed vector may be determined using $$S \cdot R \cdot T \cdot I_0,$$

where $I_0$ is an initial vector in the virtual space. Note that, in a right-handed coordinate system, a rotation a about the x axis (Rx), a rotation a about the y axis (Ry) and a rotation a about the z axis (Rz), can be represented as $$Rx = \begin{bmatrix} 1 & 0 & 0 & 0 \\ 0 & \cos(a) & -\sin(a) & 0 \\ 0 & \sin(a) & \cos(a) & 0 \\ 0 & 0 & 0 & 1 \end{bmatrix},$$

$$Ry = \begin{bmatrix} \cos(a) & 0 & \sin(a) & 0 \\ 0 & 1 & 0 & 0 \\ -\sin(a) & 0 & \cos(a) & 0 \\ 0 & 0 & 0 & 1 \end{bmatrix} \text{ and}$$

$$Rz = \begin{bmatrix} \cos(a) & -\sin(a) & 0 & 0 \\ \sin(a) & \cos(a) & 0 & 0 \\ 0 & 0 & 1 & 0 \\ 0 & 0 & 0 & 1 \end{bmatrix}.$$

Similarly, a translation by (x,y,z) can be represented as $$T = \begin{bmatrix} 1 & 0 & 0 & x \\ 0 & 1 & 0 & y \\ 0 & 0 & 1 & z \\ 0 & 0 & 0 & 1 \end{bmatrix},$$

a non-uniform sealing by $s_x$ along the x axis, $s_y$ along the y axis and $s_z$ along the z axis can be represented as $$S = \begin{bmatrix} s_x & 0 & 0 & 0 \\ 0 & s_y & 0 & 0 \\ 0 & 0 & s_z & 0 \\ 0 & 0 & 0 & 1 \end{bmatrix}$$

and a uniform scaling s can be represented as $$S = \begin{bmatrix} 1 & 0 & 0 & 0 \\ 0 & 1 & 0 & 0 \\ 0 & 0 & 1 & 0 \\ 0 & 0 & 0 & s \end{bmatrix}.$$

Moreover, note that an arbitrary combination of rotation, translation and scaling matrices is sometimes referred to as a 'transformation matrix' Tf. Therefore, after applying the rotation, translation and scaling matrices, the model matrix M may become a model transformation matrix Mt. This transformation matrix may include the position of the object $(tx, ty, tz, 1)^T$, the scale s of the object and/or the direction R of the object $[(r1, r2, r3,)^T, (r4, r5, r6)^T, (r7, r8, r9)^T]$. Thus, the transformation matrix Mt may be generated by: translating the object to its origin position $(tx, ty, tz, 1)^T$; rotating the object by R; and/or scaling the object by s. For example, with uniform scaling the transformation matrix Mt may be represented as $$\begin{bmatrix} r1 & r4 & r7 & tx \\ r2 & r5 & r8 & ty \\ r3 & r6 & r9 & tz \\ 0 & 0 & 0 & s \end{bmatrix}.$$

In addition to the model matrices for the objects, graphics engine 112 may also implement so-called 'views' and 'perspective projections,' which may each be represented using homogeneous 4×4 matrices. The view may specify the position and/or viewing target (or gaze direction) of viewer 122 (and, thus, may specify where the objects are in space relative to viewer 122). In the virtual space, a given view matrix V (for the left eye or the right eye) may be based on the position of a camera that tracks the positions of the eyes of viewer 122, the location the camera is targeting, and the direction of the unit vectors (i.e, which way is up), for example, using a right-hand coordinate system. In the physical space, the view matrices V may be further based on the eye positions of viewer 122, the direction of the unit vectors and/or where viewer 122 is looking. In an exemplary embodiment, the view matrices V are created by specifying the position of the camera and the eyes of viewer 122, specifying the target coordinate of the camera and the target coordinate of the eyes of viewer 122, and a vector specifying the normalized +y axis (which may be the 'up' direction in a right-handed coordinate system). For example, the target coordinate may be the location that the camera (or the eyes of viewer 122) is pointed, such as the center of display 114.

In an exemplary embodiment, the given view matrix V is determined by constructing a rotation matrix Rv. In this rotation matrix, the 'z axis' may be defined as the normal from given camera position $(px, py, pz)^T$ minus the target position, i.e.

$(z1,z2,z3)^T=\text{normal}[(px,py,pz)^T-(tx,ty,tz)^T].$

Then, the 'x axis' may be calculated as the normal of the cross product of the 'z axis' and normalized +y axis (which may represent the 'up' direction). i.e., $(x1,x2,x3)^T=\text{normal}[\text{crosses}[(z1,z2,z3)^T-(ux,uy,uz)^T]].$ Moreover, the un-normalized y axis may be calculated as the cross product of the 'z axis' and 'x axis,' i.e., $(y1,y2,y3)^T=\text{normal}[(z1z,z2,z3)^T, (x1,x2,x3)^T].$ Thus, the complete 4×4 rotation matrix Rv for use in determining the given view matrix may be $$\begin{bmatrix} x1 & y1 & z1 & 0 \\ x2 & y2 & z2 & 0 \\ x3 & y3 & z3 & 0 \\ 0 & 0 & 0 & 1 \end{bmatrix}.$$

Next, the given view matrix V may also be determined by constructing a translation matrix Tv based on the position of one of the eyes of viewer 122 (tx, ty, tz). In particular, the translation matrix Tv may he represented as $$Tv = \begin{bmatrix} 1 & 0 & 0 & tx \\ 0 & 1 & 0 & ty \\ 0 & 0 & 1 & tz \\ 0 & 0 & 0 & 1 \end{bmatrix}.$$

Using the rotation matrix Rv and the translation matrix Tv, the inverse of the given view matrix $V^{-1}$ may be determined as $V^{-1} = Rv \cdot Tv$ or $$V^{-1} = \begin{bmatrix} x1 & y1 & z1 & tx \\ x2 & y2 & z2 & ty \\ x3 & y3 & z3 & tz \\ 0 & 0 & 0 & 1 \end{bmatrix}.$$

The perspective projection may use left-eye and right-eye frustums F to define how the view volume is projected on to a 2-dimensional (2D) plane (e.g., the viewing plane, such as display 114) and on to the eyes of viewer 122 (which may specify what is visible to the eyes of viewer 122). In the virtual space, a given frustum (for the left eye or the right eye) may he the portion of the 3D space (and the 3D) objects it contains) that may appear or be projected as 2D left-eye or right-eye images on display 114. In the physical space, the given frustum may he the viewing volume that defines how the 3D objects are projected on to one of the eyes of viewer 122 to produce retinal images of the 3D objects that will be perceived (i.e., the given frustum specifies what one of the eyes of viewer 122 sees or observes when viewing display 114). Note that the perspective projection may project all points into a single point (an eye of viewer 122). As a consequence, the two perspective projections, one for the left eye of the viewer and another for the right eye of the viewer, are respectively used by graphics engine 112 when determining the left-eye image and the right-eye image. In general, for an arbitrary head position of viewer 122, the projection matrices or frustums for the left eye and the right eye are different from each other and are asymmetric.

Figure 2:
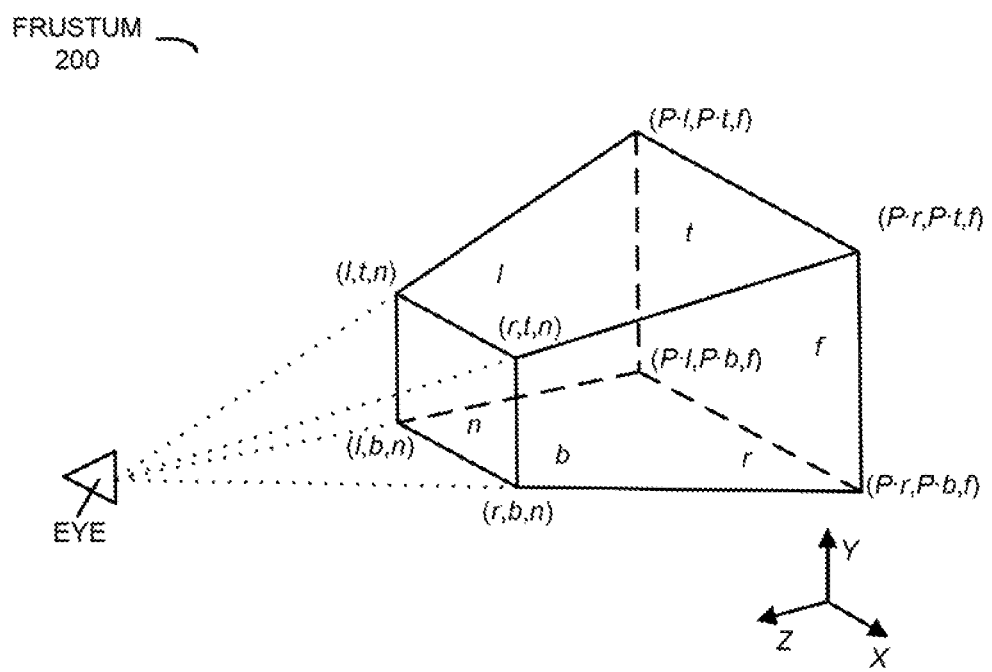
FIG. 2 is a drawing illustrating a frustum for a vertical display in the graphical system of FIG. 1 in accordance with an embodiment of the present disclosure.

FIG. 2 presents a drawing illustrating a frustum 200 for a vertical display in graphical system 100. This frustum includes a near plane for surface), a far (or back) plane, a left plane, a right plane, a top plane and a bottom plane. In this example, the near plane is defined at equal to n. Moreover, the vertices of the near plane are at x equal to l and r (for, respectively, the left and right planes) and y equal to l and b (for, respectively, the top and bottom planes). The vertices of the far f plane can be calculated based on the ratio of similar triangles as $$\frac{f}{n} = \frac{left_{far}}{l} = \frac{l_{far}}{l},$$

which can be re-arranged as $$l_{far} = \left(\frac{f}{n}\right) \cdot l.$$

By defining a perspective projection factor P as $$\frac{f}{n}$$

this can be re-expressed as $$l_{far} = P \cdot l$$

As shown in FIG. 2, the coordinates of the vertices at the fax plane in frustum 200 can be expressed in terms of the coordinates at the near plane and the perspective projection factor P. Moreover, frustum (F) 200 can be expressed as a 4×4 matrix $$F = \begin{bmatrix} \frac{2n}{r-l} & 0 & \frac{r+l}{r-l} & 0 \\ 0 & \frac{2n}{t-b} & \frac{t+b}{t-b} & 0 \\ 0 & 0 & \frac{-(f+n)}{f-n} & \frac{-2fn}{f-n} \\ 0 & 0 & -1 & 0 \end{bmatrix}.$$

In an exemplary embodiment, when the head position of viewer 122 in FIG. 1 is not tracked (i.e., when motion parallax is not included), the near plane may be coincident with display 114 in FIG. 1. (In the discussion that follows, the plane of display 114 in FIG. 1 is sometimes referred to as the 'viewing plane.') in this case, frustum 200 extends behind the plane of display 114 (FIG. 1). Because viewer perception of stereopsis is high between 15 and 65 cm, and eventually decays at larger distances away from viewer 122 (FIG. 1), the fir plane may define a practical limit to the number of vertices that are computed by graphics engine 112 (FIG. 1). For example, f may be twice n. In addition, as described further below, by defining a finite space, the left-eye and right-eye images may be scaled to enhance or maximize the depth acuity resolved by viewer 122 (FIG. 1) for a given spatial resolution in the input data and the viewing geometry in graphical system 100 in FIG. 1 (which is sometimes referred to as 'stereopsis scaling' or 'stereo-acuity scaling').

Figure 3:
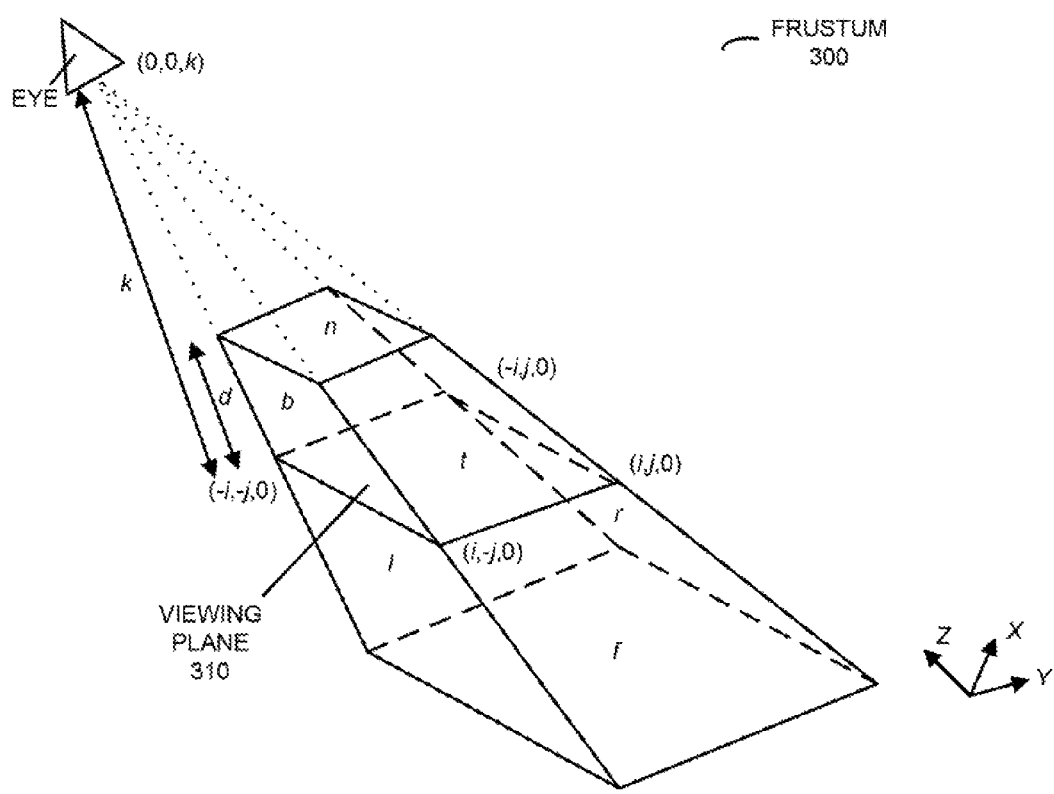
FIG. 3 is a drawing illustrating a frustum for a horizontal display in the graphical system of FIG. 1 in accordance with an embodiment of the present disclosure.
Figure 4:
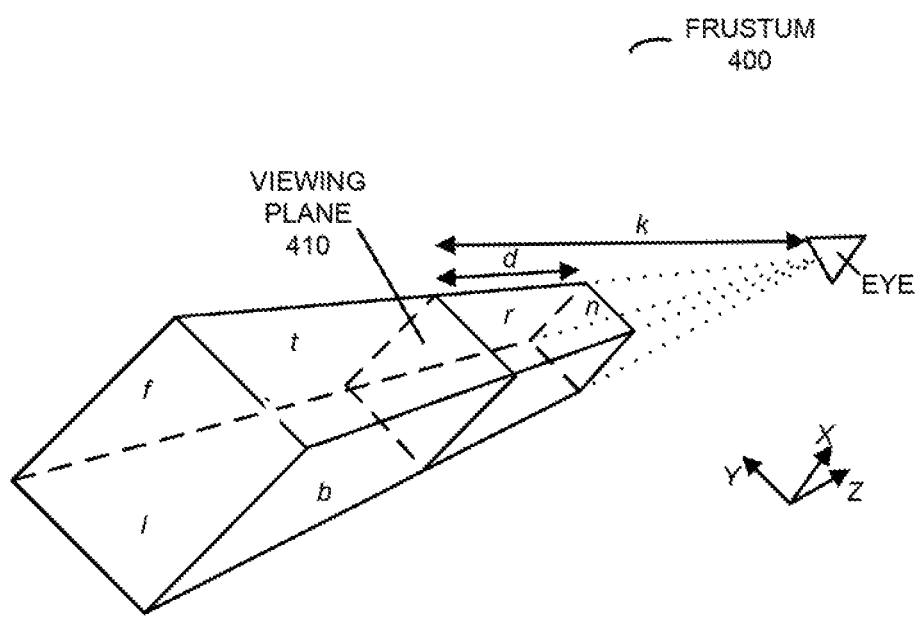
FIG. 4 is a drawing illustrating a frustum for an inclined display in the graphical system of FIG. 1 in accordance with an embodiment of the present disclosure.

While the preceding example of the frustum used a vertical display, in other embodiments display 114 (FIG. 1) may be horizontal or may be at an incline. For example, in surgical applications, display 114 (FIG. 1) may be placed on the floor. As shown in FIGS. 3 and 4, which present drawings illustrating frustums 300 (FIG. 3) and 400, in these configurations the frustums are rotated.

When the position of the head or the eyes of viewer 122 (FIG. 1) are tracked in graphical system 100 in FIG. 1 (so that the rendered left-eye and right-eye images can be modified accordingly), the viewing plane may be placed approximately in the middle of the frustums to provide back-and-forth spatial margin. This is illustrated by viewing planes 310 (FIG. 3) and 410. Moreover, as shown in FIG. 3, the coordinates of the vertices of viewing plane 310 may be left (−i), right (+i), top (+j), bottom (−j), and the z (depth) coordinate may be zero so that the near plane is at z coordinate d and the eyes of viewer 122 (FIG. 1) are at z coordinate k. (In some embodiments, the near plane is defined at the same z coordinate as the eyes of viewer 122 in FIG. 1.) Based on these coordinates, the far-plane coordinates can be determined using, the perspective projection factor P.

Note that, while the preceding example defined the frustum based on the distance z from viewer 122 (FIG. 1) to display 114 (FIG. 1), in embodiments where the one or more optional position sensors 116 (FIG. 1) track the gaze direction of viewer 122 (FIG. 1), the frustum may be based on the focal point of viewer (FIG. 1). Furthermore, while a viewing plane was used as a reference in the preceding discussion, in some embodiments multiple local planes (such as a set of tiled planes) at different distances z from viewer 122 (FIG. 1) to display 114 (FIG. 1) are used.

By multiplying the left-eye or right-eye) frustum F by the corresponding left-eye (or fight-eye) view matrix V and the model transformation matrix Mt, a 2D projection in the viewing plane of a 3D object an be determined for rendering as a given left-eye (or right-eye) image. These operations may be repeated for the other image to provide stereoscopic viewing. As described further below with reference to FIG. 6, note that when rendering these 2D projections, a surface may be extracted for a collection of voxels or a volume rending may be made based on ray tracing.

In order to enhance or maximize the depth acuity resolved by viewer 122 in FIG. 1 (and, thus, to provide high-resolution depth perception), the graphics engine 112 (FIG. 1) may ensure that the geometric disparity between the left-eye and the right-eye images remains between a minimum value that viewer 122 (FIG. 1) can perceive (which is computed below) and a maximum value (beyond which the human mind merges the left-eye and the right-eye images and stereopsis is not perceived). In principle, graphics engine 112 (FIG. 1) may scale the objects in the image(s) presented to viewer 122 (FIG. 1) in proportion to their focal distance z (which is sometimes referred to as a 'geometric perspective'), or may have free control of the focal distance of viewer 122 (FIG. 1) in order to accommodate all the objects viewer 122 (FIG. 1) wants to observe. The latter option is what happens in the real world. For example, when an individual focuses on a desk and, thus, has accommodated to a short focal distance, he or she can resolve depth with a precision of around 1 mm. However, when the individual is outside and accommodates to a longer focal distance, he or she can resolve depth with a precision of around 8 cm.

In practice, because graphical system 100 (FIG. 1) implements stereoscopic viewing (which provides depth information), it is not necessary to implement geometric, perspective (although, in some embodiments, geometric perspective is used in graphical system 100 in FIG. 1 addition to image parallax). Instead, in graphical system 100 (FIG. 1) objects may be scaled in proportion to the distance z of viewer 122 (FIG. 1) from display 114 (FIG. 1). As described previously, a range of distances z may occur and, based on the head-tracking information, this range may be used to create the frustum. In particular, after determining the 2D projection, graphics engine 112 (FIG. 1) may scale a given object in the image(s) presented to the viewer based on based on the viewing geometry (including the distance z) and a given spatial resolution in the input data (such as the voxel spacing, the discrete spacing between image slices, and/or, more generally, the discrete spatial sampling in the input data) in order to enhance (and, ideally, to maximize or optimize) the depth acuity. This stereopsis scaling may allow viewer 122 (FIG. 1) to perceive depth information in the left-eye and the right-eye images more readily, and in less time and with less effort (or eye strain) for discretely sampled data. As such, the stereopsis scaling may significantly improve the viewer experience and may improve the ability of viewer 122 (FIG. 1) to perceive 3D information when viewing the left-eye and the right-eye images provided by graphical system 100 (FIG. 1).

Note that the stereopsis scaling may not be typically performed in computer-aided design systems because these approaches are often model-based which allows the resulting images to readily incorporate geometric perspective for an arbitrary-sized display. In addition, stereopsis scaling is typically not performed in 2.5D graphical systems because these approaches often include markers having a predefined size in the resulting images as comparative references.

Figure 5:
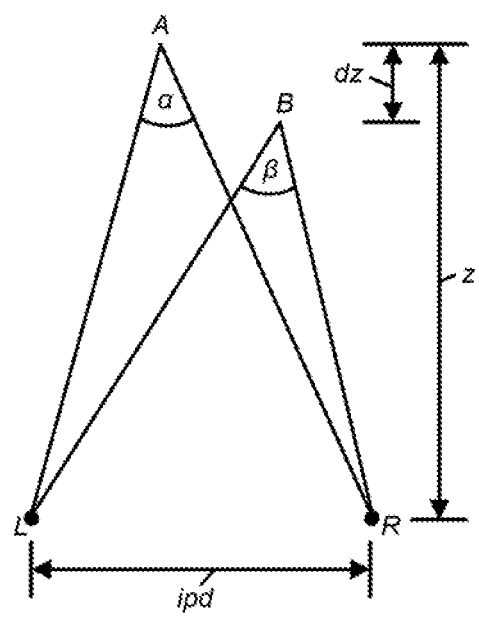
FIG. 5 is a drawing illustrating calculation of stereopsis scaling in the graphical system of FIG. 1 in accordance with an embodiment of the present disclosure.

FIG. 5 presents a drawing illustrating the calculation of the stereopsis scaling for a given spatial resolution m the input data and a given viewing geometry. In this drawing, ipd is interpupillary distance, z is the distance to the focal point of viewer 122 (FIG. 1) (which, as noted previously, may be replaced by the distance between viewer 122 and display 114 in FIG. 1 in embodiments where the head position of viewer 122 is tracked), dz is the delta in the z (depth) position of an object to the focal point, L is the left eye-position and R is the right-eye position. Moreover, the geometric disparity δγ may be defined based on the difference in the angles α and β times L, i.e., $$\delta\gamma = L \cdot (\alpha - \beta).$$

This can be re-expressed as $$\delta\gamma = \frac{(ipd) \cdot (dz)}{z^2 + z \cdot (dz)}.$$

If z is 400 mm, the ipd is 65 mm (on average) and dz is 1 mm, the geometric disparity δγ equals $4.052 \times 10^{-4}$ radians or 82.506 arcseconds. As noted previously, viewers have minimum and maximum values of the geometric disparity δγ that they can perceive. For a given distance z (which, as noted previously, may be determined by tracking the head position of viewer 122 in FIG. 1), the scale of the objects in the left-eye image and the right-eye image can be selected to enhance or maximize the depth acuity based on $$dz = \frac{\delta\gamma \cdot (z^2)}{ipd}, \quad (1)$$

which defines the minimum dz needed for stereopsis. For example, in the case of medical images, dz may be the voxel spacing. (Note that, for an x spacing dx, a y spacing dy and a z spacing dz, the voxel size dv may be defined as $$dv^2 = dx^2 + dy^2 + dz^2.)$$

Moreover, the minimum value of the geometric disparity δγ (which triggers stereopsis and defines the depth acuity) may be 2-10 arcseconds (which, for 10 arcseconds, is $4.486 \times 10^{-5}$ radians) and the maximum value may be 600 arcseconds (which, for 100 arcseconds, is $4.486 \times 10^{-4}$ radians). If the average distance: from the viewer to display 114 (FIG. 1) is 0.5 m an extremum of the 0.5-1.5 m range over which the depth acuity is a linear function of distance z), the ipd equals 65 mm and the minimum value of the geometric disparity δγ is 10 arcseconds, the minimum $dz_{min}$ in Eqn. 1 to maintain optimal depth acuity is 0.186 mm. Similarly, if the average distance z is 0.5 m, the ipd equals 65 mm and the maximum value of the geometric disparity δγ is 100 arcseconds, the maximum $dz_{max}$ in Eqn. 1 to maintain optimal depth acuity is 1.86 mm. Defining the minimum scale $s_{mm}$ as $$s_{min} = \frac{dz_{min}}{dv}$$

and the maximum scale $s_{max}$ as $$s_{max} = \frac{dz_{max}}{dv},$$

and for an isometric 1 mm voxel resolution, the minimum scale $s_{min}$ is 0.186 and the maximum scale $s_{max}$ is 1.86. Therefore, in this example the objects in left-eye and the right-eye images can be scaled by a factor between 0.186 and 1.86 (depending on the average tracked distance z) to optimize the depth acuity. Note that, in embodiments here the one or more optional position sensors 116 (FIG. 1) track the gaze direction of viewer 122 (FIG. 1), the stereopsis scaling may be varied based on the focal point of viewer 122 (FIG. 1 instead of the distance z from viewer 122 (FIG. 1) to display 114 (FIG. 1).

While the preceding example illustrated the stereopsis scaling based on an average δγ and an average ipd, in some embodiments the stereopsis scaling is based on an individual's δγ and/or ipd. For example, viewer 122 (FIG. 1) may provide either or both of these values to graphical system 100 (FIG. 1), Alternatively graphical system 100 (FIG. 1) may measure the δγ and/or the ipd of viewer 122 (FIG. I).

Graphical system 100 (FIG. 1) may also implement monoscopic depth cues in the rendered left-eye and right-eye images. These monoscopic depth cues may provide a priori depth information based on the experience of viewer 122 (FIG. 1). Note that the monoscopic depth cues may complement the effect of image parallax and motion parallax in triggering stereopsis. In particular, the monoscopic depth cues may include: relative sizes/positions (or geometric perspective), lighting, shading, occlusion, textural gradients, and/or depth cueing.

As noted previously, a geometric-perspective monoscopic depth cue (which is sometimes referred to as a 'rectilinear perspective' or a 'photographic perspective') may be based on the experience of viewer 122 (FIG. 1) that the size of the image of an object projected by the lens of the eye onto the retina is larger when the object is closer and is smaller when the object is further away. This reduced visibility of distant object (for example, by expanding outward from a focal point, which is related to the frustum) may define the relationship between foreground and background objects. If the geometric perspective is exaggerated, or if there are perspective cues such as lines receding to a vanishing point, the apparent depth of an image may be enhanced, which may make the image easier to view. While geometric perspective is not used in an exemplary embodiment of graphical system 100 (FIG. 1), in other embodiments geometric perspective may be used to complement the stereopsis scaling because it also enhances the stereopsis. For example, the frustum may be used to scale objects based on their distance z from viewer 122 (FIG. 1).

A lighting monoscopic depth cue may be based on the experience of viewer 122 (FIG. 1) that bright objects or objects with bright colors appear to be nearer than dim or darkly colored objects. In addition, the relative positions of proximate objects may be perceived by viewer 122 (FIG. 1) based on how light goes through the presented scene (e.g., solid objects versus non-solid objects). This monoscopic depth cue may be implemented by defining the position of a light source, defining transfer functions of the objects, and using the frustum. A similar monoscopic depth cue is depth cueing, in which the intensity of an object is proportional to the distance from viewer 122 in FIG. 1 (which may also be implemented using the frustum).

Shading may provide a related monoscopic depth cue because shadows cast by an object can make the object appear to be resting on a surface. Note that both lighting and shading may be dependent on a priori knowledge of viewer 122 (FIG. 1) because they involve viewer 122 (FIG. 1) understanding the light-source position (or the direction of the light) and how shadows in the scene will vary based on the light-source position.

Occlusion (or interposition) may provide a monoscopic depth cue based on the experience of viewer 122 (FIG. 1) that objects that are in front of others will occlude the objects that are behind them. Once again, this effect may be dependent on a priori knowledge of viewer 122 (FIG. 1). Note that lighting, shading and occlusion may also define and interact with motion parallax, based on how objects are positioned relative to one another as viewer 122 (FIG. 1) moves relative to display 114 (FIG. 1). For example, the focal point of the light illuminating the object in a scene may change with motion and this change may be reflected in the lighting and the shading (similar to what occurs when an individual is moving in sunlight). Furthermore, the occlusion may be varied in a manner that is consistent with motion of viewer 122 (FIG. 1), As described previously, the transfer functions that may be used to implement occlusion may be defined in graphical system 100 (FIG. 1) prior to graphics engine 112 in FIG. 1 (for example, by data engine 110 in FIG. 1). The transfer functions for objects may be used to modify the greyscale intensity of a given object after the projection on to the 2D viewing plane. In particular, during the projection on to the 2D viewing plane the average, maximum or minimum greyscale intensity projected into a given voxel may be used, and then may be modified by one or more transfer functions. For example, three sequential voxels in depth may have intensities of 50 to 100, −50 to 50, and −1000 to −50. These intensities may be modified according to a transfer function in which: greyscale values between 50 and 100 may have 0% intensity; greyscale values between −50 to 50 may have 100% intensity; and greyscale values between −1000 to −50 may have 50% intensity. In this way, the perspective may emphasize the second voxel and, to a lesser extent, the third voxel. In another example, transfer functions may be used to illustrate blood so that blood vessels appear filled up in the stereoscopic images, or to hide blood so that blood vessels appear open in the stereoscopic images.

Textural gradients for certain surfaces may also provide a monoscopic depth cue based on the experience of viewer 122 (FIG. 1) that the texture of a material in an object, like a grassy lawn or the tweed of a jacket, is more apparent when the object is closer. Therefore, variation in the perceived texture of a surface may allow viewer 122 (FIG. 1) to determine near versus far surfaces.

Computer System

Figure 6:
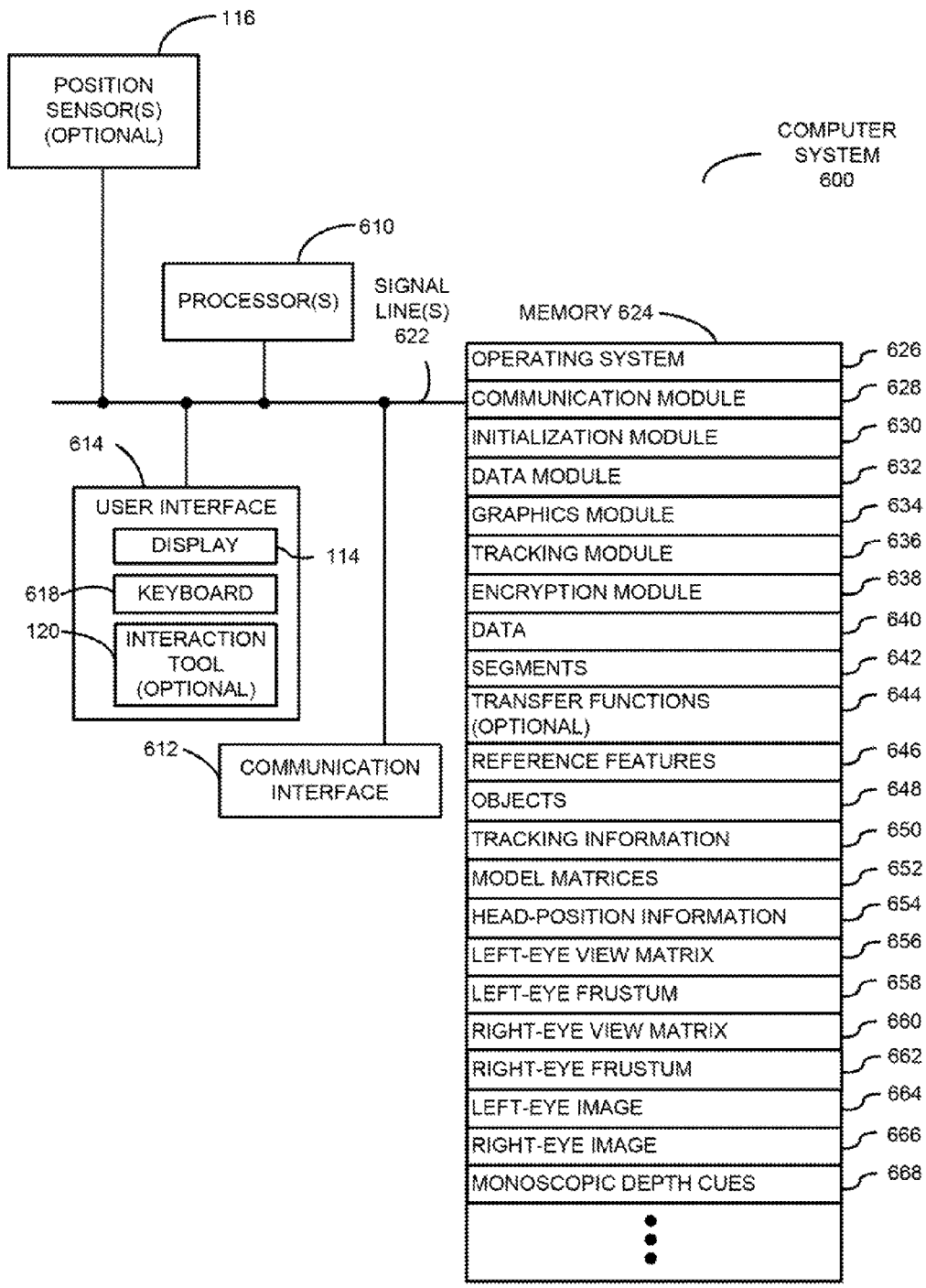
FIG. 6 is a block diagram illustrating a computer system in accordance with an embodiment of the present disclosure.

FIG. 6 presents a drawing of a computer system 600 that implements at least a portion of graphical system 100 (FIG. 1). This computer system includes one or more processing units or processors 610, a communication interface 612, a user interface 614, and one or more signal lines 622 coupling these components together. Note that the one or more processors 610 may support parallel processing and/or multi-threaded operation, the communication interface 612 may have a persistent communication connection, and the one or more signal lines 622 may constitute a communication bus. Moreover, the user interface 614 may include: a display 114, a keyboard 618, and/or an optional interaction tool 120 (such as a stylus, a pointer a mouse and/or a sensor or module that detects displacement of one or more of the user's fingers and/or hands).

Memory 624 in computer system 600 may include volatile memory and/or non-volatile memory. More specifically 624 may include: ROM, RAM, EPROM, EEPROM, flash memory, one or more smart cards, one or more magnetic disc storage devices, and/or one or more optical storage devices. Memory 624 may store an operating system 626 that includes procedures (or a set of instructions) for handling, various basic system services for performing hardware-dependent tasks. Memory 624 may also store procedures (or a set of instructions) in a communication module 628. These communication procedures may he used for communicating with one or more computers and/or servers, including computers and/or servers that are remotely located with respect to computer system 600.

Memory 624 may also include multiple program modules (or sets of instructions), including: initialization module 630 for a set of instructions), data module 632 (or a set of instructions) corresponding to data engine 110 (FIG. 1), graphics module 634 (or a set of instructions) corresponding to graphics engine 112 (FIG. 1), tracking module 636 (or a set of instructions) corresponding to tool engine 118 (FIG. 1), and/or encryption module 638 (or a set of instructions). Note that one or more of these program modules (or sets of instructions) may constitute a computer-program mechanism. These program modules may be used to perform or implement: initialization, object identification and segmentation, virtual instruments, prehension and motion parallax, as well as the image processing rendering operations described previously.

Initialization

During operation, initialization module 630 may define parameters for image parallax and motion parallax. In particular, initialization module 630 may initialize a position of a camera in display 114 in a monoscopic view matrix by setting a position equal to the offset d between the viewing plane and the near plane of the frustum. (Alternatively, there may be a camera in optional interaction tool 120 that can be used to define the perspective. This may be useful in surgical planning.) For example, the offset d may be 1 ft or 0.3 m. Moreover, the focal point (0, 0, 0) may be defined, as the center of the (x, y, z) plane and the axis may be defined as the 'up' direction.

Furthermore, the near and far planes in the frustum may be defined relative to the camera (for example, the near plane may be at 0.1 m and the far plane may be between 1.5-10 m), the right and left planes may be specified by the width in size 126 (FIG. 1) of display 114, and the top and bottom planes may be specified by the height in size 126 (FIG. 1) of display 114. Initialization module 630 may also define the interpupillary distance ipd equal to a value between 62 and 65 mm (in general, the ipd may vary between 55 and 72 mm). Additionally, initialization module 630 may define the display rotation angle θ (for example, θ may be 30°, where horizontal in 0°) and may initialize a system timer (sT) as well as tracking module 636 (which monitors the head position of viewer 122 in FIG. 1, the position of optional interaction tool 120, and which may monitor the gaze direction of viewer 122 in FIG. 1).

Then, initialization module 630 may perform prehension initialization. In particular, start and end points of optional interaction tool 120 may be defined. The start point may be at (0, 0, 0) and the end point may be at (0, 0, tool length), where tool length may be 15 cm, Next, the current (prehension) position of optional interaction tool 120 (PresPh) may be defined, with a corresponding model matrix defined as an identity matrix. Moreover, a past (prehension) position of optional interaction tool 120 (PastPh) may be defined with a corresponding model matrix defined as an identity matrix. Note that prehension history of position and orientation of optional interaction tool 120 can be used to provide a video of optional interaction tool 120 movements, which may be useful in surgical planning.

In addition, initialization module 630 may initialize monoscopic depth cues. In some embodiments, a plane 25-30% larger than the area of display 114 is used to avoid edge effects and to facilitate the stereopsis scaling described previously. In some embodiments, the stereopsis scaling is adapted for a particular viewer based on factors such as: age, the wavelength of light in display 114, sex, the display intensity, etc. Moreover, the monoscopic depth-cue perspective may be set to the horizontal plane (0, 0, 0), and the monoscopic depth-cue lighting may be defined at the same position and direction as the camera in the view matrix.

Object Identification and Segmentation

Figure 7:
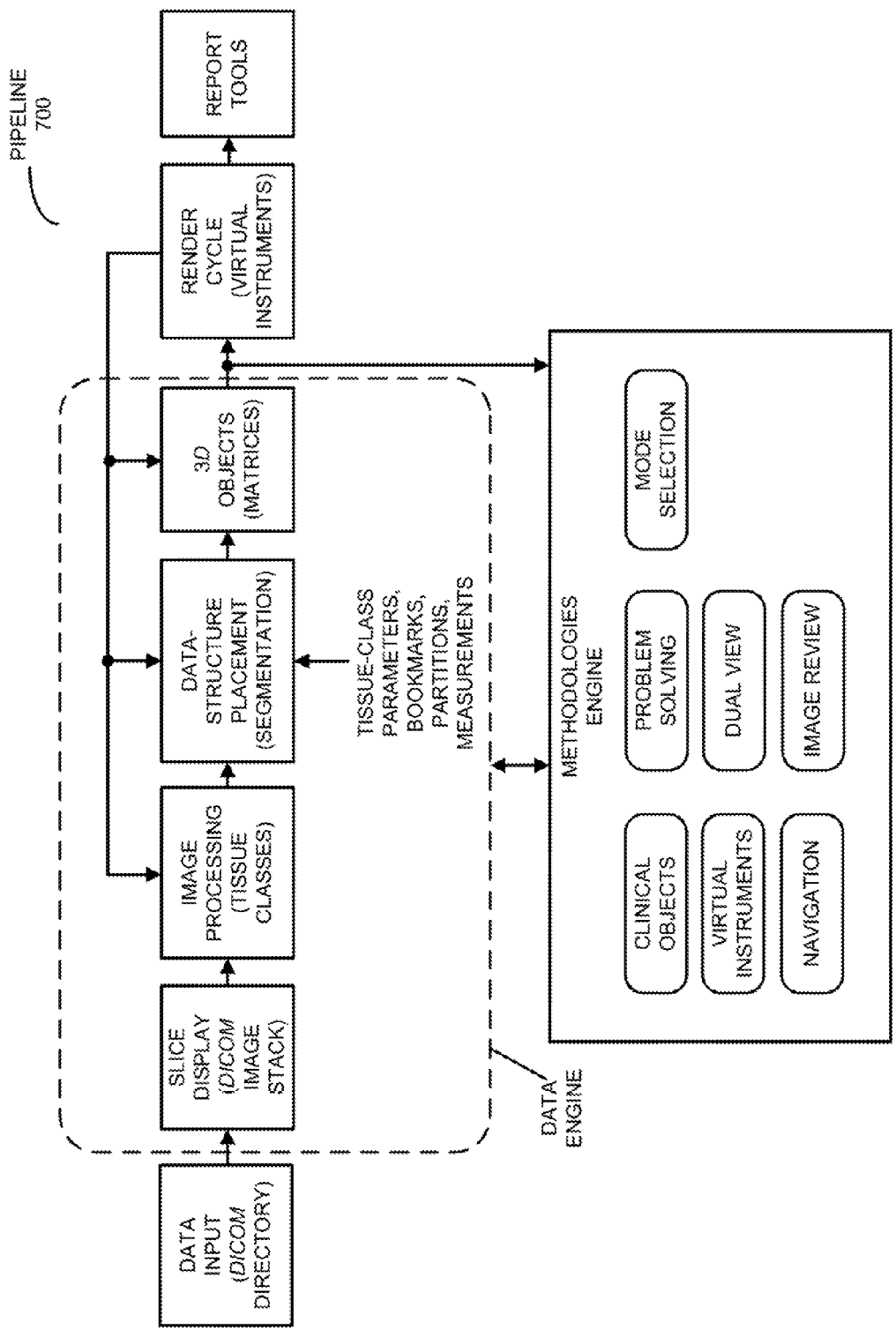
FIG. 7 is a block diagram illustrating a pipeline performed by the computer system of FIG. 6 in accordance with an embodiment of the present disclosure.

After the initialization is complete, data module 632 and graphics module 634 may define or may receive information from the user specifying: segments 642, optional transfer functions 644, reference features 646 and objects 648 in data 640. These operations are illustrated in FIG. 7, which presents a drawing illustrating a pipeline 700 performed by computer system 600 in FIG. 6. In particular, data 640 in FIG. 6 may include a DICOM directory with multiple DICOM images (i.e., source image data from one or more imaging devices), such as a series of 2D images that together depict a volumetric space that contains the anatomy of interest. Data module 632 in FIG. 6 may parse DICOM labels or tags associated with the DICOM images so that a number of images in the series are extracted along with their associated origin coordinate, orientation and voxel x,y and z spacing. (Note that, in general, data 640 may be isometric or non-isometric, i.e., dx, dy and dz may be the same or may be different from each other.) Then, each image of the series is loaded according to its series number and compiled as a single 3D collection of voxels, which includes one of more 3D objects 648 in FIG. 6 (and is sometimes referred to as a 'DICOM image object' or a 'clinical object').

Next, data module 632 may dimensionally scale as opposed to the stereopsis scaling) the DICOM image object. For example, data module 632 may scale all the x voxels by multiplying, their spacing value by 0.001 to assure the dimensions are in millimeters. Similarly, data module 632 may scale all the voxels and all the z voxels, respectively, by multiplying their spacing values by 0.001 to assure the dimensions are in millimeters. This dimensional scaling may ensure that the voxels have the correct dimensions for tracking and display.

Furthermore, data module 632 may map the DICOM image object on to a plane with its scaled dimensions (i.e., the number of is voxels and the number of y voxels) and may be assigned a model matrix with its original orientation and origin. In some embodiments, graphics engine 634 in FIG. 6 optionally displays a stack of images (which is sometimes referred to as a 'DICOM image stack') corresponding to the DICOM image object in the plane.

Subsequently, via iterative interaction with graphics engine 634 and/or the user, data module 632 may aggregate or define several object lists that are stored in reference features 646 in FIG. 6. These object lists may include arrays of objects 648 that specify a scene, virtual instruments (or 'virtual instrument objects), or clinical objects (such as the DICOM image object), and may be used by graphics engine 634 to venerate and render stereoscopic images (as described previously). A 'scene' includes 3D objects that delimit the visible open 3D space. For example, a scene may include a horizontal plane that defines the surface work plane on which all 3D objects in the DICOM image object are placed. Moreover, 'virtual instruments' may be a collection of 3D objects that define a specific way of interacting with any clinical target, clinical anatomy or clinical field. In particular, a virtual instrument includes: a 'representation' that is the basic 3D object elements (e.g., points, lines, planes) including a control variable; and an 'instrument' that implements the interaction operations based on its control variables to its assigned clinical target, clinical anatomy or clinical field. Note that a 'clinical field' may be a clinical object that defines a region within the DICOM image object that contains the anatomy of interest; 'clinical anatomy' may be a clinical object that defines the organ or tissue that is to be evaluated; and a 'clinical target' may be a clinical object that defines the region of interest of anatomy that is the candidate to be diagnosed or evaluated. (Clinical fields, clinical anatomy and clinical targets may be determined by the user and/or data module 632 during a segmentation process, which is described further below.) Note that, in some embodiments, a virtual instrument includes a software-extension of optional interaction tool 120 which can perform specific interaction tasks or operations. Furthermore, note that the user: cannot interact with scenes; may only be able to interact with virtual instruments through their control variables; and may have free interaction with clinical objects.

During iterative interaction, data module 632 may perform image processing on the DICOM image object to identify different levels of organ or tissue of interest. In particular, for the clinical field, the DICOM image object may be processed to identify different tissue classes (such as organ segments, vessels, etc.) as binary 3D collections of voxels based on the voxel values, as well as the boundaries between them. In the discussion that follows, a probability-mapping technique is used to identify the tissue classes. However, in other embodiments, different techniques may be used, such as: a watershed technique, a region-growing-from-seeds technique, or a level-set technique.

In the probability-mapping technique, a probability map (P) is generated using a 3D image with the same size as one of the DICOM images. The values of P may be the (estimated) probability of voxels being inside, outside and at the edge of the organ of interest. For each voxel, P may be obtained by computing three (or more) probabilities of belonging to tissue classes of interest, such as: voxels inside the organ (tissue class w1), voxels outside the organ (tissue class w2), and voxels at the interface between organs (tissue class w3). For a given voxel, P may be determined from the maximum of these three probabilities. Note that each probability may be calculated using a cumulative distribution function, e.g., $$F(x, x_o, \gamma) = \frac{1}{\pi} \cdot \arctan\left(\frac{x - x_o}{\gamma}\right) + \frac{1}{2},$$

where $x_0$ is the density of the tissue class, x is the density of the tested voxel, and γ is a scale parameter of the distribution or the half-width at half-maximum.

The voxels at the interface between the tissue classes may be calculated for a neighborhood of voxels as being part of tissue class w1 or tissue class w2, and then averaging the result. Pseudo-code for this calculation for an omni-directional configuration with 27 neighboring voxels is shown in Table 1.

TABLE 1

```
for each voxel (x, y, z) do
    sum=0;
    for i = -1 to 1 do
        for j = -1 to 1 do
            for k = -1 to 1 do
                sum += P(w1j(x + i, y + j, z + k));
                sum += P(w2j(x + i, y + j, z + k));
            end;
        end;
    end;
    P(w3j(x, y, z)) = sum/27;
end
```

Additionally, during the iterative interaction data module 632 may perform image processing on the DICOM image object to identify the clinical anatomy. In particular, using the organ binary mask a ray-casting technique can be applied to generate a volume image of the organ of interest, such as the liver or another solid organ. Furthermore, using the boundary-voxel mask, a surface can be generated of the tissue using a marching-cube technique, such as the surface of a vessel (e.g., the large intestine or an artery). Note that other surfaces or ray-casting volumes can be generated from the segmented data.

In an exemplary embodiment, the determined clinical field may be the chest, the clinical anatomy may be the aorta, and the clinical target may be the aortic valve. Alternatively, the clinical field may be the abdomen, the clinical anatomy may be the colon, and the clinical target may be the one or more polyps.

After the image processing, data module 632 may perform the segmentation process (including data-structure processing and linking) to identify landmarks and region-of-interest parameters. The objective of the segmentation process is to identify functional regions of the clinical anatomy to be evaluated. This may be accomplished by an articulated model, which includes piece wise rigid parts for the anatomical segments coupled by joints, to represent the clinical anatomy. The resulting segments 642 in FIG. 6 may each include: a proximal point (S) location specified by the DICOM image-voxel index coordinate ($i_1 j_1$, $k_1$); a distal point. (D) location specified by the DICOM image-voxel index coordinate ($i_2$, $j_2$, $k_2$); a central point (C) location specified by the DICOM image-voxel index coordinate ($i_3$, $j_3$, $k_3$), which may be the half point of the Euclidean distance between S and D; image-voxel index bounds (B) of the region of interest surrounding the central point including the proximal and distal points ($i_{min}$, $i_{max}$, $j_{min}$, $j_{max}$, $k_{min}$, $k_{max}$); and the corresponding world x, y, z coordinates of the central point and the region hounds locations calculated by accounting for the x, y, z voxel spacing of the source DICOM image. In general, segments 642 may be determined using an interactive segmentation technique with the user and or a computer-implemented segmentation technique.

In the interactive segmentation technique, the user may select or specify n voxel index locations from the clinical field, which may be used to define the central points (Cs). Then, a 3D Voronoi map (and, more generally, a Euclidean-distance map) may determine regions around each of the selected index locations. For each of the Voronoi regions and each of the n voxel indexes, data module 632 may obtain: the minimum voxel index along the x axis of the DICOM image ($i_{min}$); the maximum voxel index along the x axis of the DICOM image ($i_{max}$); the minimum voxel index along the x axis of the DICOM image ($j_{min}$); the maximum voxel index along the y axis of the DICOM image ($j_{max}$); the minimum voxel index along the z axis of the DICOM image ($k_{min}$); and the maximum voxel index along the z axis of the DICOM image ($k_{max}$). Next, data module 632 may define: the proximal S point as $i_{min}$, $j_{min}$, $k_{min}$; and the distal D point as $i_{max}$, $j_{max}$, $k_{max}$. Moreover, data module 632 may generate a list of 3D objects (such as anatomical segments) of the clinical anatomy based on these values and may add these 3D objects to the object list of clinical objects in reference features 646 for use by graphics module 634.

As described further below with reference to FIGS. 10-23, using the interactive or the computer-based segmentation technique, the surface of the colon may be a single object or may be sub-divided into six segments or more. Depending on the tortuosity of the colon, this calculation may involve up to 13 iterations in order to obtain segments with the desired aspect ratios.

As described further below with reference to FIG. 36, the articulated model may facilitate: fast extraction of regions of interest., reduced storage requirements (because anatomical features may be described using a subset of the DICOM images or annotations within the DICOM images), faster generating and rendering of True 3D stereoscopic images with motion parallax and/or prehension, and a lower cost for the graphical system.

Virtual Instruments

As described previously in the discussion of image processing and rendering operations, graphics module 634 may generate 30 stereoscopic images. Furthermore, prior to rendering these 3D stereoscopic images and providing them to display 114, stereopsis scaling may he performed to enhance or optimize the stereo acuity of the user based on the maximum and minimum scale factors (i.e., the range of scaling) that can be applied to the anatomical segments $dz_{min}$ and $dz_{max}$. During the rendering, once the anatomy has been adequately segmented and linked, graphics module 634 may also implement interaction using one or more virtual instruments. For example, a virtual instrument may allow the user to navigate the body parts, and to focus on and to evaluate a segment of a patient's anatomy, allowing the user to optimize workflow.

Each virtual instrument includes: a 'representation' which is the basic object elements (points, lines, planes, other 3D objects, etc.) including a control variable; and an 'instrument' which implements the interaction operations based on its control variables to its assigned clinical target, clinical anatomy or clinical field. While a wide variety of virtual instruments can be defined (such as a pointer or a wedge), in the discussion that follows a dissection cut plane, a bookmark to a region of interest, a problem-solving tool that combines a 3D view with a 2D cross-section, and an 'intuitive 2D' approach that allows the viewer to scroll through an array of 2D images using stylusare used as illustrative examples.

For the cut-plane virtual instrument, the representation includes: an origin point (Origin) that defines an origin $x_0$, $y_0$, $z_0$ position of the cut plane; point 1 that, in conjunction with the origin point, defines axis 1 ($a_1$) of the cut plane; and point 2 that, in conjunction with the origin point, defines axis 2 ($a_2$) of the cut plane. The normal to the cut plane points in the direction of the cross product of $a_1$ and $a_2$. Moreover, the center point (Center Point) is the control point of the cut plane. In particular, Center[x]=Origin[$x_0$]+0.5($a_1$[x]+$a_2$[x])

Center[y]=Origin[$y_0$]+0.5($a_1$[y]+$a_2$[y])

and

Center[z]=Origin[$z_0$]+0.5($a_1$[z]+$a_2$[z]).

The user can control the cut plane by interacting with the center point, and can translate and rotate the cut plane using optional interaction tool 120 in FIG. 6. For example, the user can control a cut plane to uncover underlying anatomical features thereby allowing the rest of the anatomical segment to be brought into view by rotating the anatomical segment. Note that the cut plane may modify the bounding-box coordinates of the anatomical segment by identifying the intersection points of the cut plane to the hounding box in the direction of the normal of the cut plane.

For the bookmark virtual instrument, the representation includes: point 1 that defines $x_{min}$, $y_{min}$ and $z_{min}$; point 2 that defines $x_{max}$, $y_{max}$ and $Z_{max}$. The bookmark may be specified by the center point and the bounds of the box ($x_{min}$, $x_{max}$, $y_{min}$, $y_{max}$, $z_{min}$, $z_{max}$). Moreover, the center point (Center Point) is the control point of the region of interest. In particular, Center[x]=0.5($x_{max}$-$x_{min}$), Center[y]=0.5($y_{max}$-$y_{min}$), and Center[z]=0.5($z_{max}$-$z_{min}$).

The user can control the bookmark by placing it at a center point of an clinical object with a box size equal to 1, or by placing a second point to define a volumetric region of interest. When the volumetric region of interest is placed, that region can be copied for further analysis. Note that using a bookmark, the user can specify a clinical target that can be added to the object list of clinical object for use by graphics module 634.

For the problem-solving virtual instrument, the representation combines a bookmark to a 3D region of interest and a cut plane for the associated 2D projection or cross-section. This representation is summarized in Table 2.

TABLE 2

| 2D Cross-Section | 3D Region of Interest |
|---|---|
| The origin point defines the position of a cut plane ($x_o$, $y_o$, $z_o$). Point 1 defines axis 1 ($a_1$) of the cut plane. Point 2 defines axis 2 ($a_2$) of the cut plane. The normal to the cut plane points in the direction of the cross product of $a_1$ with $a_2$. The center point is the control point of the cut plane. | Point 1 defines $x_{min}$, $y_{min}$ and $z_{min}$. Point 2 defines $x_{max}$, $y_{max}$ and $z_{max}$. The bookmark is defined by the center point and the bounds of the box ($x_{min}$, $x_{max}$, $y_{min}$, $y_{max}$, $z_{min}$, $z_{max}$). The center point is the control point. |

The user can control the problem-solving virtual instrument to recall a bookmarked clinical target or a selected region of interest of a 3D object and can interact with its center point In this case, the surface of the 3D object may be transparent (as specified by one of optional transfer functions 644 in FIG. 6). The 2D cross-section is specified by a cut plane (defined by the origin, point 1 and point 2D that maps the corresponding 2D DICOM image of the cut plane within the region of interest. By interacting with the 2D cross-section center point, the user can determine the optimal 2D cross-sectional image of a particular clinical target. Note that the problem-solving virtual instrument allows the user to dynamically interact with the 3D stereoscopic image and at least one 2D projection. As the user interacts with objects in these images, the displayed images may be dynamically updated. Furthermore, instead of merely rotating an object, the user may be able to 'look around' (i.e., motion parallax in which the object rotates in the opposite direction to the rotation of the user relative to the object), so that they can Observe behind an object, and concurrently can observe the correct 2D projection.

Figure 8A:
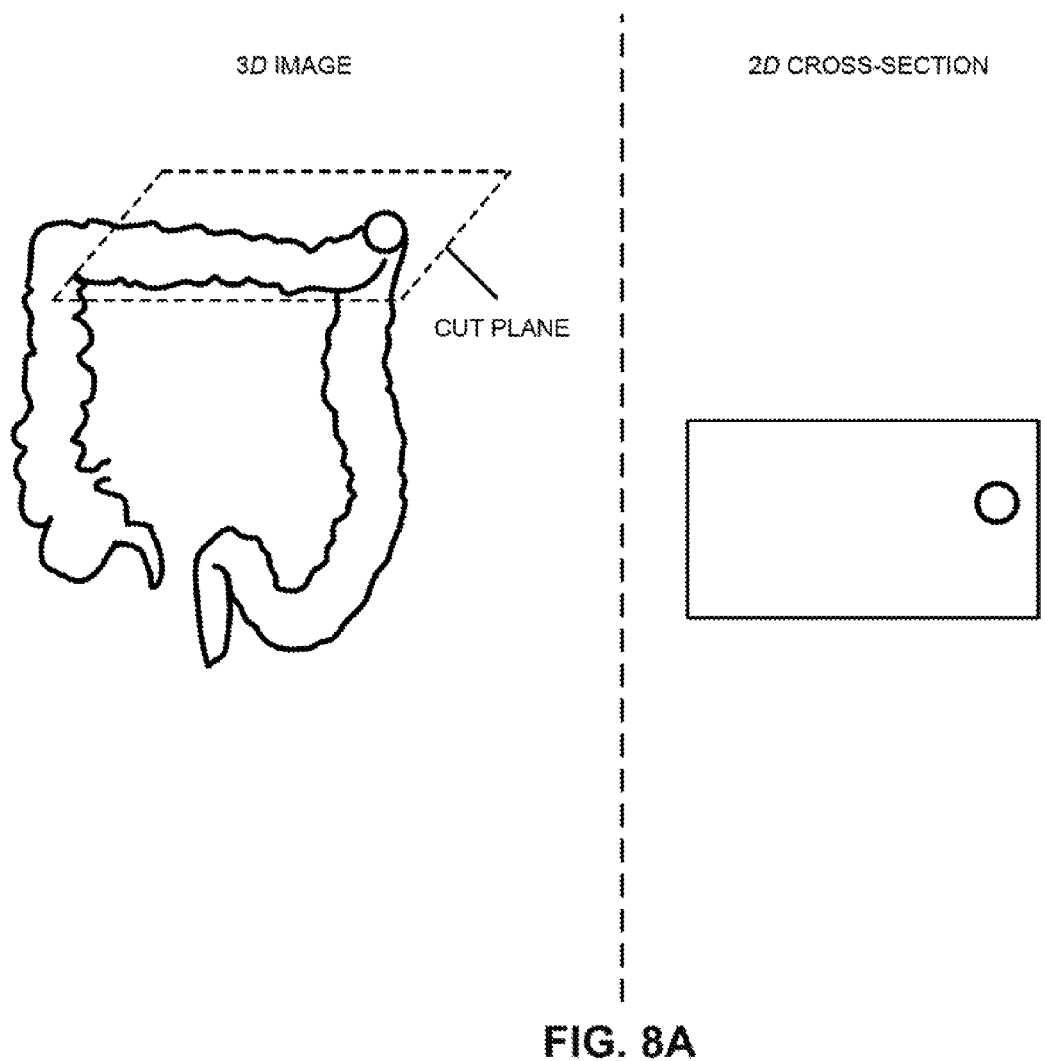
FIG. 8A is a drawing illustrating a display in the graphical system of FIG. 1 in accordance with an embodiment of the present disclosure.
Figure 8B:
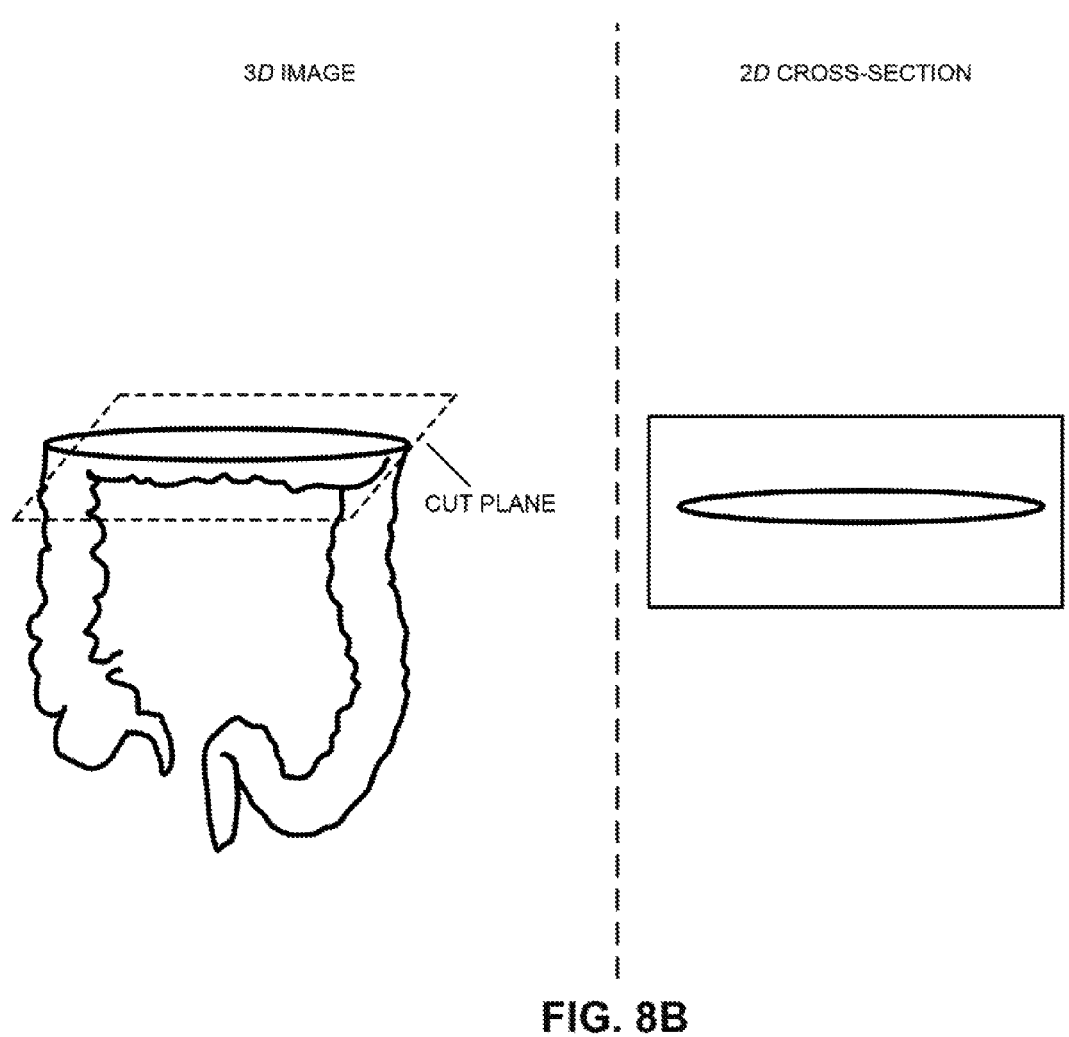
FIG. 8B is a drawing illustrating a display in the graphical system of FIG. 1 in accordance with an embodiment of the present disclosure.
Figure 8C:
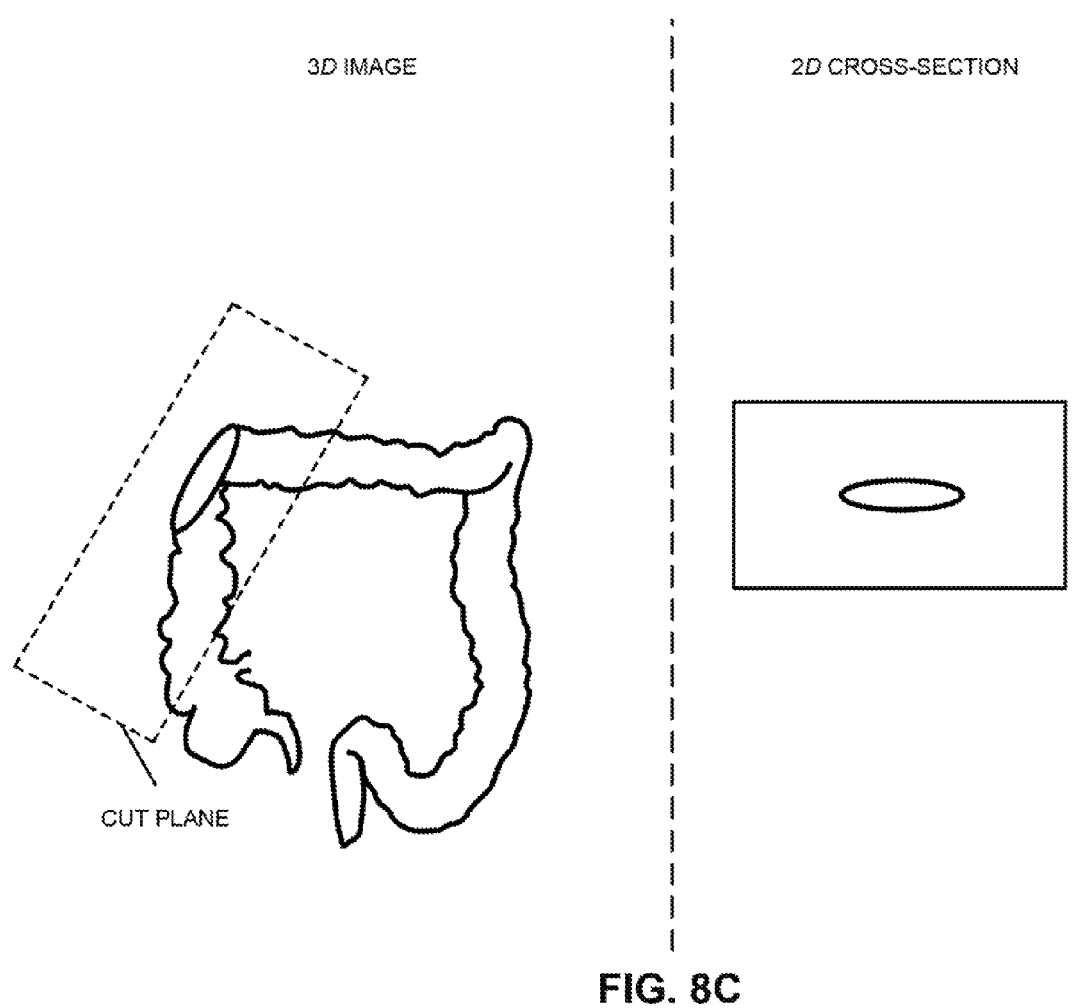
FIG. 8C is a drawing illustrating a display in the graphical system of FIG. 1 in accordance with an embodiment of the present disclosure.

This operation of the problem-solving virtual instrument is illustrated in FIGS. 8A-C, which shows the display of a 3D stereoscopic image and 2D projections side by side (such as on display 114 in FIGS. 1 and 6). When the user moves, changes their viewing direction or perspective and/or interacts with the object (in this case a rectangular cube) in the 3D stereoscopic image, graphics module 634 in FIG. 6 dynamically updates the 2D projection. This may allow the user to look around the object (as opposed to rotating it along a fixed axis). Moreover, by providing accurate and related 2D and 3D images, the problem-solving virtual instrument may allow a physician to leverage their existing training and approach for interpreting 2D images when simultaneously viewing 3D images. This capability is described further below with reference to FIG. 37.

The intuitive 2D virtual instrument presents a 2D image that is displayed is the viewer scrolls through an array of 2D images using a stylus (and, more generally, the optional interaction tool) or a scroll bar. This virtual instrument can improve intuitive understanding of the 2D images.

The intuitive 2D virtual instrument uses a 3D volumetric image or dataset that includes the 2D images. These 2D images include a collection of voxels that describe a volume, where each voxel has an associated 4×4 model matrix. Moreover, the representation for the intuitive 2D virtual instrument is a fixed cut plane, which specifies the presented 2D image (i.e., voxels in the dataset that are within the plane of interaction with the cut plane). The presented 2D image is at position (for example, an axial position) with a pre-defined center (x, y, z position) and bounds ($x_{min}$, $x_{max}$, $y_{min}$, $y_{max}$, $z_{min}$, $z_{max}$). The cut plane, which has a 4×4 rotation matrix with a scale of one, is a two-dimensional surface that is perpendicular to its rotation matrix. Note that the cut plane can be defined by: the origin of the cut plane (which is at the center of the presented 2D image), the normal to the current plane (which is the normal orientation of the presented 2D image), and/or the normal matrix N of the reference model matrix M for the presented 2D image (which defines the dimensions, scale and origin for all of the voxels in the presented 2D image), where N is defined as the transpose (inverse(M)). Another way to define the cut plane is by using the forward (pF) and backward point (pB) of the stylus or the optional interaction tool. By normalizing the interaction-tool vector, which is defined as $$\frac{pF - pB}{|pF - pB|},$$

normal of the cut plane is specified, and the forward point of the stylus of the optional interaction tool specifies the center of the cut plane.

In the intuitive 2D virtual instrument, the normal of the cut plane defines the view direction in which anything behind the cut plane can be seen by suitable manipulation or interaction with the cut plane, while anything in front of the cut plane cannot be seen. Because the dataset for the intuitive 2D virtual instrument only includes image data (e.g., texture values) only the voxel values on the cut plane are displayed. Therefore, transfer functions and segmentation are not used with the intuitive 2D virtual instrument.

By translating/rotating the cut plane using the stylus (or the scroll bar), the viewer can display different oblique 2D image planes (i.e., different 2D slices or cross-sections in the dataset). If the viewer twists their wrist, the intuitive 2D virtual instrument modifies the presented 2D image (in a perpendicular plane to the stylus direction). In addition, using the stylus the viewer can go through axial, saginal or coronal views in sequence. The viewer can point to a pixel on the cut plane and can push it forward to the front.

During interaction with the viewer, for the cut plane the intuitive 2D virtual instrument uses the stylus coordinates to perform the operations of: calculating a translation matrix (Tr) between the past and present position; calculating the rotation (Rm) between the past and present position; calculating the transformation matrix. (Tm) equal to −Tr·Rm·Tr; and applying the transformation to the reference model matrix. Thus, the cut plane is only rotated, while translations forward or backward in the slides are canceled out. Similarly, for the presented 2D image, the intuitive 2D virtual instrument uses the stylus coordinates to perform the operations of: calculating a translation matrix (Tr) between the past and present position; calculating the rotation (Rm) between the past and present position, calculating the transformation matrix (Tm) equal to Rm·(−Tr); and applying the transformation to the reference model matrix. Thus, the presented 2D image includes translations (moving forward or backward in the slides) and includes a 2D slice at an arbitrary angle with respect to fixed (or predefined) 2D data slices based on manipulations in the plane of the cut plane.

Figure 9:
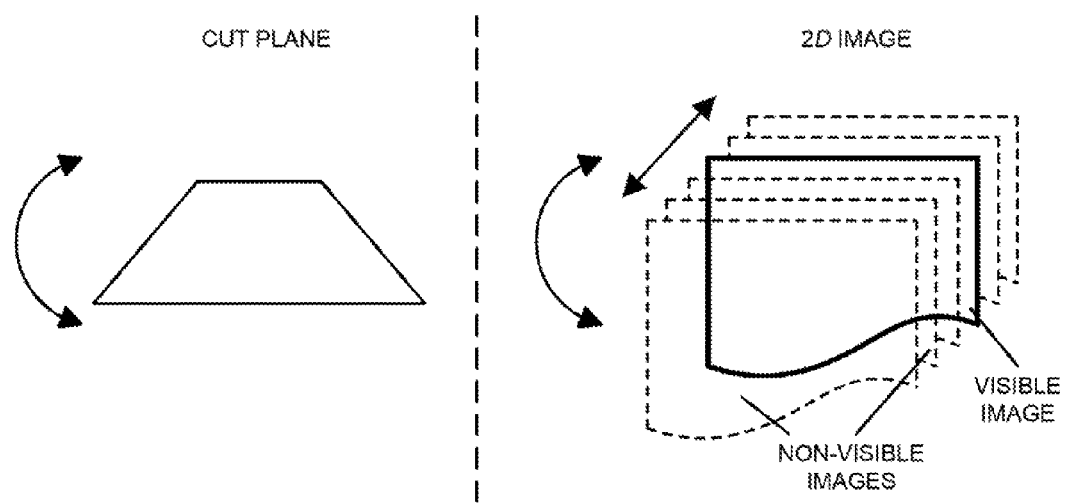
FIG. 9 is a drawing illustrating a virtual instrument in accordance with an embodiment of the present disclosure.

The interaction is illustrated in FIG. 9, which shows the cut plane and the presented 2D image side by side (such as on display 114 in FIGS. 1 and 6) for the intuitive 2D virtual instrument. (in addition, non-visible 2D images surrounding the presented 2D image are illustrated in FIG. 9 using dashed lines.) Based on manipulation of the stylus by the viewer (which can include rotations and/or translations), the cut plane is rotated, while the presented 2D image is translated and/or rotated to uncover voxels. Alternatively or additionally, different cut planes may be specified by bookmarks defined by the viewer (such as anatomical locations of suspected or potential polyps), and associated 2D images may be presented to the viewer when the viewer subsequently scrolls through the bookmarks.

Prehension and Motion Parallax

Referring back to FIG. 6, tracking module 636 may track the position of optional interaction tool 120, for example, using one or more optional position sensors 116. The resulting tracking, information 650 may be used to update the position of optional interaction tool 120 (e.g., PastPh equals PresPh, and PresPh equals the current position of optional interaction tool 120), Graphics module 634 may use the revised position of the optional interaction tool 120 to generate a revised transformation model matrix for optional interaction tool 120 in model matrices 652.

Next, tracking module 636 may test it optional interaction tool 120 is touching or interfacing with one of objects 648 shown in display 114 (note, however, that in some embodiments viewer 122 in FIG. 1 cannot interact with some of reference features 646 using optional interaction tool 120). If yes, the position and orientation of optional interaction tool 120 may be modified, with a commensurate impact on the transformation model matrix in model matrices 652 for optional interaction tool 120. In particular, the translation to be applied to the one of objects 648 (DeltaVector) may be determined based on the x, y and z position of the tool tip (ToolTip) (which is specified by PresPh) and the x, y and z position where optional interaction tool 120 touches the one of objects 648 (ContactPoint) using DeltaVector[x]=ToolTip[x]−ContactPoint[x], DeltaVector[y]=ToolTip[y]−ContactPoint[y], and DeltaVector[z]=ToolTip[z]−ContactPoint[z], The rotation to be applied may be determined using, a local variable (in the form of a 4×4 matrix) called ROT. Initially, ROT may be an identity matrix. The rotation elements of ROT may be determined by matrix multiplying the rotation elements specified by PresPh and the rotation elements specified by PastPh. Then, the following transformation operations are concatenated and applied to the model matrix of the one of objects 648 using a local 4×4 matrix T (which initially includes all 16 elements in the current model matrix: translate T to the negative of the center position of the one of objects 648 (−Center[x], −Center[y], −Center[z]) to eliminate interaction jitter; rotate T by ROT; translate T to the object center (Center[x], Center[y], Center[z]) to eliminate interaction jitter; and translate T to DeltalVector (DeltaVector[x], DeltaVector[y], DeltaVector[z]). Next, the model matrix is replaced with the T matrix.

Note that calculations related to the position of optional interaction tool 120 may occur every 15 ms or faster so that prehension related to optional interaction tool 120 is updated at least 66.67 times per second.

Moreover, tracking module 636 may track the head position of viewer 122 (FIG. 1), for example, using one or more optional position sensors 116. Updates to head-position information 654 may be applied by graphics module 634 to the virtual space and used to render left-eye and right-eye images for display on display 114. In particular, the inverse of left-eye view matrix 656 may be revised by: translating the object relative to the position coordinate of the camera (the monoscopic view matrix $V_0$ that is located at the center of display 114); rotating by θ-90° (which specifies a normal to an inclined display); and translating to the eye of the viewer 122 in FIG. 1 by taking away the original offset d, translating to the current head position and translating left to 0.5 ipd. Thus, $$V_{left\_eye}^{-1} = V_0^{-1} \cdot Rv(\theta - 90°) \cdot Tv(-d) \cdot Tv(\text{head\_position}) \cdot Tv\left(\frac{-ipd}{2}, 0, 0\right).$$

Similarly, left-eye frustum 658 may be revised by: translating to the current head position relative to the offset k (shown in FIGS. 3 and 4) between the eyes of viewer 122 in FIG. 1 and the viewing plane; and translating left to 0.5 ipd. Thus, $$F_{left\_eye} = Tv(0, 0, k) \cdot Tv(\text{head\_position}) \cdot Tv\left(\frac{-ipd}{2}, 0, 0\right).$$

These operations may be repeated for the right eye to calculate right-eye view matrix 660 and right-eye frustum 662, i.e, $$V_{right\_eye}^{-1} = V_0^{-1} \cdot Rv(\theta - 90°) \cdot Tv(-d) \cdot Tv(\text{head\_position}) \cdot Tv\left(\frac{ipd}{2}, 0, 0\right).$$

and $$F_{right\_eye} = Tv(0, 0, k) \cdot Tv(\text{head\_position}) \cdot Tv\left(\frac{ipd}{2}, 0, 0\right).$$

Using the left-eye and the right-eye view and frustum matrices 656-662 graphics module 634 may determine left-eye image 664 for a given transformation model matrix Mt in model matrices 652 based on $$Mt \cdot V_{left\_eye} \cdot F_{left\_eye},$$

and may determine right-eye image 666 for the given transformation model matrix Mt based on $$Mt \cdot V_{right\_eye} \cdot F_{right\_eye},$$

After applying monoscopic depth cues 668, graphics module 634 may display left-eye and right-eye images 666 and 668, on display 114 Note that calculations related to the head position may occur at least every 50-100 ms, and the rendered images may be displayed on display 114 at a frequency of at least 60 Hz for each eye.

In general, objects are presented in the rendered images on display 114 with image parallax. However, in an exemplary embodiment the object corresponding to optional interaction tool 120 on display 114 is not be represented with image parallax.

Therefore computer system 600 may implement a data-centric approach (as opposed to a model-centric approach) to generate left-eye and right-eye images 664 and 666 with enhanced for optimal) depth acuity for discrete-sampling data. However, in other embodiments the imaging technique may be applied to continuous-valued or analog data. For example, data module 632 may interpolate between discrete samples in data 640. This interpolation (such as minimum bandwidth interpolation) may be used to resample data 640 and/or to generate continuous-valued data.

White the preceding discussion illustrated left-eye and right-eye frustums with near and far (clip) planes that can cause an object to drop out of left-eye and right-eye images 664 and 666 if viewer 122 (FIG. 1) moves far enough away from display 114, in some embodiments the left-eye and right-eye frustums provide a more graceful decay as viewer 122 (FIG. 1) moves away from display 114. Furthermore, when the resulting depth acuity in left-eye and right-eye images 664 and 666 is sub-optimal, intuitive clues (such as by changing, the color of the rendered images or by displaying an icon in the rendered images) may be used to alert viewer 122 (FIG. 1).

Furthermore, while the preceding embodiments illustrated prehension in the context of motion of optional, interaction tool 120, in other embodiments additional sensory feedback may be provided to viewer 122 (FIG. 1) based on motion of optional interaction tool 120. For example, haptic feedback may be provided based on annotation, metadata or CT scan Hounsfield units about materials having different densities (such as different types of tissue) that may be generated by data module 632. This haptic feedback may be useful during surgical planning or a simulated virtual surgical procedure.

Because information in computer system 600 may be sensitive in nature, in some embodiments at least some of the data stored in memory 624 and/or at least some of the data communicated using communication module 628 is encrypted using: encryption module 638, Instructions in the various modules in memory 624 may be implemented in: a high-level procedural language, an object-oriented programming language, and/or in an assembly or machine language. Note that the programming language may be compiled or interpreted, e,g, configurable or configured, to be executed by the one or more processors 610.

Although computer system 600 is illustrated as having a number of discrete components, FIG. 6 is intended to be a functional description of the various features that may be present in computer system 600 rather than a structural schematic of the embodiments described herein. In some embodiments, some or all of the functionality of computer system 600 may be implemented in one or more application-specific integrated circuits (ASICs) and/or one or more digital signal processors (DSPs).

Computer system 600, as well as electronic devices, computers and servers in graphical system 100 (FIG. 1), may include one of a variety of devices capable of performing operations on computer-readable data or communicating such data between two or more computing systems over a network, including: a desktop computer, a laptop computer, a tablet computer, a subnotebook/netbook, a supercomputer, a mainframe computer, a portable electronic device such as a cellular telephone or PDA), a server, a portable computing device, a consumer-electronic device, a Picture Archiving and Communication System (PACS), and/or a client computer (in a client-server architecture). Moreover, communication interface 612 may communicate with other electronic devices via a network, such as: the Internet, World Wide Web (WWW), an intranet, a cellular-telephone network, LAN, WAN, MAN, or a combination of networks, or other technology enabling communication between computing systems.

Graphical system 100 (FIG. 1 and/or computer system 600 may include fewer components or additional components. Moreover, two or more components may be combined into a single component, and/or a position of one or more components may be changed. In some embodiments, the functionality of graphical system 100 (FIG. 1) and/or computer system 600 may be implemented more in hardware and less in software, or less in hardware and more in software, as is known in the art.

Applications

By combining image parallax, motion parallax, prehension and stereopsis scaling to create an interactive stereo display, it is possible for users of the graphical system to interact with displayed 3D objects as if they were real objects. For example, physicians can visually work with parts of the body in open 3D space. By incorporating the sensory cues associated with direct interaction with the displayed objects, it is believed that both cognitive and intuitive skills of the users win be improved. This is expected to provide a meaningful increase in the user's knowledge.

In the case of medicine, this cognitive-intuitive tie can provide a paradigm shift in the areas of diagnostics, surgical planning and a virtual surgical procedure by allowing physicians and medical professionals to focus their attention on solving clinical problems without the need to struggle through the interpretation of 3D anatomy using 2D views. This struggle, which is referred to as 'spatial cognition,' involves viewing 2D images and constructing a 3D recreation in your mind (a cognitively intensive process). In the absence of the True 3D provided by the graphical system, the risk is that clinically significant information may be lost. The True 3D provided by the graphical system may also address the different spatial cognitive abilities of the physicans and medical professionals when performing spatial cognition.

In the discussion that follows, computed tomography colonography (CTC) is used as an illustrative example of the application of the graphical system and True 3D. However, in other embodiments the graphical system and True 3D are used in a wide variety of applications, including medical applications (such as mammography) and non-medical applications.

Colorectal cancer (CRC) is the third most commonly diagnosed cancer and the second most common cause of cancer deaths in the U.S. This is despite the availability of traditionally employed screening tools like optical colonoscopy and others. CTC is sometimes referred to as 'virtual colonoscopy') is a noninvasive screening test for CRC. The goal of CTC is to visually locate and identify polyp candidates, the precursor lesions of CRC.

However, existing CTC visualization techniques often have limitations in representing the complex 3D relationships present in the colon wall and haustral folds, and in the differentiation of CTC pitfalls, such as residual stool and thickened folds. The ability to represent these relationships and features can facilitate polyp detection, as well as detecting other lesions, such as diverticula, lipomas, external compressions and possible surgical changes. In the absence of such capabilities, there is often a steep learning, curve for CTC readers or viewers, which can slow test dissemination. In particular, readers typically integrate a series of 2D images and mentally extract the relevant 3D relationships that define a polyp, which is a highly intense, cognitive process that can result in errors. Moreover, low-dose CTC protocols that yield lower quality images and computer-aided detection (CAD) may be associated with high false-positive rates, which can increase the intensity and complexity of CTC interpretation.

These challenges are addressed using True 3D CTC (which is sometimes referred to as 'True 3D computed tomography colonography' or 'True 3D-CTC'). In True 3D-CTC, a reader (such as a physician) may: select a CTC case; process the CTC case images to extract a 3D model of the colon lumen and bookmark polyp candidates; and implement a True 3D-CTC interpretation process to locate and evaluate polyps. After selecting a CTC case, the reader can view the CT images and scroll through them and view 3D objects in open 3D space. Moreover, the reader can directly interact with colon segments (CS) and colonic lesions (such as polyps, diverticula, lipomas, etc.) using an intuitive hand-directed stylus as the optional interaction tool to assess their diagnostic quality while the images are processed in the background by the graphical system. Thus, True 3D-CTC provides as protocol with methodologies and tools that allow readers to comprehensively evaluate the colon wall and locate polyps employing a fully interactive solution.

The True 3D-CTC protocol may use virtual and augmented reality visualization systems that integrate stereoscopic rendering, stereoscopic acuity scaling, motion parallax and/or prehension capabilities to provide a True 3D view of the colon. In particular, the True 3 D-CTC protocol may include methodologies such as: a colon-segment (CS) navigation methodology that facilitates the evaluation of the colon lumen and enhances polyp conspicuity; a problem-solving methodology to assess lesion tissue-density homogeneity with morphologic polyp features; a dual-view methodology for comparing colon anatomy from different patient-position images; and or a general image-review methodology that presents image data spatially registered to the location and orientation of patient within the open 3D space.

Moreover, the True 3D-CTC protocol methodologies may be enabled or driven by tools such as: a colon-segmentation technique that creates a 3D surface model of the colon; a digital subtraction bowel cleansing (DBSC) technique that extracts a volumetric mask of the contrast material that is present in a patient's colon; a colon-centerline technique that extracts a curved center path or centerline along the length of the extracted 3D colon model; a centerline curvature-evaluation technique that quantifies the curvature, torque and or tortuosity at each point along a colon centerline; a 3D bookmarking tool that allows the reader to identify candidate or potential polyps; a measurement tool that allows the reader to measure polyps; and/or a report data structure that contains the image data orientation, position and the current state of the True 3D-CTC application.

During CTC the colon may be insufflated with carbon dioxide and multi-detector CT images may be obtained in seconds such as less than 3 mm multi-detector CT images). The contrast between the colon wall and the gas filled lumen may enable readers to evaluate endoluminal views of the colon to identify polyps, the precursor lesion to colon cancer. While patient preparation for CTC can vary, the patient usually is asked to take laxatives or other oral agents at home the day before the CTC procedure to clear stool from the colon. The patient may also be given a solution designed to coat any residual fecal material that may not have been cleared by the laxative (which is sometimes referred to as 'fecal tagging'), which appears as high-contrast areas in the colon lumen.

Moreover, during the CT scan, the patient may be placed in a supine position on the examination table. A thin tube may be inserted into the rectum, so that $CO_2$ or air can he pumped through the tube in order to inflate and distend the colon wall for better viewing. The examination table may be moved through the scanner to produce a series of 2D cross-sections along the length of the colon. The scan may then be repeated with the patient lying in a prone position and/or in a decubitus position.

After the CT scan, the images produced by the scanner can be processed and evaluated utilizing the True 3D-CTC protocol. Referring back to FIG. 1, graphical system 100 may facilitate close-range stereoscopic viewing of 3D objects (such as those depicting human anatomy, such as a colon) with unrestricted head motion and hand-directed interaction with the 3D objects, thereby providing, a rich holographic experience, in particular, data engine 110, graphics engine 112 and tool engine 118 may provide a protocol for evaluating CTC image data as a part of a diagnostic and colon-cancer screening process as a turnkey solution.

Referring back to FIGS. 2-4, the protocol may use the frustum or 'open 3D space' that is dynamically created by graphical system 100 (FIG. 1) in order to present an enhanced view of polyps and the complex 3D relationships present in the colon wall, haustral folds and other CTC pitfalls, such as residual stool and thickened folds.

Furthermore, the protocol may use the stereoscopic-acuity capabilities (which were described previously with reference to FIG. 5) to increase the conspicuity of polyps by stereoscopically scaling the objects displayed within the frustum.

In the discussion that follows, the implementation of protocol tools in data engine 110 (FIG. 1) and the implementation of the methodologies of the protocol in graphics engine 112 (FIG. 1) and tool engine 114 (FIG. 1) are described.

Figure 10:
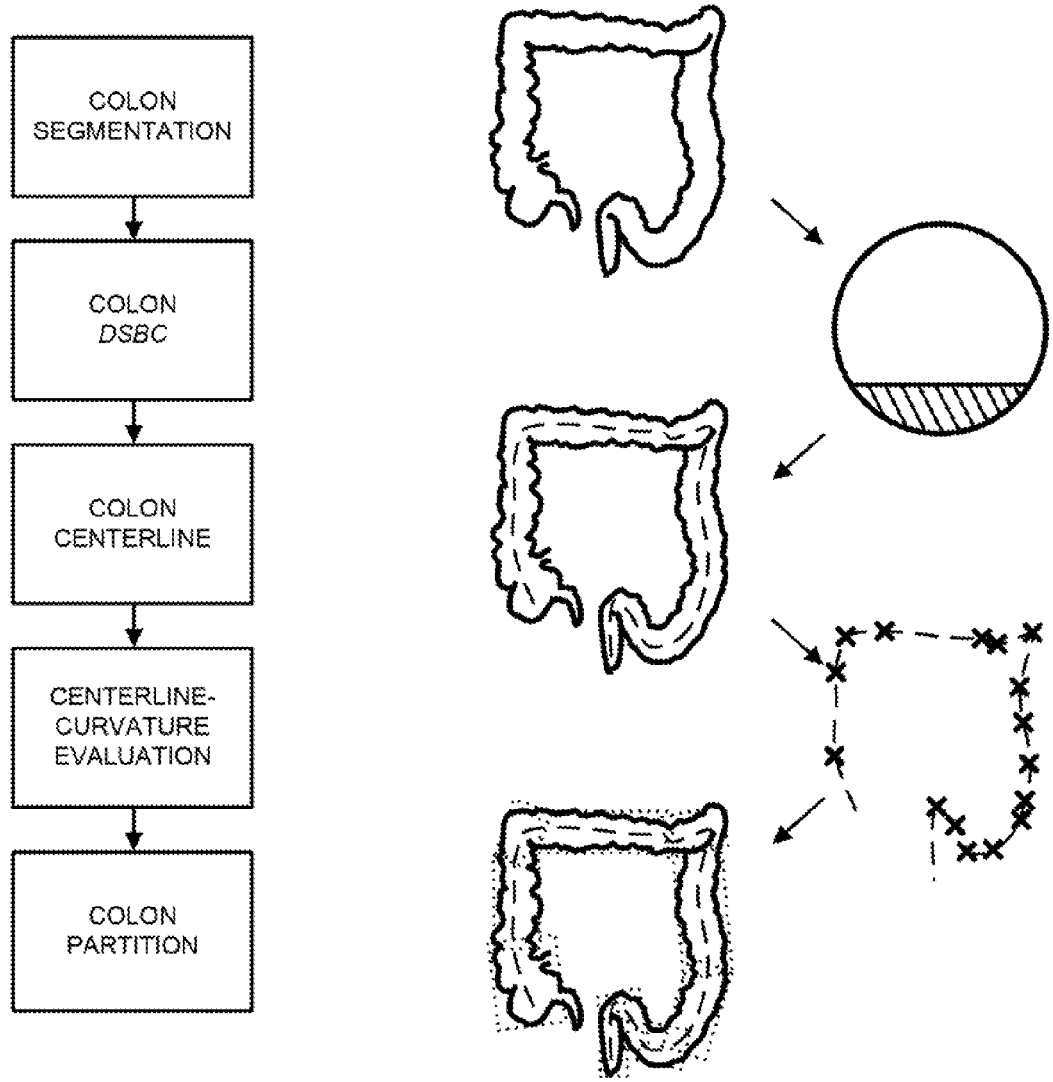
FIG. 10 is a drawing illustrating imaging processing for a computed tomography colonography (CIO in accordance with an embodiment of the present disclosure, FIG. 11 is a drawing illustrating segmentation of a colon in accordance with an embodiment of the present disclosure.

Data engine 110 (FIG. 1) may perform segmentation, centerline extraction, colon partition and/or subtraction. In particular, after the initialization is complete, data engine 110 (FIG. 1) may read in a CTC DICOM study and may optionally send it to graphics engine 112 (FIG. 1) for display as a DICOM image stack (as described previously with reference to FIG. 7). Then, as shown in FIG. 10, presents a drawing illustrating imaging processing for a CTC, data engine 110 (FIG. 1) may perform: colon identification and segmentation, digital subtraction bowel cleansing (DSBC) of contrast material, centerline extraction, centerline curvature evaluation, and/or colon partition.

During colon identification and segmentation, data engine 110 (FIG. 1) may segment the colon by obtaining a probability map P. In particular, for each voxel graphical system 100 (FIG. 1) may calculate three probabilities of belonging to each of the three tissue classes of interest (air, liquid and interface or boundary, where the union of these three tissue classes farms the inside of the colon), and then taking P as the maximum of these three probabilities.

Figure 11:
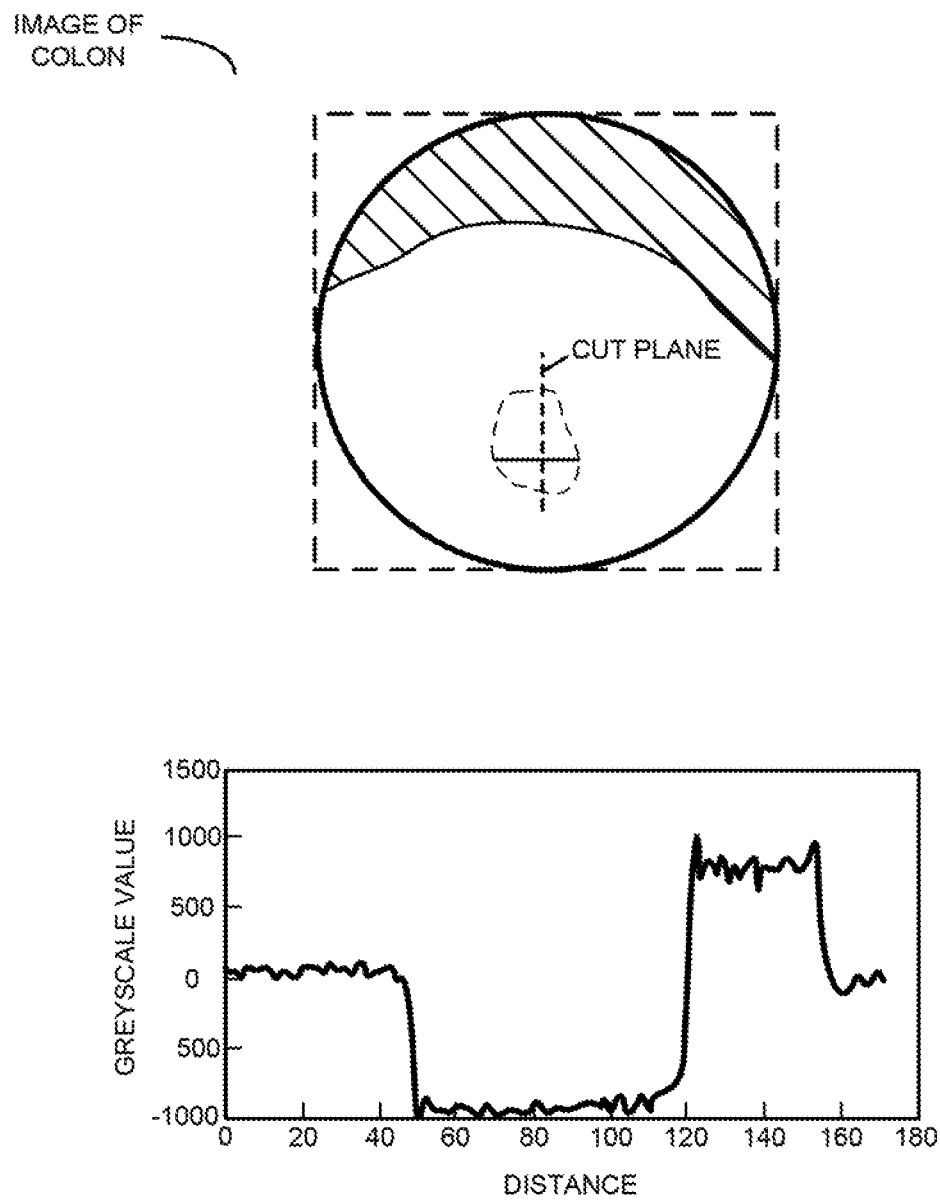

Because the greyscale distributions of air (tissue class $w_1$) and liquid (tissue class $w_2$) are usually very distinguishable and stable in different studies, they can be empirically learned by manually segmenting these two tissue classes in a given CT study, and then constructing the probability distribution functions $p(x_j, w_1)$ and $p(x_j, w_2)$ using kernel-density estimation. This is illustrated in FIG. 11, which presents a drawing illustrating segmentation of a colon in CTC (including, as described previously, defining values of $x_0$ and $\gamma$ for different tissue classes or pixel types along a cut plane through the colon). In particular, FIG. 11 depicts the 1D values of the cut plane going across the abdomen soft tissue, from the air-filled colon lumen to the contrast-filled colon lumen. The 1D values start around +50 (or close to zero) for soft tissue, drop down to near −1000 for air, rise sharply up to the contrast near ±1000, and then back to the soft-tissue value. In an exemplary embodiment, the tissue classes include: an air/$CO_2$-filled colon lumen (with $x_0$ equal to −1000 Hounsfield units and $\gamma$ equal to 50), a tag/contrast-filled colon lumen (with $x_0$ equal to 1000 Hounsfield units and $\gamma$ equal to 50), and edges (which are a weighed summation of air and contrast voxels with the aforementioned parameters). Table 3 provides pseudo-code for this calculation for CTC with 36 neighbor Mg voxels.

TABLE 3

```
For each voxel (x, y, z) do
    sum=0;
    for i = −1 to 1 do
        for j = −1 to 1 do
            for k = −1 to 1 do
                if j NOT EQUAL to 0 then
```

TABLE 3-continued

```
                {
                sum += P(w1j(x + i, y + j, z + k));
                sum += P(w2j(x + i, y + j, z + k));
                };
            end;
        end;
    end;
    P(w3j(x, y, z)) = sum/36;
end
```

In this case, each voxel looks at the neighboring voxels above and below its current y position, but not the voxels at its current y position. This focuses the segmentation calculation so that the air-contrast edge voxels can be determined to complete the colon lumen (i.e the calculation directs the segmentation neighborhood to follow the naturally pooled contrast which creates a horizontal edge between air and contrast).

More generally, the colon lumen is extracted using a technique that identifies CT image pixels as: air, contrast material, or pixels at the boundary of air and the contrast material. An accurate 3D model of the colon mucosa may be generated by resetting the greyscale values of the three identified pixel types to a greyscale value of −1,000 Hounsfield units and identifying the lumen-mucosa edge.

Figure 12:
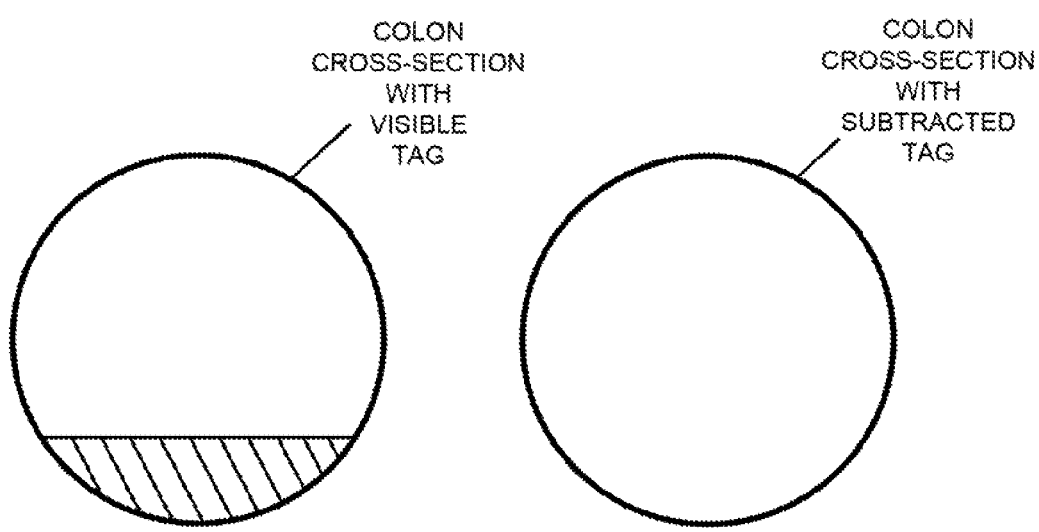
FIG. 12 is a drawing illustrating a digital subtraction bowel cleansing (DSBC) technique in accordance with an embodiment of the present disclosure.

Furthermore, during DSBC, a DSBC technique may identify the contrast material present in the colon. Because the segmentation technique explicitly identifies the contrast material as a tissue class, it can be aggregated and isolated as an independent volume mask. This volume mask can be subsequently used to subtract the contrast material areas from the image data. This is illustrated in FIG. 12, which presents a drawing illustrating a DSBC technique.

After Segmentation and DSBC, a centerline that runs through the length of the colon may be extracted. The centerline may be an approximation of the medial axis of the colon surface that is given in terms of its inner Voronoi diagram. In other words, the path C=C(s), where s is an arc length, traced from point $P_0$ to $P_1$ that minimizes:

$$L_{centerline}(C) = \int_{0=C^{-1}(P_0)}^{C^{-1}(P_1)} F(C(s))dS,$$

where F(x) is a scalar field that is smaller for points that are closer to the center of an object, and C is defined by the inner Voronoi diagram. Note that $$F(x) = \frac{1}{R(x)} \forall x \in Vor(P).$$

Figure 13:
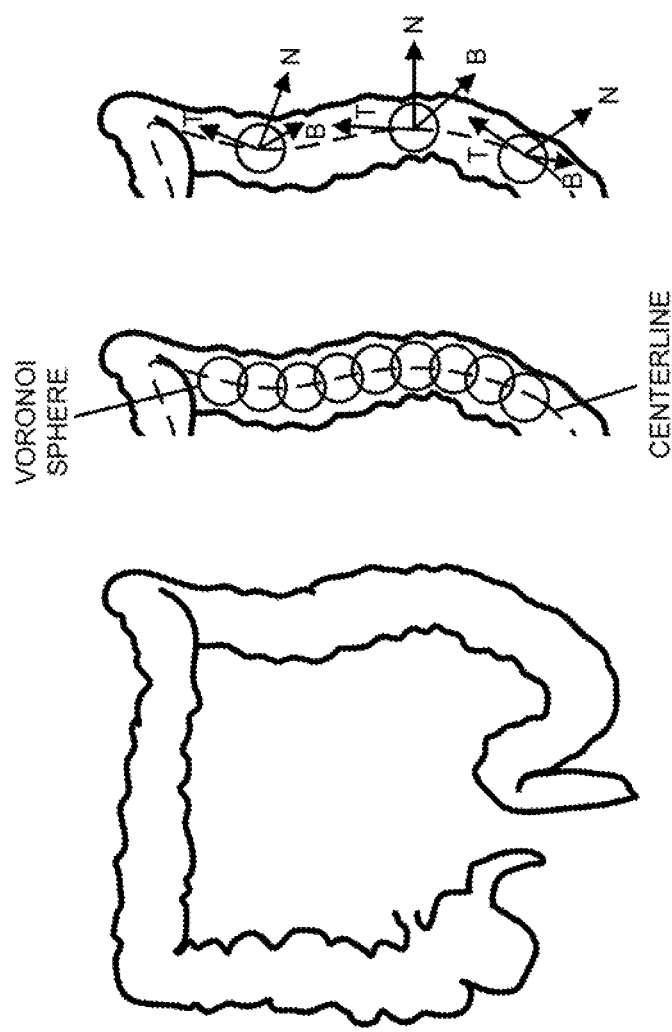
FIG. 13 is a drawing illustrating segmentation of a colon in accordance with an embodiment of the present disclosure.

F(x) can also be thought of as a centering potential, across a scalar field, where P is the point set sampling the surface, and R(x) is the scalar field defined on Voronoi diagram representing the values of the radius of the Voronoi spheres. As shown in FIG. 13, which presents a drawing illustrating segmentation of a colon, the values of the radius of the Voronoi spheres may be the maximal inscribed spheres with respect to the sampling point set P.

Note that there are many minimal path techniques that can be leveraged to extract a centerline. In general, a centerline path C(s) in a 3D image can be obtained by minimizing the energy $\Omega[0, L]$, where L is the length of the curve $$\int_\Omega \tilde{P}(C(s))ds.$$

Figure 14:
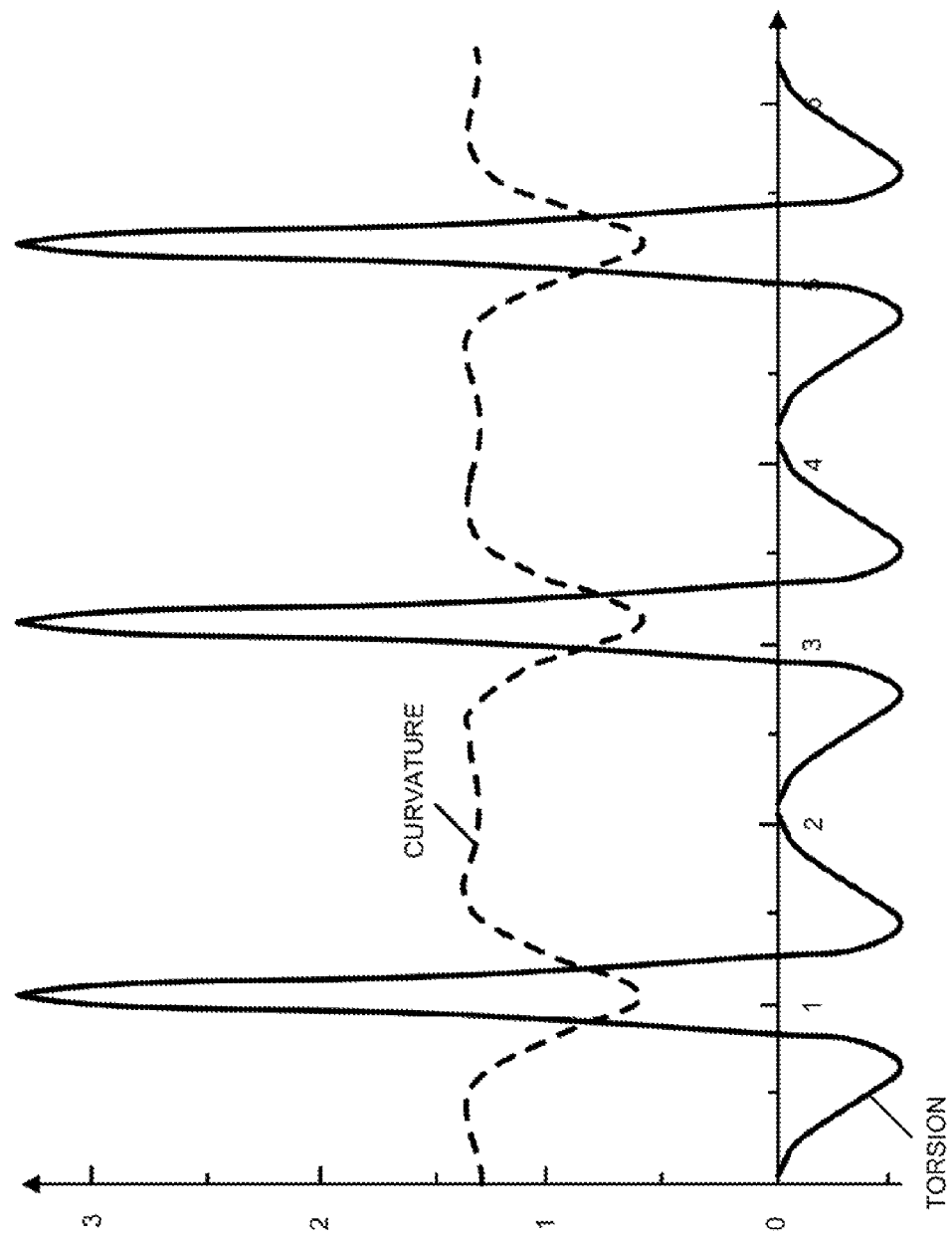
FIG. 14 is a drawing illustrating curvature analysis in accordance with an embodiment of the present disclosure.

Once a centerline has been extracted, a centerline curvature evaluation may be performed in order to identify points along the centerline that can define bounds of colon segments that have an approximate linear tubular shape. In some embodiments, kinematic properties at each point along a centerline are extracted using a Frenet-Serret (FS) formulation in particular, the FS formulation describes the derivatives of the so-called tangent, normal, and binormal unit vectors in terms of each other. The tangent, normal, and binormal unit vectors (which are often, respectively, called T, N, and B, or collectively the Frenet-Serret frame) together form an orthonormal basis spanning $R^3$. Note that T may be defined as the unit vector tangent to the curve, pointing in the direction of motion. Moreover, N may be defined as the normal unit vector (the derivative of T with respect to the arclength parameter a the curve) divided by its length. Furthermore, B may be defined as the binormal unit vector, i.e., the cross product of T and N. Mathematically, the Frenet-Serret frame may be expressed as $$\frac{dT}{ds} \kappa N$$
$$\frac{dN}{ds} = -\kappa T \ \tau B,$$
$$\frac{dB}{ds} \ - \tau N$$

when d/ds is the derivative with respect to arclength, $\kappa$ is the curvature and $\tau$ is the torsion of the curve. The two scalars $\kappa$ and $\tau$ may effectively define the curvature and torsion of a space curve. As illustrated in FIG. 14, which presents a thawing illustrating curvature analysis of a torus knot, intuitively curvature measures the failure of a curve to be a straight line, while torsion measures the failure of a curve to be planar. Note that T, N, B, $\kappa$, and $\tau$ are sometimes collectively referred to as the 'Frenet-Serret apparatus.'

Figure 15:
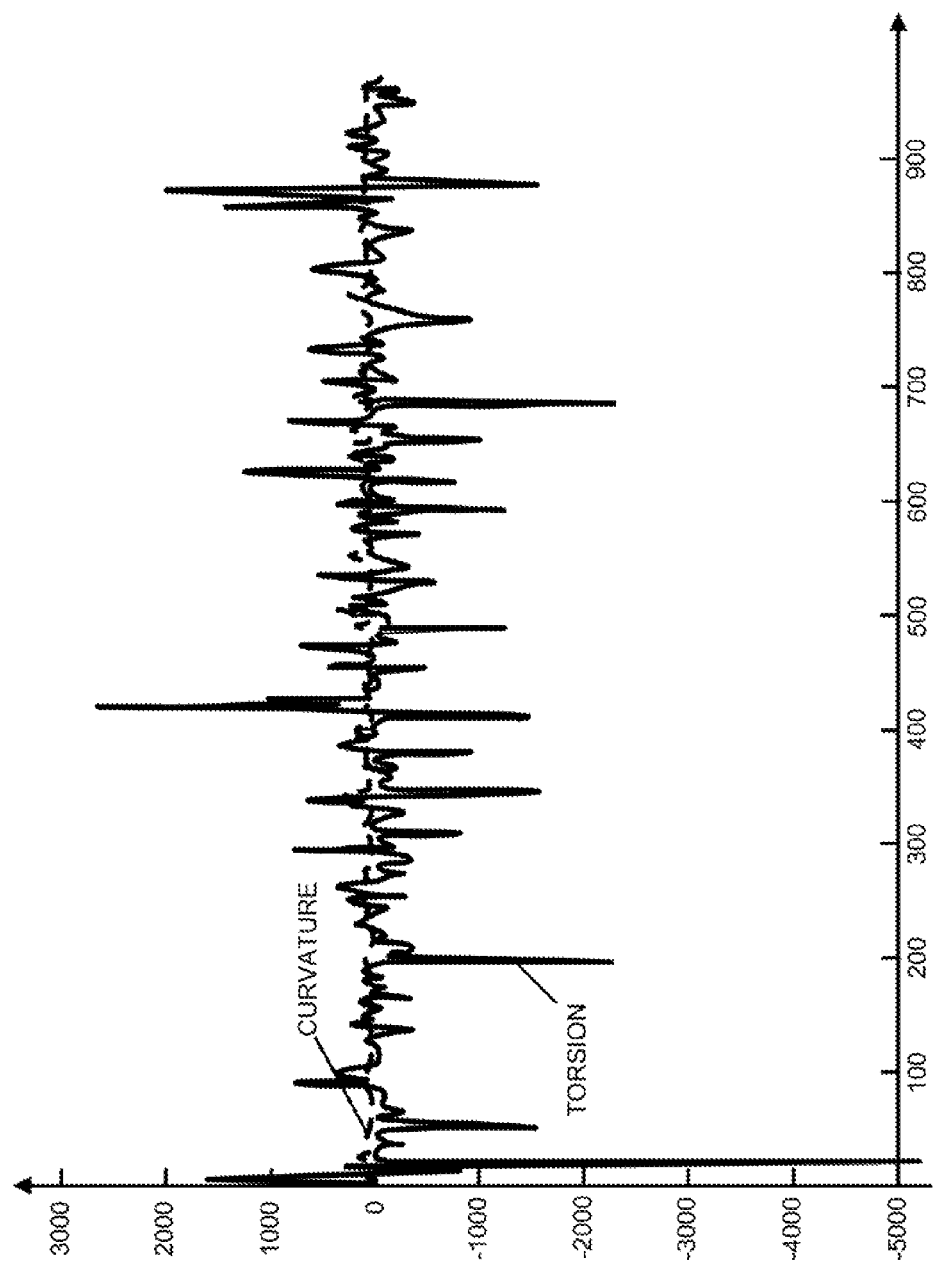
FIG. 15 is a drawing illustrating curvature and torsion during segmentation of a colon in accordance with an embodiment of the present disclosure.

The goat of evaluating the curvature of the colon is to identify points along the centerline that identify boundaries of approximate linear colon segments, which can be used as colon-centerline partition points. Data engine 110 (FIG. 1) may identify partition points along the centerline that have a local maximum curvature value. However, as illustrated in FIG. 15, which presents a drawing illustrating curvature and torsion during segmentation of a colon, because haustral folds create a 'push and pull' effect on the Voronoi and thus the centerline, curvature values can be very noisy, Therefore, in some embodiments a linear Gaussian filter with a large window (e.g., 50 units) and a large variance (e.g., 6.0) is applied to minimize the impact of haustral fold noise on the centerline Frenet-Serret frame.

Once the centerline is de-noised, data engine 110 (FIG. 1) may identify and store colon centerline-partition points m a centerline-partition list, such as a data structure in a computer-readable memory. In particular, in order to partition the colon into linear segments, the segmentation technique may, given a centerline and for any point on the centerline, define both a forward direction vector using this point, and its next neighbor point, and a backward direction vector using this point and its previous neighbor point as the segment extension direction. Then, local maximum curvature points along a de-noised centerline Frenet-Serrret frame may be identified. Moreover, the maximum radius around the local maximum curvature may be used to determine the segment partition points along the forward direction and backward direction (the tangent directions), which may be stored in the partition point list in sequence. If a new local maximum curvature point is identified and it is located at a distance greater than the stored maximum radius from the prior local maximum curvature point, the centerline segment may be added again to the centerline-partition list in the similar way described above until there are no more local maximum curvature points available. Furthermore, after evaluating, some or all the points in the centerline, the segments may be shortened to a predefined maximum length (such as 5-8 cm).

Alternatively, another technique for identifying and storing colon centerline-partition points in a centerline-partition list may, given a centerline and for any point on the centerline, define a forward direction vector using this point and its next neighbor point as the segment direction. Then, a function may be defined to calculate the longest segment that can satisfy the threshold criteria when some or all points are projected to the perpendicular plane defined by the segment direction as the normal. When some or all the points are processed, starting with the largest segment length (which may have a length value in real space unit such as meters), the points belonging to this segment may be labeled and then the rest of the centerline points not yet labeled may be processed. This operation may be repeated until no centerline point is left unlabeled. Moreover, when labeling overlaps with the existing labels, a segment neighborhood with high curvature values may be established and an extra segment may be inserted to cover the overlap at the boundary (such as 5-10% overlap). Furthermore, the label may be sorted when necessary because it was based on the segment length rather than sequence. Additionally, after evaluating some or all the points in the centerline, the segments may be shortened to a predefined maximum length (such as 5-8 cm). Note that other techniques for recognizing partition points along the centerline can be used such as local curvature scale (c-scale) measurements (which provides an alternate technique than Frenet-Serret analysis to determine a centerline and colon partition or segmentation points based on its curvature shape signatures, boundary moments, polygonal and curve decomposition, syntactic analysis, scale-space analysis, a spectral transform (e.g., Fourier descriptors and wavelet descriptors), and/or defining shape invariants using boundary primitives.

We now further describe the local curvature-scale technique. A local curvature scale segment (c-scale segment) at any point b along a centerline B is the largest connected set of points of 8 connected to b such that no point in that set is farther than i from a line connecting the two end points of the connected set of points. In this manner, 'homogeneity of region' is expressed in terms of 'straightness' at every point.

Figure 16:
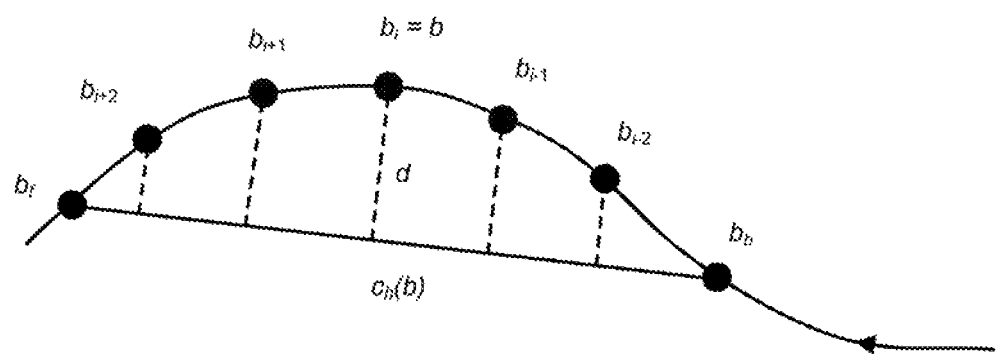
FIG. 16 is a drawing illustrating a curvature-scale segment in accordance with an embodiment of the present disclosure.

Let $b_1, \ldots, b_n$ be the points or bels) defining a bound. Each point b equal to $b_i$ may be associated with its $c_f$ scale segment C(b). This set may be an indirect indicator of the curvature at h. In order to determine $C(b_i)$, progressively examine the neighbors of this point, first the set of points $b_i-2, h_i, b_i+2$, then the set $b_i-3, b_i-2, b_i, b_i+2, b_i+3$, and so on as shown in FIG. 16, which presents a drawing illustrating a curvature-scale segment 1600). At each examination, calculate the distance of the points in the set from the straight line connecting the two end points of the set. If the maximum distance of these points from the line is greater than a threshold t, define the c-scale segment C(b) of b as the last set of connected points found for which the distance was still within the threshold. The e-scale value assigned to b, (which is denoted $C_h(b)$) is the chord length corresponding to C(b), which is the length of the straight-line segment between the end points $b_b$ and $b_f$ of C(b).

If $G_h(b)$ is large, it may indicate small curvature at b, and if it is small it may indicate high curvature. c-scale values may be helpful in estimating actual segments and their curvature, independent of digital effects.

Figure 17:
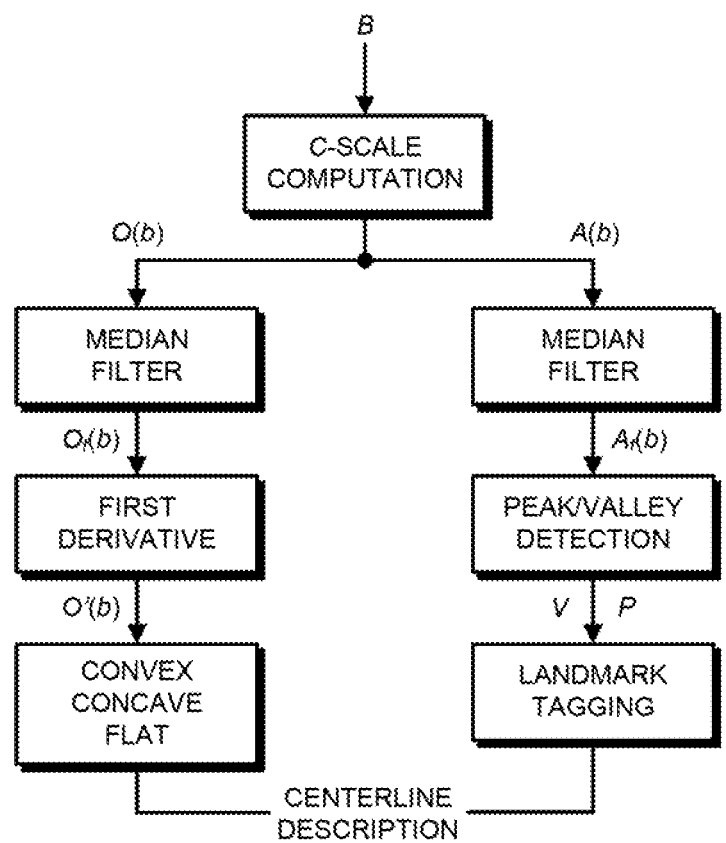
FIG. 17 is a flow chart illustrating a local curvature-scale technique in accordance with an embodiment of the present disclosure.

Given a (digital) centerline B and a scale parameter t, the goal is to obtain a partition PB of B into segments, a set $s_L$ of landmarks or characteristic dominant points), and a shape description assigned to every element of PB. This is summarized in FIG. 17, which presents a flow chart illustrating a local curvature-scale technique 1700. In FIG. 17, O(b) is the orientation at point h of the centerline B, A(b) is the arc length at point b of the centerline B, $O_f(b)$ is the smoothed orientation, $A_f(b)$ is the smoothed arc length, O'(b) is the first derivative of the smoothed orientation. P are the peak landmarks and V are the valley landmarks. This local curvature-scale technique may be performed by a computer system (such as computer system 600 in FIG. 6).

At each point b of B, the computer system may determine the c-scale value $C_h(b)$ from which the arc length A(b) may be estimated using $$A(b) = \frac{\tan^{-1}\left(\frac{C_h(b)}{2 \cdot (r-s)}\right) \cdot \pi \cdot r}{90}.$$

Figure 18:
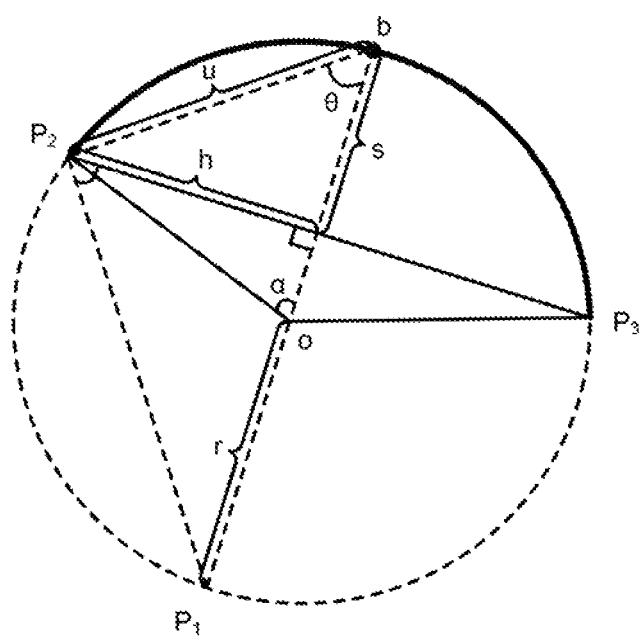
FIG. 18 is a drawing, illustrating calculations in the local curvature-scale technique of FIG. 17 in accordance with an embodiment of the present disclosure.

As shown in FIG. 18, which presents a drawing illustrating calculations in local curvature-scale technique 1700 (FIG. 17).

$$\tan(\alpha) = \frac{C_h(b)}{2 \cdot (r-2)}$$

and $$A(B) = \frac{\pi \cdot r \cdot \alpha}{90}.$$

Figure 19:
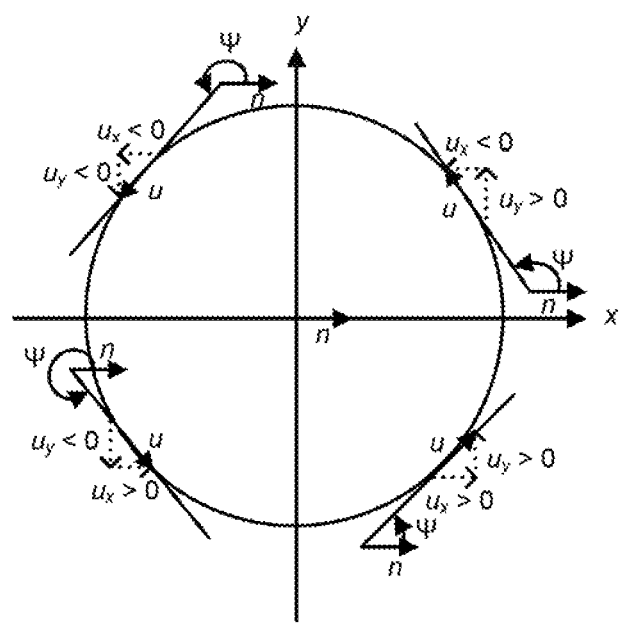
FIG. 19 is a drawing illustrating calculations in the local curvature-scale technique of FIG. 17 in accordance with an embodiment of the present disclosure.

Moreover, as shown in FIG. 19, which presents a drawing illustrating calculations in local curvature-scale technique 1700 (FIG. 17), the orientation O(b) may be obtained using, O(b) equal to $\psi(b)$ minus $\psi(b_1)$. Note that $\psi(b)$ equals $360 - \cos^{-3}(\mu_x(b))$ if $\mu_y$ is less than zero, and $\psi(b)$ equals $\cos^{-1}(\mu_x(b))$ if $\mu_y$ is greater than or equal to zero.

Then, the computer system may smooth A(b) and O(b) using a median filter of width 2w+1 centered at every element b, where w is the half width of the window used for filtering (which may be specified in terms of the number of points considered on either side of h). The computer system may repeat this process k times to get a smoothed version of A(b), called $A_f(b)$.

This operation may automatically detect the peaks and the valleys of $A_f(b)$ by using mathematical morphology. In particular, the peaks may correspond to straight line segments in the boundary and the valleys may correspond to curved segments. Note that the mathematical morphology may be based on set theory and may provide powerful tools for image analysis. The fundamental operations (or transformations) may include erosion, dilation, opening and closing. An opening operation may include an erosion operation followed by a dilation operation. Moreover, a closing operation may include a dilation operation followed by an erosion operation.

Figure 20:
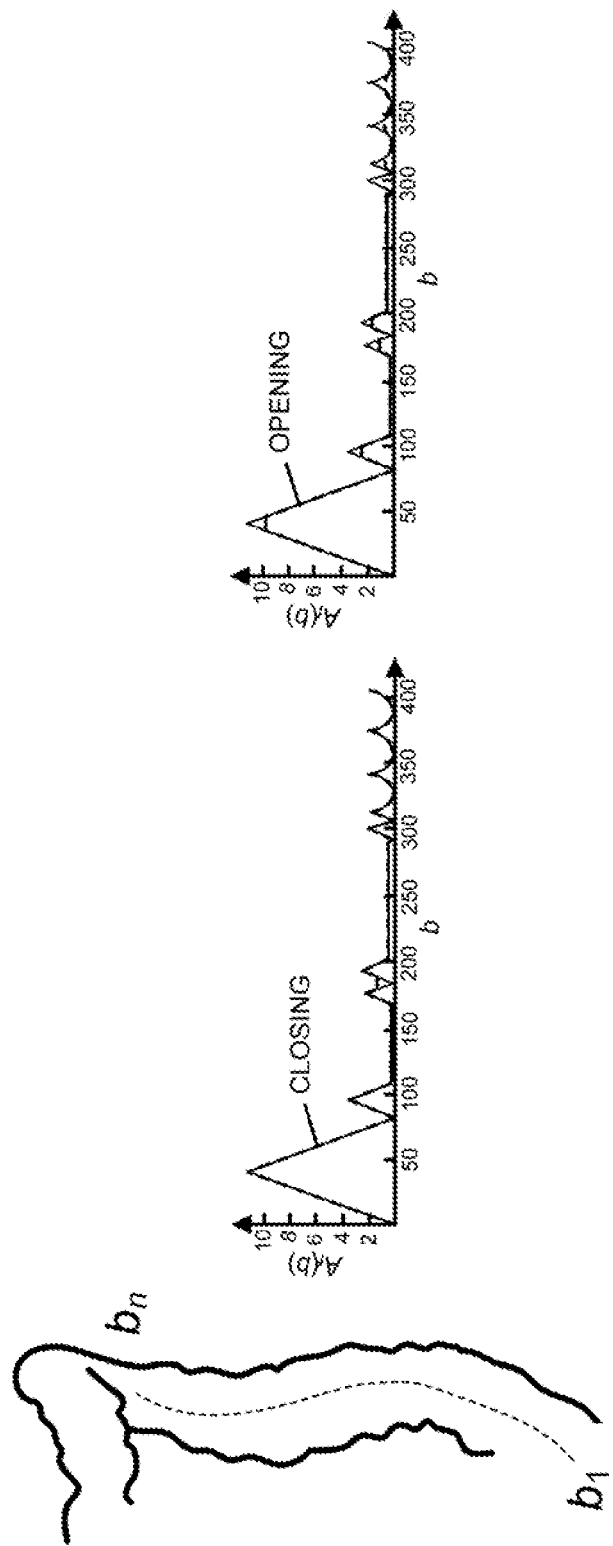
FIG. 20 is a drawing illustrating opening and closing operations to detect peaks and valleys along an arc length in the local curvature-scale technique of FIG. 17 in accordance with an embodiment of the present disclosure.

A structuring element may define the size and shape of the transformation to be done. For example, a structuring element of size se may be applied to the signal $A_f(b)$. As shown in FIG. 20, which presents a drawing illustrating opening and closing operations in local curvature-scale technique 1700 (FIG. 17), the opening and closing operations may be used to detect the peaks and the valleys of $A_f(b)$.

In particular to find the valleys, the computer system may apply to $A_f(b)$ a bottom-hat filtering operation, which is the difference between $A_f(b)$ and its closing. This filter may extract the valleys of $A_f(b)$. Once the computer system has detected the valleys in $A_f(b)$, the computer system finds the minimum value for each valley detected. These local, minima may correspond to the valleys in $A_f(b)$ and may represent points with high curvature in H. Similarly, in order to find the peaks, the computer system may apply a top-hat filtering operation which is the difference between $A_f(b)$ and its opening. This may extract the peaks of $A_f(b)$. These maxima may correspond to the peaks in $A_f(b)$, which are the middle points of the straight segments in B.

By selecting a different size ($se_v$ and $se_p$) for the structuring elements, the computer system can vary the number of valleys and peaks detected. In particular, the computer system may select θp to control the size of the detected peaks, and may select θv to control the size of the detected valleys. For example, in FIG. 20 the computer system may use a structuring element of size five for both valley and peak detection. Thus, by specifying $\theta_v$ and $\theta_p$ the computer system did not need to select elements. In this way, the computer system can avoid spacious valleys and peaks, or can select the most prominent valleys or peaks.

Figure 21:
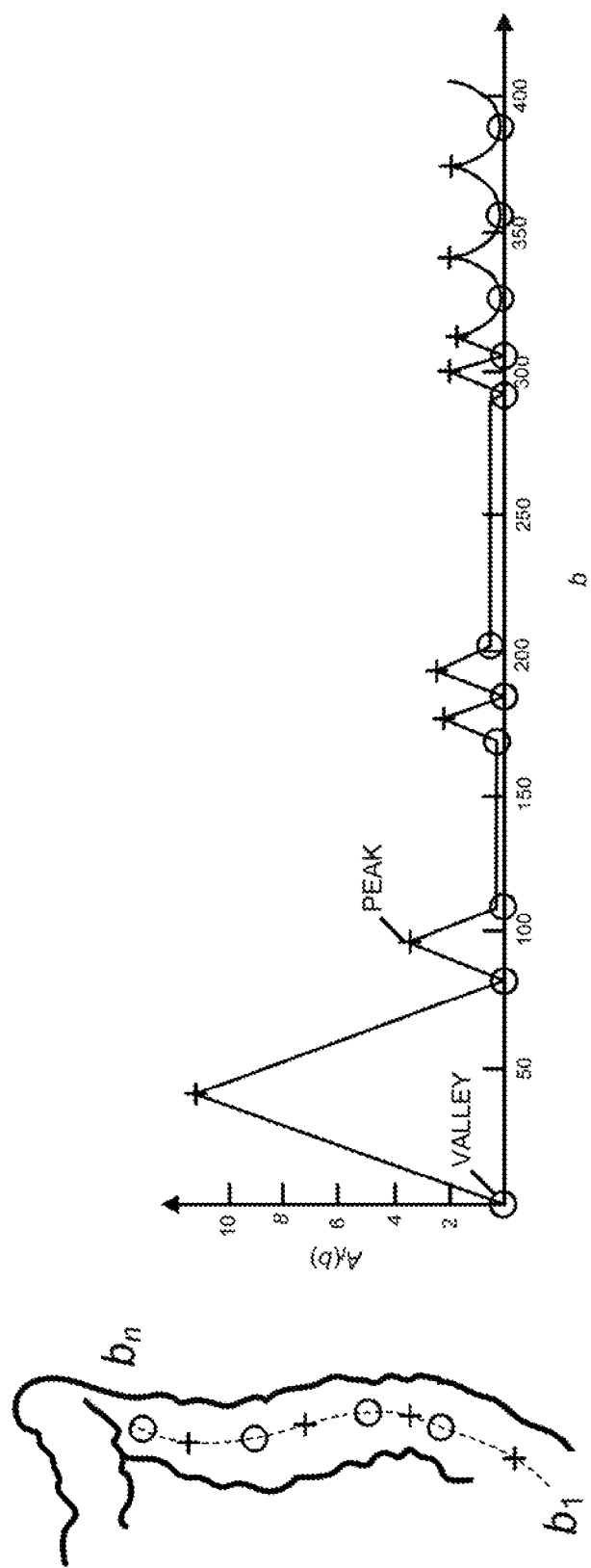
FIG. 21 is a drawing illustrating detected peaks and valleys along the arc length in the local curvature-scale technique of FIG. 17 in accordance with an embodiment of the present disclosure.
Figure 22:
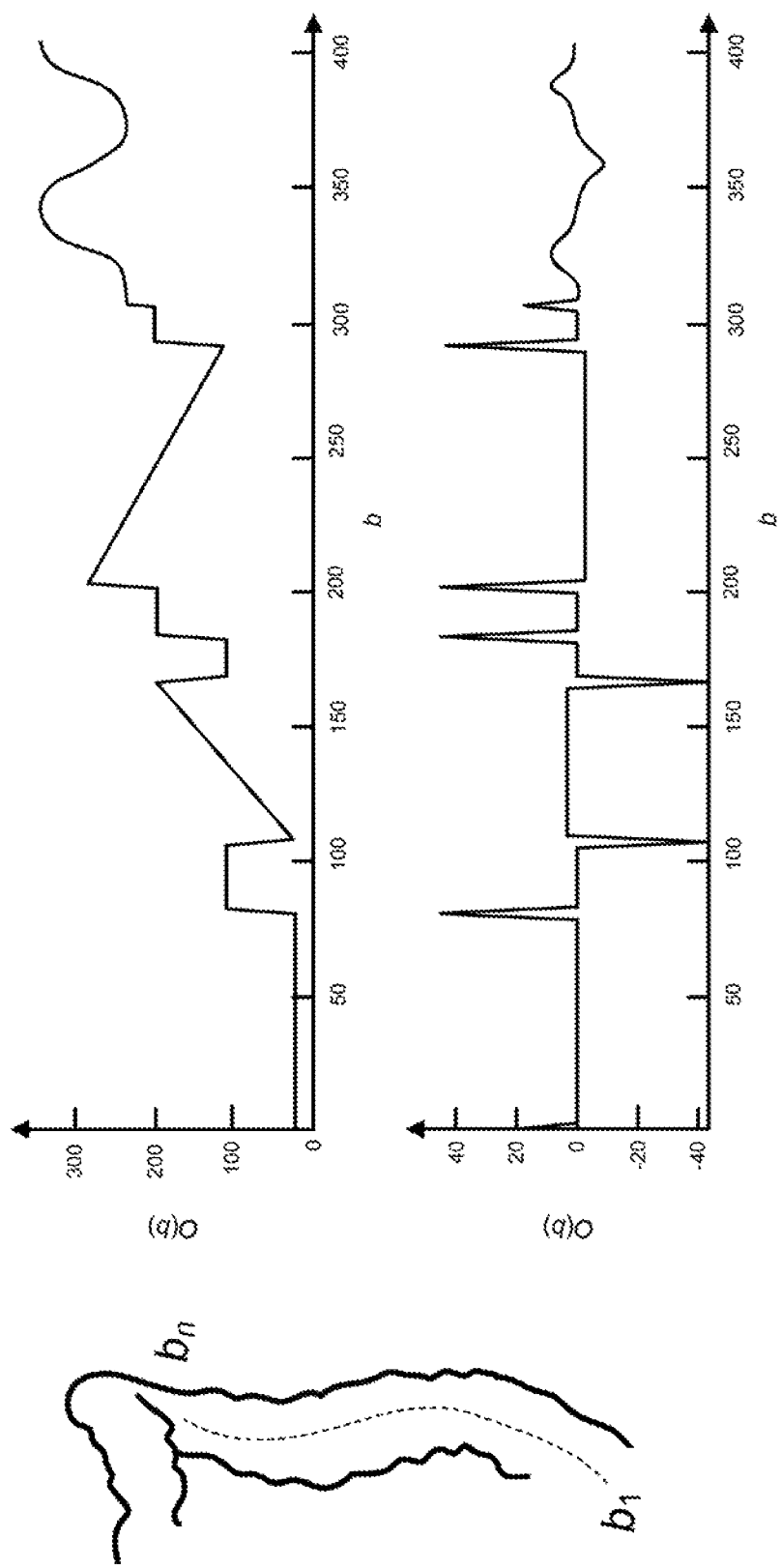
FIG. 22 is a drawing illustrating landmarks along a boundary in the local curvature-scale technique of FIG. 17 in accordance with an embodiment of the present disclosure.

As shown in FIG. 21, which presents a drawing, illustrating detected peaks and valleys along the arc length in local curvature-scale technique 1700 (FIG. 17), after the bottom-hat and the top-hat filtering operation, the computer system detects the peaks and valleys, Once the computer system has detected the peaks P and the valleys V in $A_f(b)$, he computer system can locate the landmarks $s_L$ on the boundary in FIG. 21 by identifying the points where local minima/maxima occurred. Then, as shown in FIG. 22, which presents a drawing illustrating landmarks along a boundary m local curvature-scale technique 1700 (FIG. 17), from O'(b) the computer system can extract a complete description of each bel in B. Note that in the centerline description, local positive maxima may correspond to convex corners, local negative maxima may correspond to concave corners, constant zero curvature may correspond to straight line segments, constant non-zero curvature may correspond to circular segments, and zero crossings may correspond to inflection points.

Once the centerline points have been labeled as colon segment partition points, they ma be grouped into colon segment proximal (S) and distal (D) points so that colon surface points can be matched to partitioned centerline segments, in particular, each colon segment may be composed by a pair of centerline partition points, where colon segment 1 is defined by point $S_1$ and point $D_1$, colon segment 2 is defined by point $S_2$ and point $D_2$, and $D_1$ equals $S_1$. Then, each point of the 3D colon surface model resulting from the segmentation may be associated to a particular colon segment.

One technique for associating colon points to a corresponding colon segment is for the colon segment to be enclosed by a bounding box that is aligned with the vector connecting the proximal S and the distal D points of the centerline of the colon segment. In order to approximate the geometry of a colon segment, the shape of the bounding boxes may be kept thin (such as an aspect ratio less than 0.25 or 0.3) and may be iteratively subdivided to generate an articulated object model that fits the tortuosity of the patient's colon.

Figure 23:
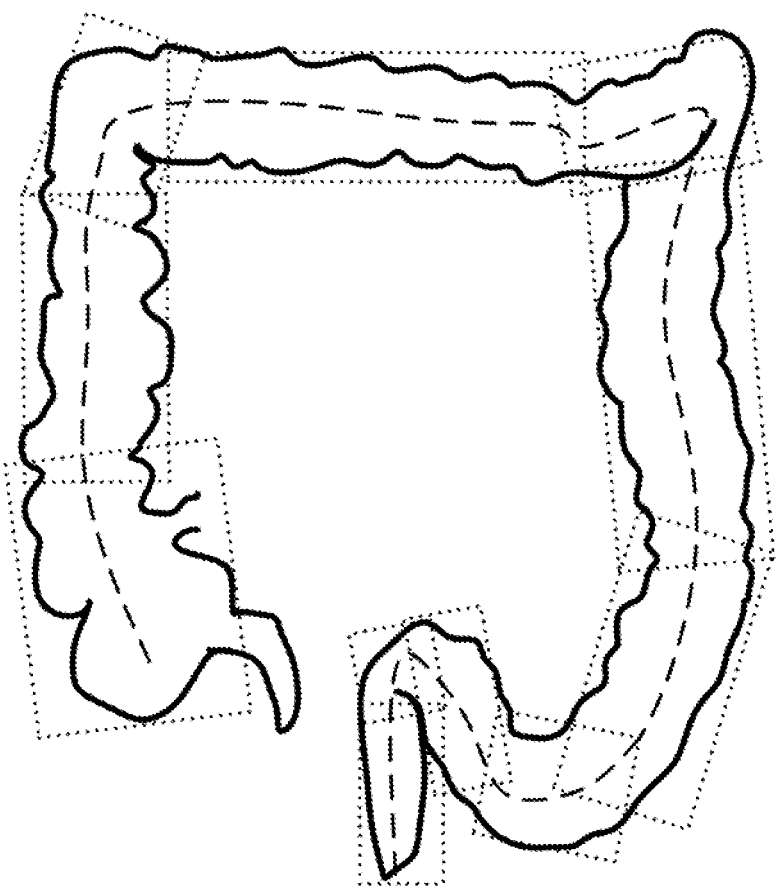
FIG. 23 is a drawing illustrating segmentation of a colon in accordance with an embodiment of the present disclosure.

As illustrated in FIG. 23, which presents segmentation of a colon in CTC, the colon may be divided into at least six standard segments (e.g., the rectum, the sigmoid, the descending colon, the transverse colon, the ascending colon and the cecum). These colon segments may be included in a list of 3D clinical objects of the clinical anatomy (which may be stored in a data structure in a computer-readable memory) for use by graphics engine 112 (FIG. 11).

Another technique for associating colon point to a corresponding colon segment is to leverage the point coordinates of the centerline and the 3D colon surface model. In particular, for each colon point Pc, the closest centerline point Pctln may be identified. Then, the line of sight between Pc and Pctln is evaluated, so that there are no other points between them, by tracing a straight line between Pc and Pctln. If there is a clear line of sight, then Pc may be associated to the colon segment corresponding to Pctln. However, if there is no clear line of sight, then do not associate Pc to any colon segment. Moreover, the remaining colon points Pc that have not been associated to a colon segment may be associated to colon segment corresponding to then nearest neighbor. The result may be a patient-specific colon articulated model that is automatically generated and can be edited by the reader. The colon articulated model may enable the colon segment navigation methodology of the True 3D-CTC protocol.

After data engine 110 (FIG. 1) creates the clinical objects (the colon image data, the colon segmentation, the centerline and/or the colon partitions), graphics engine 112 and tool engine 118 may perform methodologies that provide different ways to interrogate supine, prone and decubitus image data. Note that the image data can be presented as a 3D colon surface model, a volume, and/or a 2D multi-planar (2D MPR) reformatted image.

Figure 24:
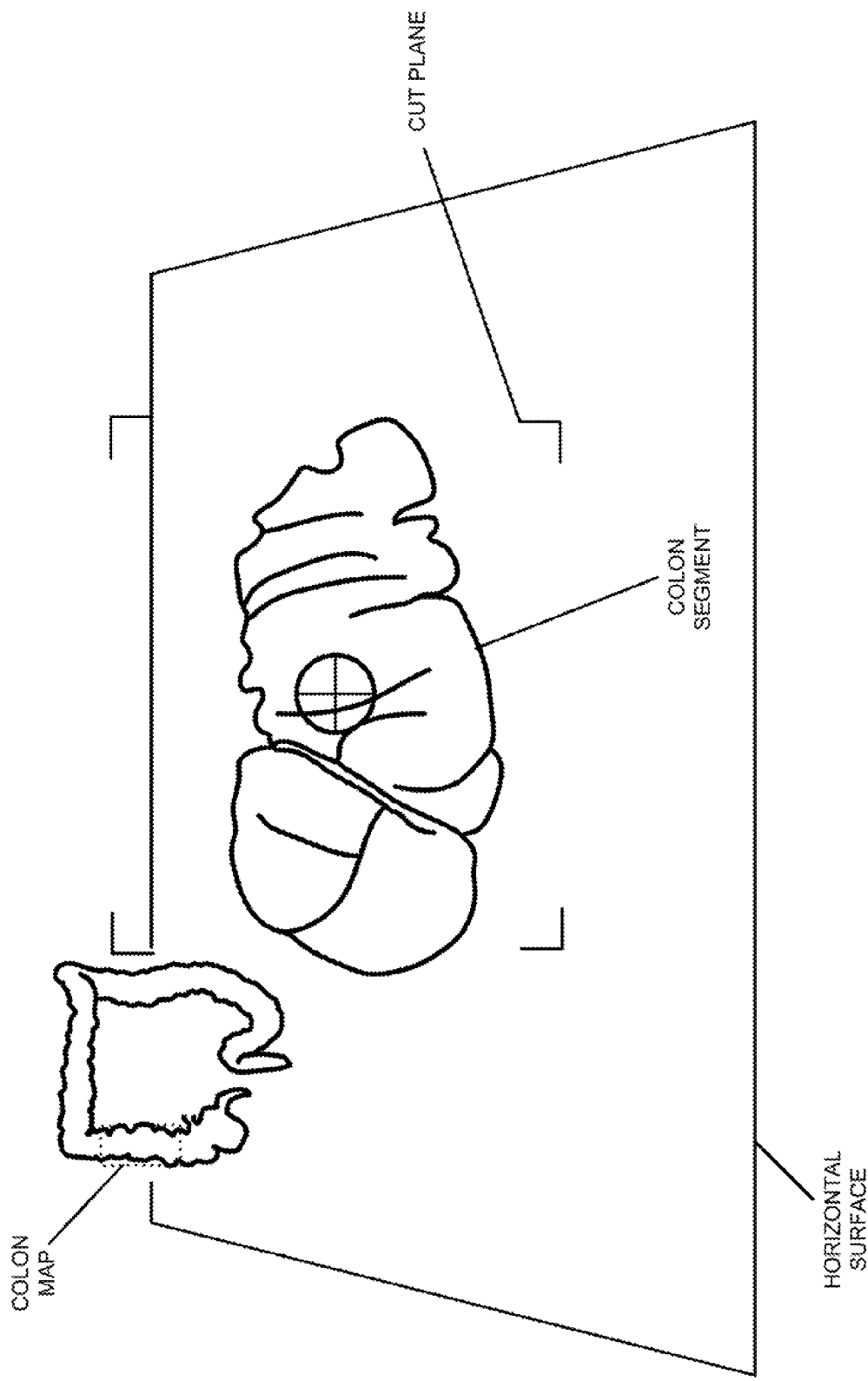
FIG. 24 is a drawing illustrating colon navigation in accordance with an embodiment of the present disclosure.

As shown in FIG. 24, which presents a drawing illustrating colon navigation, graphics engine 112 and tool engine 118 may allow a reader to select one or more protocol methodologies by combining different virtual instruments to the clinical objects being displayed. For example, the one or more protocol methodologies may include: a colon-segment-based navigation methodology as a primary navigation technique that facilitates polyp search via a 3D view of colon segments with a cut plane; a problem-solving methodology that provides a combined 2D and 3D view to reduce false-positive readings (i.e., to correctly identify true polyps); a dual-view methodology for comparing different patient position image data; and/or a general image-review methodology. While the following discussion uses reader-based navigation, polyp identification and evaluation, in some embodiments graphics engine 112 and tool engine 118 provides detailed polyp evaluation (the clinical targets) using established criteria to identify and evaluate true polyps. For example, a high sensitivity and low false-positive rate computer-aided-diagnosis (CAD) technique may be used to: bookmark polyp candidates by searching through the colon lumen; evaluating if a particular part of the wall is shaped like a polyp (e.g., based on geometric features); and if its neighboring tissue is smooth (e.g., based on texture features).

Note that the reader can change between any of the provided protocol methodologies at any time during his review. Thus, any bookmarks or measurements made in any protocol methodology may he spatially registered in any of the other visualization methodologies.

When the colon-segment-based navigation methodology is engaged, the reader or viewer may select a stereoscopic-acuity-scaled colon segment, which may then be displayed horizontally across its long axis or centerline. As shown in FIG. 24, a cut plane may be positioned at the middle point of the colon-segment centerline and a reference colon that highlights the colon segment that is currently under review may be displayed.

The colon segment may be rotated on its long axis to bring the rest of the lumen into view. Moreover, the colon may be a surface, a volume region of interest corresponding to the colon segment and/or a registered surface-volume combination. Note that the DSBC mask may be applied to the volume data to subtract any contrast material on the fly. Furthermore, note that by providing an undistorted view of the colon lumen, polyps may become more conspicuous.

In some embodiments, the cut plane is elevated or offset from the mid-point of the colon segment centerline so as to show more of the colon lumen as the colon segment rotates. This elevation or offset may be: controlled or specified by the reader; pre-specified as a user preference; and/or, as shown in FIG. 25 (which presents a drawing illustrating cut-plane placement), automatically set to increase the visible arc length of the colon lumen ($P_2$–$P_0$–$P_1$–$P_3$) by setting the cut plane at the mid-point of the colon segment centerline at point D. In some embodiments, the location of point D is a quarter of the radius of the colon above the mid-point of the centerline (point O), or D is defined by the distance BD, where BD is the difference between the maximum diameter and the minimum diameter of the colon segment along the centerline (which ma approximate the radius variation that results from haustral folds across the colon segment). Note that, by elevating or offsetting the cut plane from the centerline, the rotation needed to visualize all of the colon lumen may be minimized, which may reduce CTC interpretation time.

This can be illustrated by calculating the visible lumen area of a colon segment cross section that approximates a circle. The total area $A_T$ of a circle is equal to $\pi r^2$. However, for the case of a circle that is bisected by a straight line that the cut plane creates by running through points $P_2$–D–$P_3$, two sections of the circle may be defined but only one is visible (area Ab), while the other section is clipped by the cut plane and is not visible (area Aa). Note that areas Aa and Ab include the visible lumen. This establishes a larger visible lumen area from the start of the colon-segment evaluation during navigation. The total initial visible lumen area is given by $$A_T = \pi r^2,$$

and $$A_a = \frac{r^2}{2} \cdot \left(\frac{2\pi\alpha}{180} - \sin 2\alpha\right).$$

If $A_T$ equals $A_a$ plus $A_b$, then $$A_a = \pi r^2 - \frac{r^2}{2} \cdot \left(\frac{2\pi\alpha}{180} - \sin 2\alpha\right).$$

Figure 26:
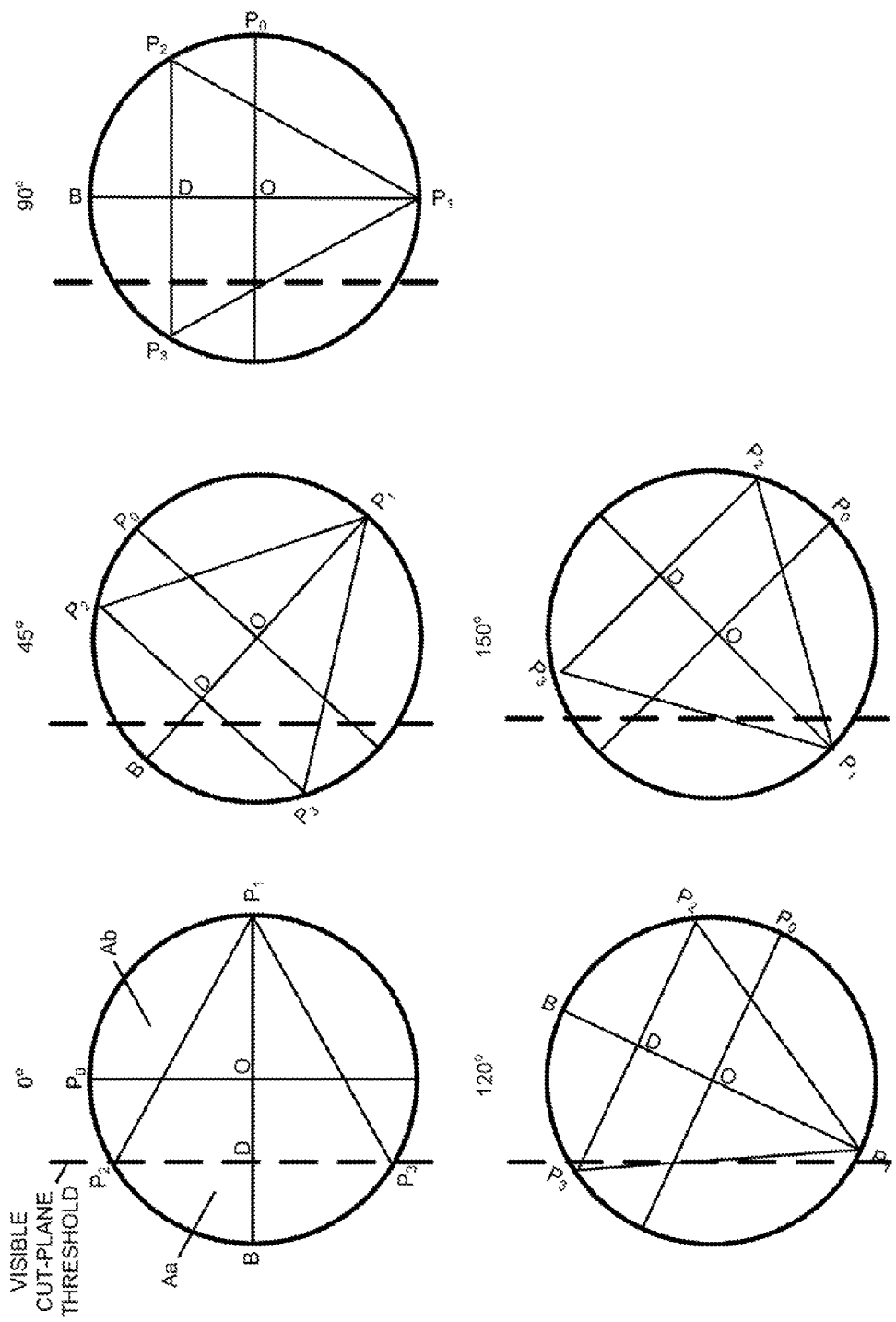
FIG. 26 is a drawing illustrating different rotated views of a cut plane in accordance with an embodiment of the present disclosure.

Furthermore, as shown in FIG. 26, which presents different rotated views of the colon (including 45°, 90°, 120° and 150°), it may take about 150° of rotation or about 40% of a full rotation to bring the Area Aa into complete view within the colon segment during navigation. Note that by using the pre-specified distance from the centerline, the amount of rotation needed to hung Area Aa into complete view may be significantly reduced, Table 4 presents values of the pre-specified distance from the centerline (D) in different segments of the colon using the geometry shown in FIG. 25.

TABLE 4

| | Segment Number | P1-D (mm) | P1-B (mm) | Ratio |
|---|---|---|---|---|
| Cecum | 17 | 38.42 | 59.29 | 0.648001 |
| Ascending | 16 | 41.4 | 53.5 | 0.773832 |
| Ascending | 15 | 33.84 | 56.63 | 0.597563 |
| Hepatic Flexure | 14 | 33.87 | 45.31 | 0.747517 |
| Transverse | 13 | 26.81 | 41.32 | 0.648838 |
| Transverse | 12 | 30.42 | 44.23 | 0.687768 |
| Transverse | 11 | 21.98 | 38.79 | 0.566641 |
| Splenic Flexure | 10 | 25.09 | 37.08 | 0.676645 |
| Descending | 9 | 27.61 | 43.54 | 0.63413 |
| Descending | 8 | 23.55 | 35.69 | 0.659849 |
| Descending | 7 | 17.41 | 31.13 | 0.559268 |
| Sigmoid | 6 | 12.18 | 19 | 0.641053 |
| Sigmoid | 5 | 15.18 | 24.68 | 0.615073 |
| Sigmoid | 4 | 16.41 | 26.25 | 0.625143 |
| Sigmoid | 3 | 17.83 | 27.93 | 0.638382 |
| Sigmoid | 2 | 17.36 | 28.64 | 0.606145 |
| Rectum | 1 | 22.36 | 31.34 | 0.713465 |

Figure 27:
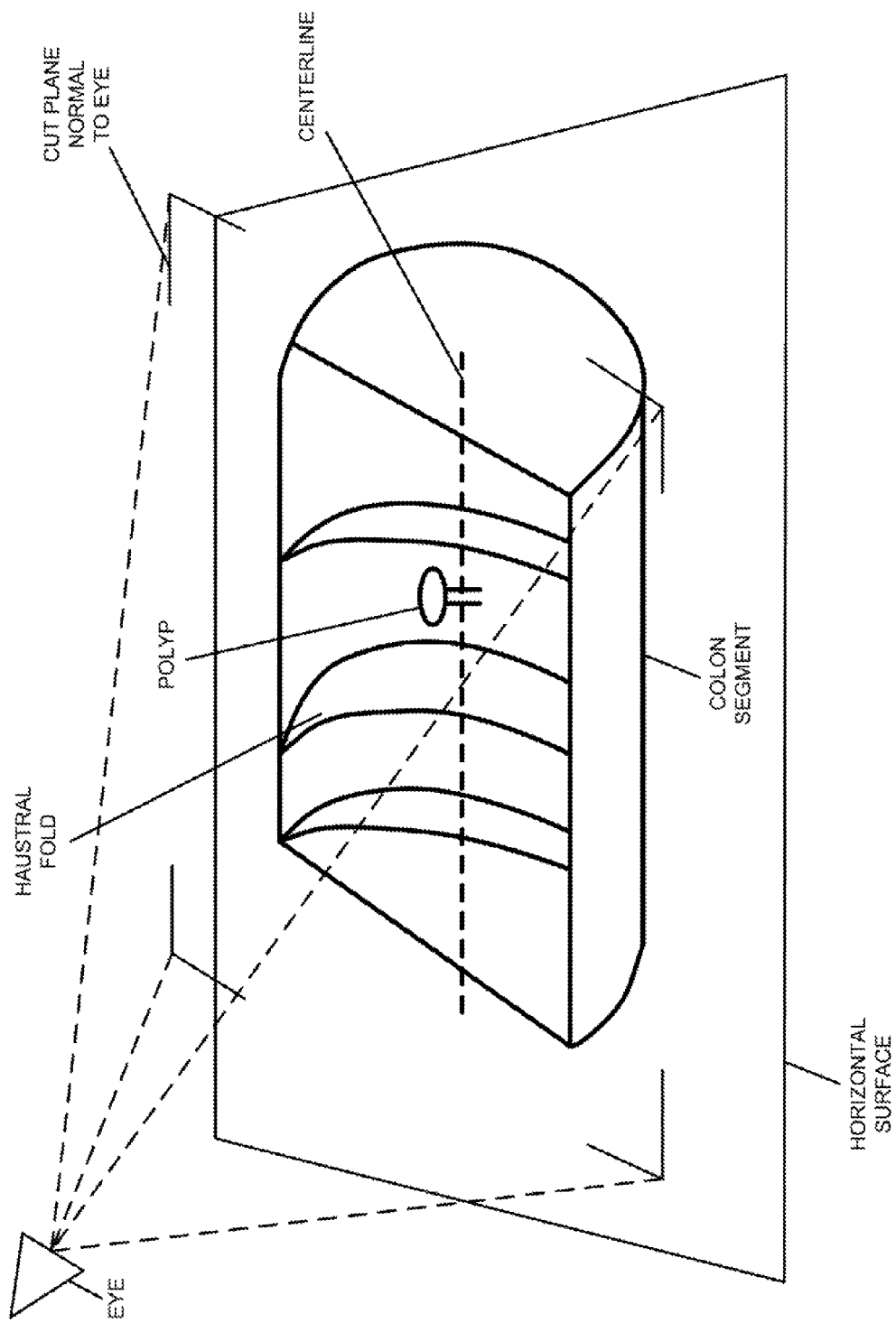
FIG. 27 is a drawing illustrating colon-segment navigation in accordance with an embodiment of the present disclosure.

Because the colon is a very tortuous organ, it is often very difficult to extract ideal linear colon segments. As shown in FIG. 27, which presents a drawing illustrating colon-segment navigation, in order to compensate the non-linearity of colon segments, the cut plane may be controlled by the readers head movement so that it is always normal to the reader's head position and orientation.

Moreover, with the hand-directed stylus, the reader may move the cm plane to visualize half or more of the colon-segment lumen and may rotate the colon segment in a different direction than on its long axis to bring obstructed area of the lumen into view. Furthermore, the reader may move on to another colon segment by activating or clicking on a displayed next or previous button or icon.

If the reader is navigating and visualizing the surface-volume combination and has not subtracted the DSBC mask, he may be able determine on the fly which candidate polyps base a highest likelihood to be flue polyps. This is because a cross-section of a true polyp may be displayed as the colon rotates through the cut plane and homogeneous soft tissue density values may be clearly visible, whereas false positive candidate polyps may have inhomogeneous density values or may have visible residue adhered contrast material.

Figure 28:
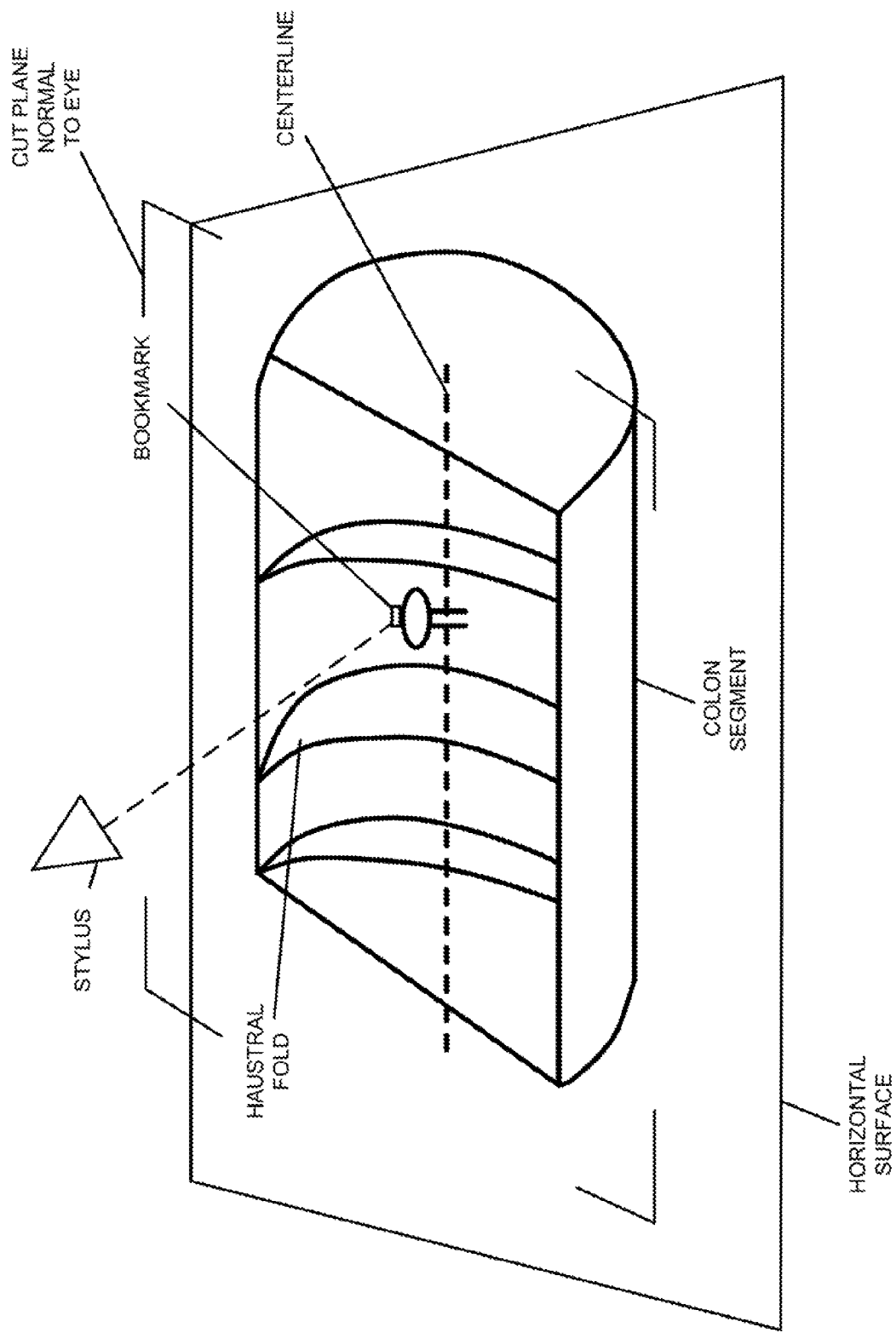
FIG. 28 is a drawing illustrating bookmarking in accordance with an embodiment of the present disclosure.

Furthermore, using the hand-directed stylus, the reader may bookmark a candidate polyp by pointing with the stylus and clicking on a suspicious lesion. This is shown in FIG. 28, which presents a drawing illustrating book-marking. When a bookmark is created, the bookmark may include the image-data indexes (such as the column, row and image-slice number), the colon surface cell number and/or its normal vector.

The problem-solving methodology may be used to assess tissue-density homogeneity with morphologic features. When the problem-solving methodology is engaged after placing a bookmark, the reader may see a 2D MPR image aligned to the surface of the display plane so that a normal to the 2D MPR image is parallel to a normal of the display. The 2D MPR image may have a cross-section of the bookmarked candidate polyp for the reader to evaluate. The reader may ad hist the window width and window level of the 2D MPR image, rotate and/or translate the image cross-section around the bookmark position.

If no bookmark has been placed on a colon segment, the reader may evaluate a polyp candidate using a combined 2D and 3D view. Using the hand-directed stylus, the reader may interact with a 2D image projection (such as axial and multi-planar reformatted images) or cross-section over a 3D view (such as a volume rendered image) of a potential or candidate polyp or colon segment (with a translucent or transparent surface) to uncover underlying tissue density and neighboring anatomy.

Note that during the detailed polyp evaluation, characteristics of a true poly may be used to confirm candidate polys. Typical characteristics of a true polyp may include: a spherical or hemispherical morphology, smooth borders without angulation, and/for a fixed position for sessile polyps and flat lesions. Polyps may also be correlated with homogeneous soft-tissue density in a 2D image cross-section when viewed using the problem-solving virtual instrument. Additionally, as described further below with reference to FIGS. 33 and 34, the reader can integrate lesion motion using correlate supine and prone views, and can focus on polyp candidates using region-of-interest magnification and window-level control.

During annotation or measurements, the problem-solving methodology may receive information specifying annotation markers in the 2D plane, where the annotation markers may specify the location, orientation, direction and/or size of the anatomical structure (i.e., measurements). After the annotation is complete, graphical system 100 (FIG. 1) may translate and rotate the 3D image back to the initial position and orientation.

Figure 29:
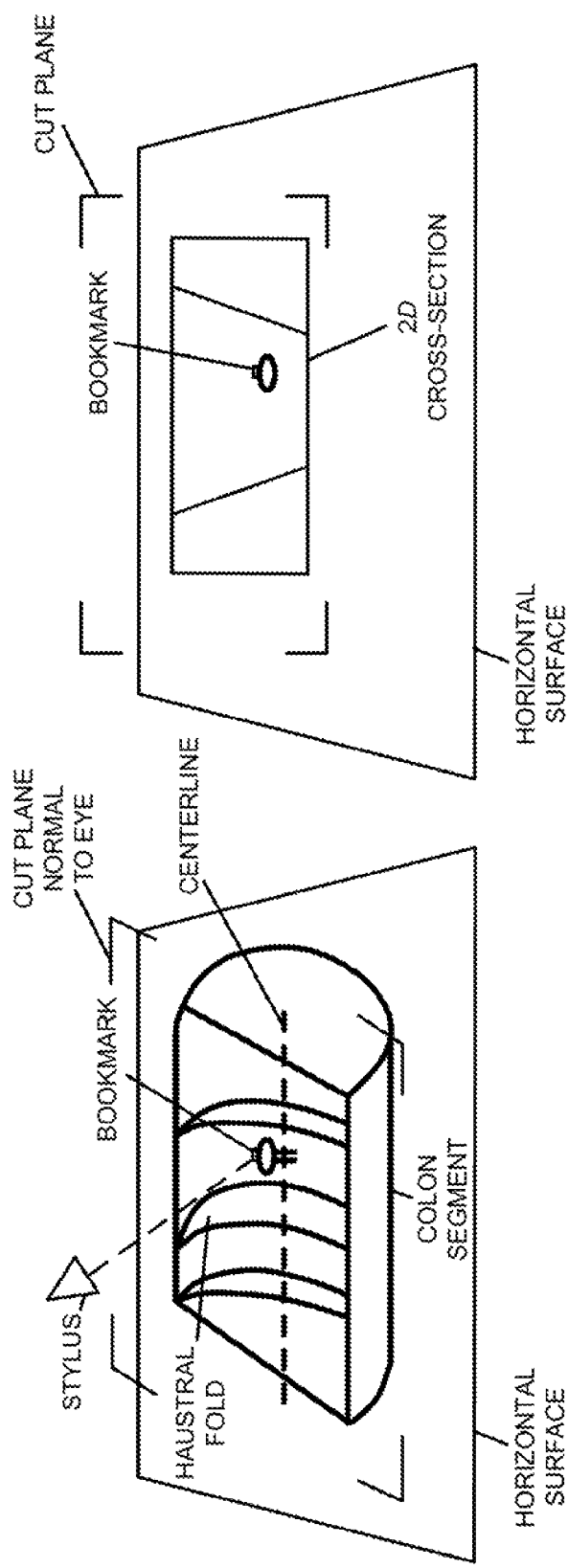
FIG. 29 is a drawing illustrating problem solving during a CTC in accordance with an embodiment of the present disclosure.

The translation and rotation operations are shown in FIG. 29, which presents a drawing illustrating, problem solving during a CTC. In particular, the normal vector of a 2D plane in a 3D image may be rotated and translated so that it is perpendicular to the plane of FIG. 29 (which represents a reference 2D plane of a display that displays the 3D image). This perpendicular orientation may facilitate determining or specifying a measurement associated with a colon structure. This normal vector may be the local normal of the polyp candidates. Moreover, the right or left vector of the colon segment may be used to determine the up vector.

Figure 30:
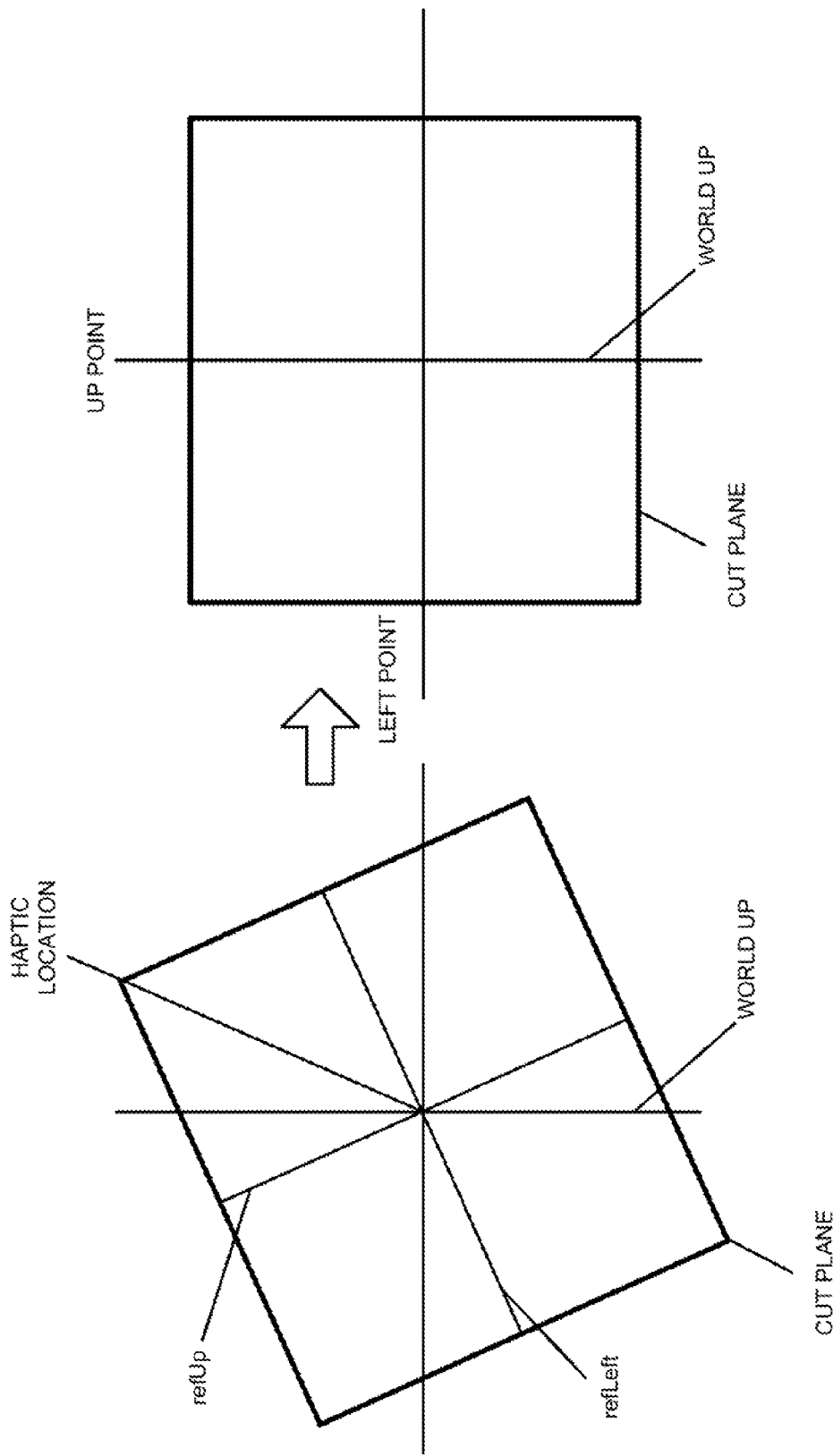
FIG. 30 is a drawing illustrating cut-plane preprocessing in accordance with an embodiment of the present disclosure.

The 2D-plane preprocessing may sometimes he used if the 2D plane used to review data is not aligned with the screen surface reference plane. The 2D-plane preprocessing is shown in FIG. 30, which presents a drawing of illustrating cut-plane preprocessing. During the 2D-plane-preprocessing, a vector that has zero x component, but that still lies in the 2D plane, may be determined. This calculation may use two vectors refUp and refLeft, and may determine a third vector (the desiredVector) for which the determinant is zero (i.e., so that the three vectors lie on the 2D plane). This problem-solving methodology may use: the 2D plane (which is sometimes referred to as a 'clip plane' or a 'cut plane') that may be applied to an object (which, for purposes of illustration, can be a volume or an image dataset used to create a 2D multiplanar-reconstruction-image slice or volume), the reference 2D plane (which is sometimes referred to as a 'physical plane') of the display, and the object. Note that the 2D plane may be defined using a point and a normal, where the point indicates the location of the 2D plane and the normal indicates the orientation of the 2D plane. Similarly, the reference 2D plane may be defined using a point and normal, where the point is the world center or origin (0, 0, 0) and the normal creates a rotation about the x axis (such as a −30° rotation).

Figure 31:
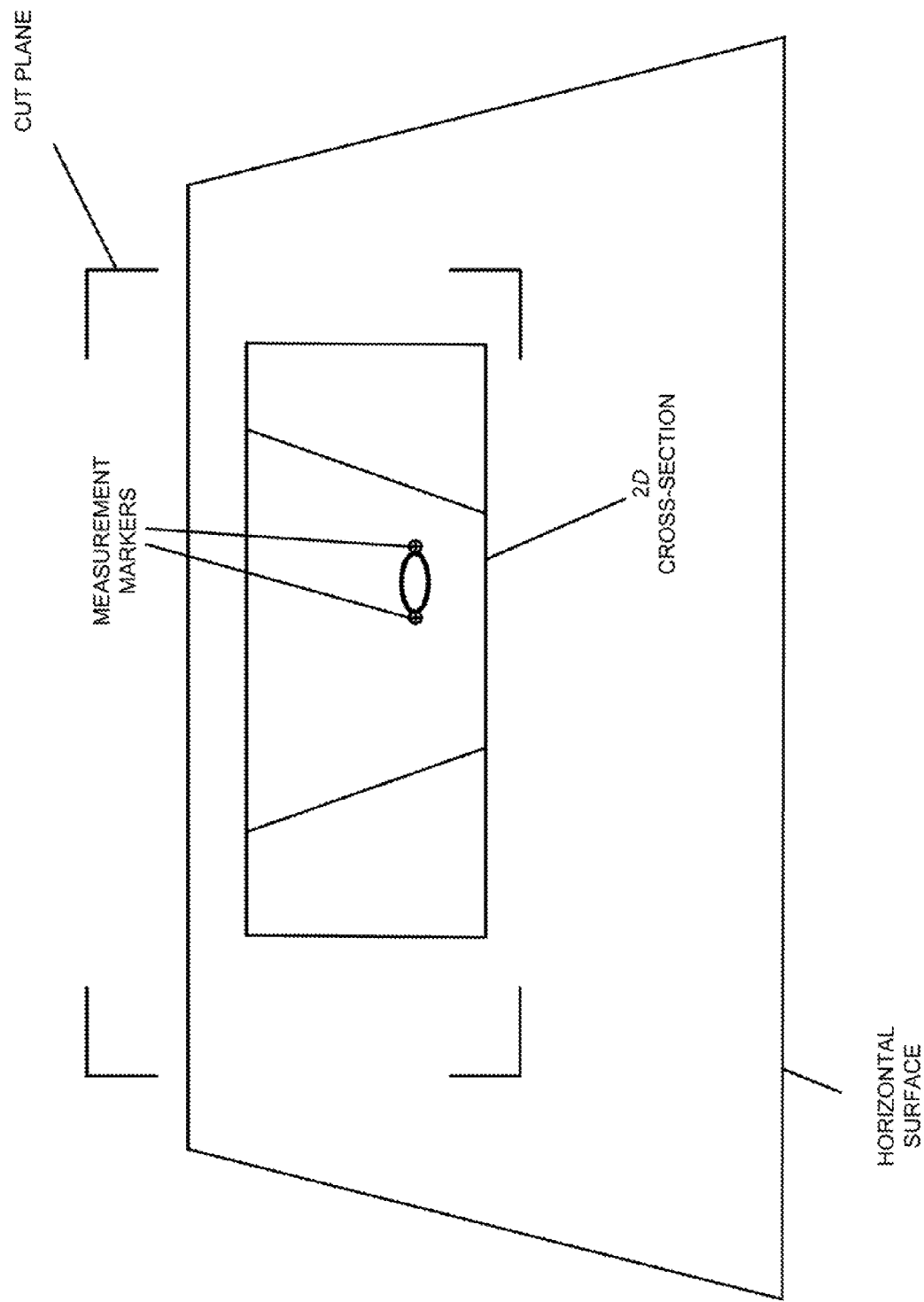
FIG. 31 is a drawing illustrating measurement of a potential polyp in accordance with an embodiment of the present disclosure.

The purpose of this technique may be to transform (which, in general, involves translation and/or rotation) an oblique cross-section of a volume or an oblique 2D MPR image (created by the application of the clip plane on the image data) to the reference 2D plane. Then, once on the reference 2D plane the cross-section or 2D MPR image may maintain an orientation so that the 'up' direction of the image data corresponds to the 'up' direction of the reference 2D plane. Moreover, because the cross-section of the volume or 2D MPR image is on the reference 2D plane, the user can rest his hand and may annotate (mark, measure, delineate, etc.) a 3D representation of the data with high confidence. This is illustrated in FIG. 31, which presents a drawing illustrating measurement of a potential polyp.

Figure 32:
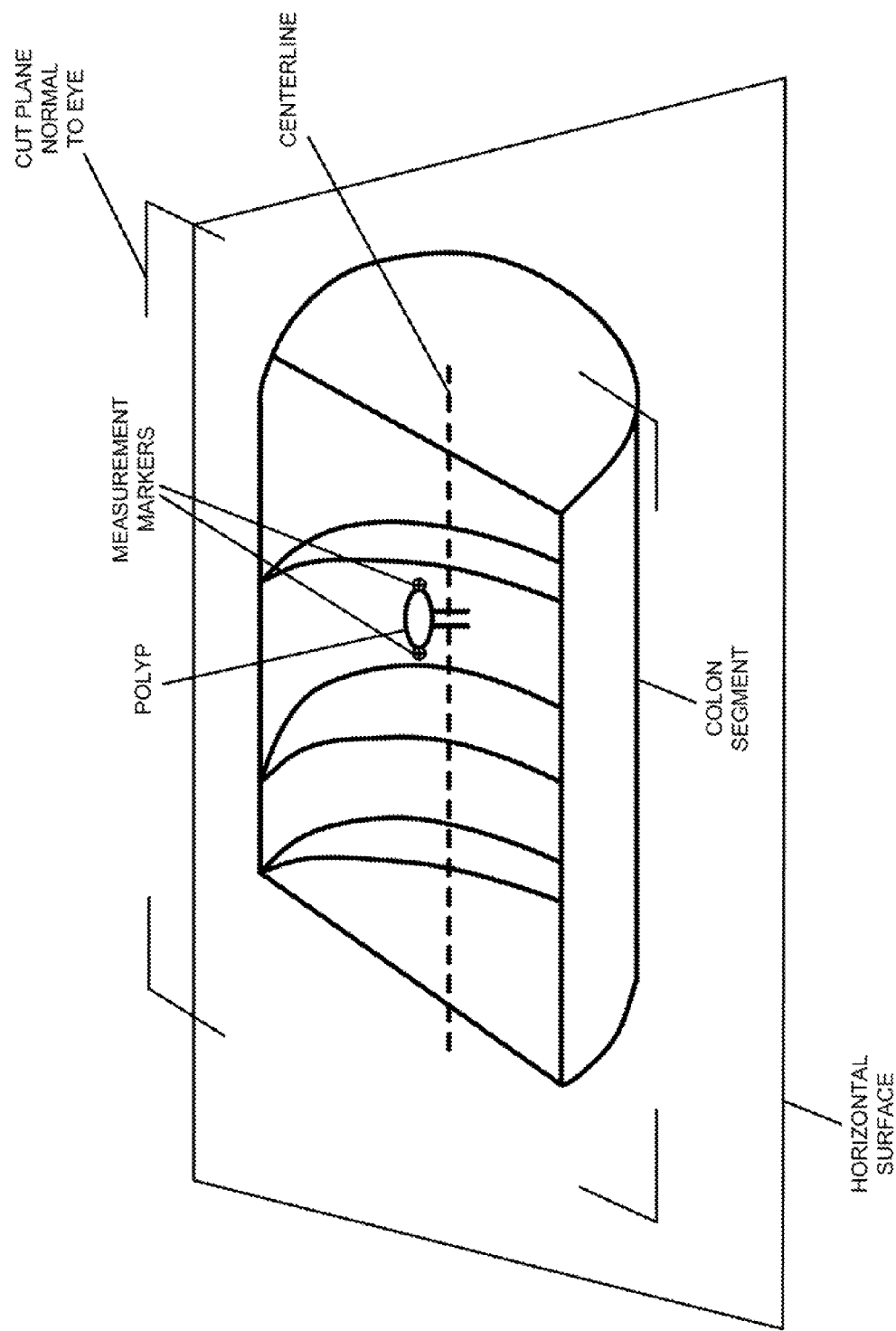
FIG. 32 is a drawing illustrating measurement of a potential polyp in accordance with an embodiment of the present disclosure.

Moreover, once the annotation is complete, the cross-section of the volume or the oblique 2D MPR image may be transformed (which, in general, involves translation and/or rotation) back to the original position. This is illustrated in FIG. 32, which presents a drawing illustrating measurement of a potential polyp. Note that the transformation may involve: start up, haptic-location identification, 2D plane preprocessing, haptic-rotation calculation, haptic-translation calculation, and/or application of the haptic transformation (including the haptic rotation and/or the haptic translation) about the haptic location to the object. The result of these operations may be that the cross-section of the object is visible on the reference 2D plane of the display.

During the start-up operation, the original matrices for both the 2D plane and the object may be saved (such as in a data structure in a computer-readable memory). These matrices may contain the location, orientation and scale. Similarly, during the haptic.-location-identification operation, the original location of the 2D plane (which is sometimes referred to as a haptic location') may be saved to be used as a point from which to apply the haptic rotation. Moreover, during the 2D-plane-preprocessing operation, the 2D plane may be rotated in place so that it is pointing up (which is sometimes referred to as a 'world up'), thereby removing any additional rotation except for the −30' rotation that may be required for the physical display (i.e., to the reference 2D plane).

Furthermore, during the haptic-rotation-calculation operation, the rotation of the 2D plane to the reference 2D plane may be calculated (in this example, this may be a −30° rotation about the x axis) and the resulting rotation matrix, used for this transformation (which is sometimes referred to as a 'haptic-rotation') may be saved. Additionally, during the haptic-translation-calculation operation, the translation needed to move the 2D plane to the reference 2D plane may be determined. The delta vector in this operation (which is sometimes referred to as a 'haptic translation') may be saved. Finally, during the haptic-transformation operation, the haptic rotation may be applied to the object about the haptic location (the original position of the 2D plane), and then the haptic translation may be applied to the object (e.g., it may be translated by the same amount as the 2D plane).

We now describe embodiments of the 2D-plane preprocessing in more detail. Referring back to FIG. 30, during the 2D-plane-preprocessing operation, a vector that has zero x component, but that still lies in the 2D plane, may be determined. As noted previously, this calculation may use two vectors refUp and refLeft, and may determine a third vector (the desired Vector) for which the determinant is zero (i.e., so that the three vectors lie on the 2D plane). In particular, the current refUp and refLeft points may be identified. Then, the haptic point (location) may be identified. Moreover, the up Vector may be calculated as refUp minus the haptic point, and the leftVector may be calculated as refLeft minus the haptic point.

Next, the upVector and leftVector may be normalized. Furthermore, the z component of desired Vector may be calculated via, evaluation of different possibleVectors. The components of possibleVector1 may be $$possibleVector1[x] \quad 0$$
$$possibleVector1[y] \quad \sqrt{1 - possibleVector1[z]^2}$$
$$possibleVector1[z] \quad \frac{(leftVector_x \cdot upVector_z - upVector_z \cdot leftVector_z)}{\sqrt{\alpha \cdot \beta + \delta^2}},$$

where $\alpha = leftVector_x \cdot upVector_y - upVector_z \cdot leftVector_y$, $\beta = leftVector_x \cdot upVector_y - upVector_x \cdot leftVector_y$, and $\delta = leftVector_x \cdot upVector_z - upVector_x \cdot leftVector_z$.

Similarly, the components of possibleVector2 may be $$possibleVector2[x] \quad 0$$
$$possibleVector2[y] \quad \sqrt{1 - possibleVector2[z]^2}$$
$$possibleVector2[z] \quad \frac{-(leftVector_x \cdot upVector_z - upVector_z \cdot leftVector_z)}{\sqrt{\alpha \cdot \beta + \delta^2}},$$

where $\alpha = leftVector_x \cdot upVector_y - upVector_z \cdot leftVector_y$, $\beta = leftVector_x \cdot upVector_y - upVector_x \cdot leftVector_y$, and $\delta = leftVector_x \cdot upVector_z - upVector_x \cdot leftVector_z$.

Subsequently, the 3×3 determinates of the possible vectors may be calculated as $$det1 = \begin{vmatrix} upVector_x & upVector_y & upVector_z \\ leftVector_x & leftVector_y & leftVector_z \\ possibleVector1[x] & possibleVector1[y] & possibleVector1[z] \end{vmatrix}$$

and $$det2 = \begin{vmatrix} upVector_x & upVector_y & upVector_z \\ leftVector_x & leftVector_y & leftVector_z \\ possibleVector2[x] & possibleVector2[y] & possibleVector2[z] \end{vmatrix}.$$

The desiredVector may be the possible vector with the smallest z component. In particular, if det1 is less than det2, the desired Vector may equal possibleVector1. Otherwise, if det2 is less than det1, the desiredVector may equal possible Vector2. As described further below, the quaternion rotation from the upVector to the desiredVector may then be calculated, where $V_0$ equals the upVector and V1 equals the desired Vector.

Note that the delta vector may be the difference between two quaternion rotations defined by two reference markers and a feature. In particular, a quaternion $\vec{q}$ may be an array containing a vector $\vec{v}$ and a scalar w. The scalar value may be the rotation angle θ in radians and the vector may be the unit vector about which the rotation takes place. Thus, $$\vec{q}\langle \vec{v}, w \rangle,$$

where w equals q3 and $$\vec{v} = [q_0, q_1, q_2] = [x, y, z].$$

Moreover, a quaternion can represent a rotation by a rotation angle θ around a unit axis a. Note that if a has unit length, then $\vec{q}$ has unit length too. Therefore.

$$\vec{q} = \left[ a_x \sin\left(\frac{\theta}{2}\right) a_y \sin\left(\frac{\theta}{2}\right) a_z \sin\left(\frac{\theta}{2}\right), \cos\left(\frac{\theta}{2}\right) \right]$$

or $$\vec{q} = \left[ \vec{a} \sin\left(\frac{\theta}{2}\right), \cos\left(\frac{\theta}{2}\right) \right].$$

We now describe embodiments of the quaternion calculation in more detail. Given normalized vectors $V_0$ and $V_1$, $\vec{q}$ equals $$V_0 V_1^* = [V_0 x V_1, V_0 \cdot V_1] = \left[ \hat{V} \sin\left(\frac{\theta}{2}\right), \cos\left(\frac{\theta}{2}\right) \right],$$

where $$\hat{V} = \frac{V_0 x V_1}{\|V_0 x V_1\|},$$

$$V_0 \cdot V_1 = \cos\left(\frac{\theta}{2}\right) = W,$$

and $$\vec{q}^* = [-V, W].$$

In an exemplary embodiment,

2·φ=upVector−desiredVector, qv=upVector$\hat{\times}$desiredVector, where $\hat{\times}$ denotes a cross product, $$2 \cdot \varphi = a\cos(2 \cdot \phi),$$

and $$\phi = \frac{2 \cdot \varphi}{2}.$$

Then, the quaternion rotation scalar w may be cos(φ) and the projection factor f for a unit vector of the quaternion may be sin(φ). Consequently, the components of the quaternion may be
  q[0] w
  q[1] f·qv[0]
  q[2] f·qv[1]
  q[3] f·qv[2]
Therefore, the quaternion may be transformed into a 3×3 rotation matrix.

Figure 33:
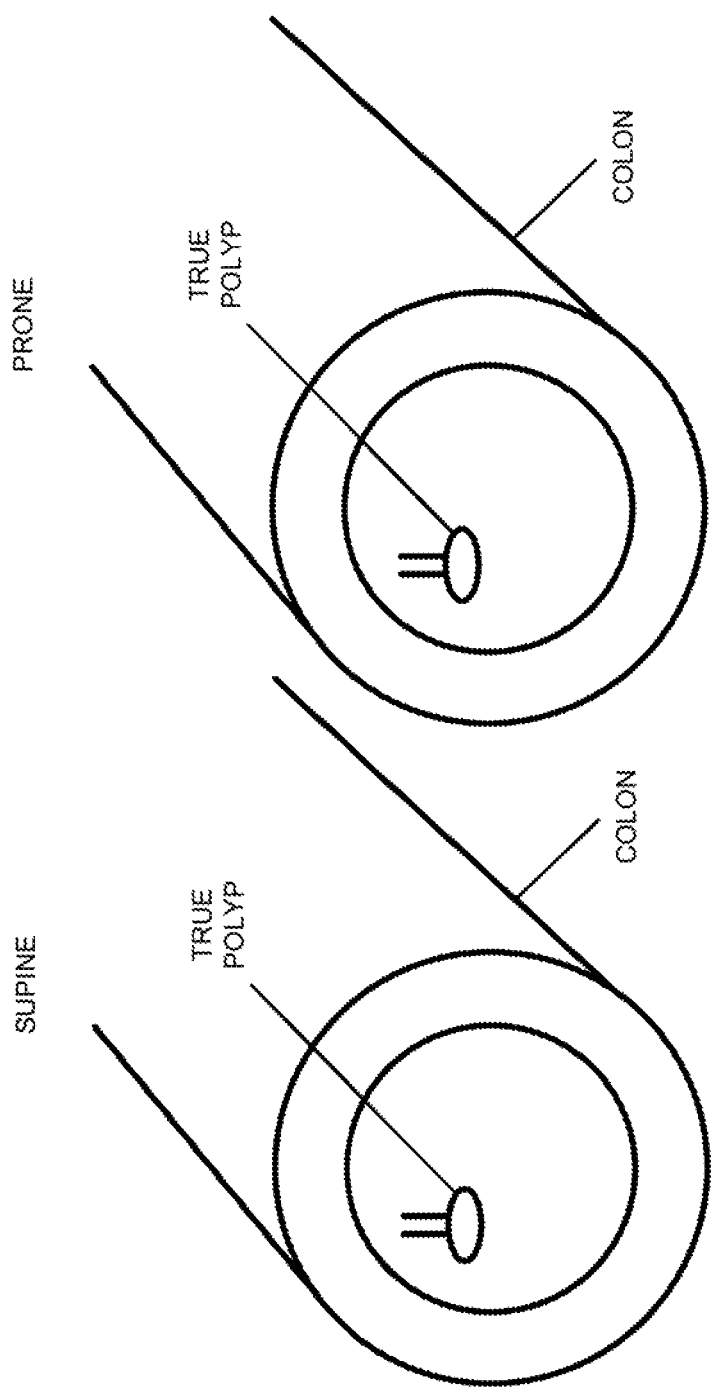
FIG. 33 is a drawing, illustrating dual views of a true polyp in accordance with an embodiment of the present disclosure.
Figure 34:
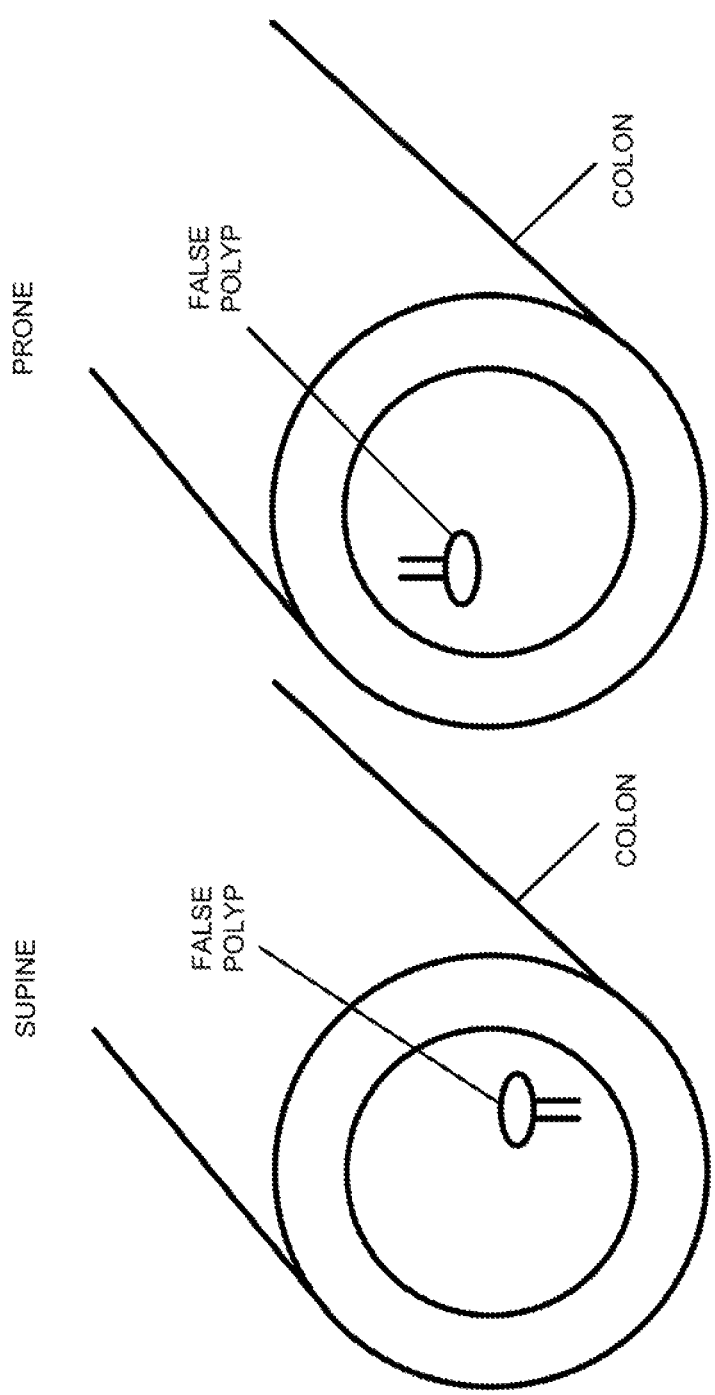
FIG. 34 is a drawing illustrating dual views of a false polyp in accordance with an embodiment of the present disclosure.
Figure 35:
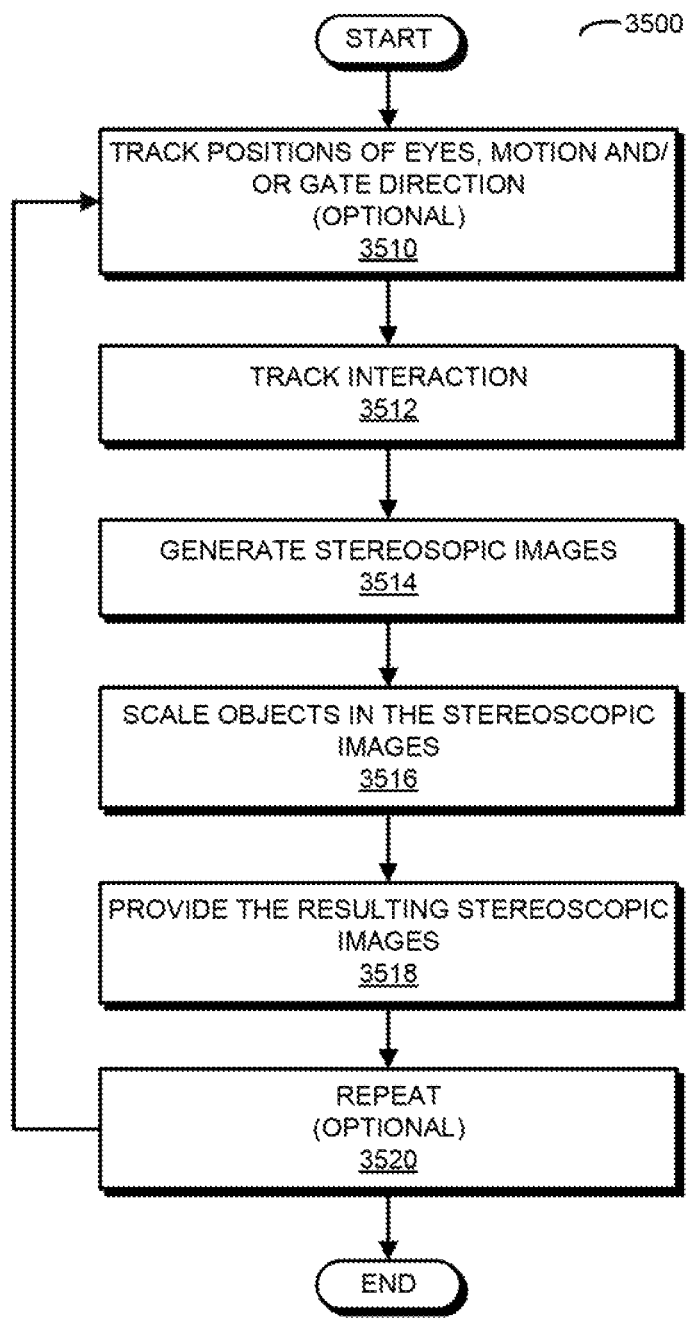
FIG. 35 is a flow diagram illustrating a method for providing stereoscopic images in accordance with an embodiment of the present disclosure.

Note that the purpose of the dual-view methodology may be to assess candidate polyp motility. When the dual-view methodology is engaged, the reader may see both the supine and prone colon surface model segments, each with its individual cut plane and their corresponding bookmarks and measurements. This is shown in FIG. 33, which presents a drawing illustrating dual views of a true polyp. In contrast, as shown in FIG. 34, which presents a drawing illustrating dual views of a false polyp, using the dual-view methodology the reader may visualize lesion motion using correlate supine and prone views. Note that the bookmarks and measurements of a supine or prone view may be registered in the corresponding prone or supine view using a diff color.

Moreover, the purpose of the image-review methodology may be to display the tillage data as spatially registered 2D MPR images. When the image-review methodology is engaged, the reader may control the cat plane by interacting with the center point, and may translate and rotate the cut plane using an optional interaction tool. For example, the reader may control as cut plane to uncover underlying anatomical features, thereby allowing the rest of the anatomical segment to be brought into view by rotating the anatomical segment. Note that the cut plane may modify the bounding-box coordinates of the anatomical segment by identifying the intersection points of the cut plane to the bounding box in the direction of the normal of the cut plane. The reader may also focus on polyp candidates using a region-of-interest magnification. Moreover, the reader can display 2D images with axial, coronal, sagittal and MPR, as well as 3D views (including volume rendered images).

True 3D-CTC may provide improved anatomic understanding. Current CTC visualization techniques typically have limitations in representing the complicated 3D relationships present in the colon, which facilitate polyp detection. In order to successfully identify a polyp, radiologists usually must integrate a series of 2D images in their mind and cognitively extract the relevant 3D relationships that define the colon, neighboring anatomy and polyps. In complicated cases, they may have to visually map two or more views of the same data to find appropriate correspondences of one view with another view to produce a match and determine if what they see is a true polyp. Instead, these operations can be provided by the graphical system.

Furthermore, True 3D-CTC can enable immediate colon-lumen identification as open tissue segments with no distortion, and which maintain true or accurate 3D relationships. In particular, True 3D-CTC may provide a better understanding of anatomical shapes because it integrates all three dimensions and corresponding depth cues in a single view.

True 3D-CTC may also provide increased polyp sensitivity. Reader perceptual error is a reason for false-negatives. Ideally, polyps are visible as abnormal structures that protrude the colon wall. However, when polyps are less conspicuous, radiologists typically report that: polyps appear flat; polyp edges are not prominent (e.g., not well defined); polyps are difficult to distinguish from a normal fold; polyps look like noise or a normal bump on the colonic surface; and/or the polyp looks like stool. Studies have determined that polyp height is a major determinant of visual conspicuity.

Viewing polyp images with True 3D-CTC may provide an improved visualization and detection tool than analyzing monoscopic 3D-rendered images, because the visual features that define a polyp (such as its shape, size, height and edges) can be magnified as as function of image perspective and parallax. In particular, strong parallax can enhance the visual elevation of polyps (such as the polyp height) and the visual prominence of edges in colon structures, and can improve the contextual features of colon folds. For example, these capabilities may allow detection of small-size polyps (such as those measuring 6-9 mm), which current CTC technology may detect with suboptimal sensitivity and specificity.

True 3D-CTC can be used to reduce interpretation time. The colon-segment navigation technique described above can eliminate anterograde and retrograde endoluminal navigation, thereby decreasing interpretation times and reducing reader tracking of the colon when there are redundant segments, aberrant anatomy, or if collapsed segments are present. The colon-segment navigation technique also has the potential to simplify reader decisions by displaying undistorted colon segments that preemptively remind readers of particular colon-segment normal and abnormal anatomy.

Additionally, True 3D-CTC may increase reader tolerance to image noise. Low-dose CTC imaging techniques are now standard of care. However, overall image quality is reduced as the radiation dose decreases (e.g., there is reduced soft-tissue contrast and higher image noise). In particular, in 3D endoluminal images, artifacts like mucosal nodulatity and endoluminal floaters can become more prominent. While techniques such as adaptive statistical iterative reconstruction (ASIR) can significantly reduce noise in low-dose images, imaging artifacts can persist in 3D reconstructions. Viewing low-dose polyp images with True 3D-CTC may offer improved performance, because it enables readers to see through clutter in the foreground or background, and makes it possible to focus at different depth levels, potentially increasing the reader's tolerance to image noise in low-dose CTC.

Combining True 3D-CTC with CAD can improve true-positive and false-positive discrimination. In general, conventional CTC combined with CAD is associated with high false-positive rates, leaving readers the hard task of visually mapping 2D and 3D views to discriminate true from false-positives. True 3D-CTC plus CAD can reduce true-positive and false-positive discrimination times because the problem-solving virtual instrument can enable the assessment of lesion tissue-density homogeneity with polyp morphologic features in a combined 2D and 3D view.

Finally, controlling CAD polyp candidates and any bookmarked polyp candidates with a hand-directed stylus offloads spatial cognition onto the reader's perceptual motor system, instead of performing a mental rotation or an imagined perspective shift, thereby reducing the cognitive intensity of CTC interpretation.

For these reasons, True 3D is expected to provide a significant improvement in CTC. This was borne out in preliminary pilot benchmark testing. In particular, using a public CTC dataset. True 3D increased the detection rate for a flat lesion greater than 6 mm by 20% Such improvements in CTC accuracy may be important factor for patient screening compliance and cost-effectiveness, as well as a key contributor of patients' preference of CTC over ordinary colonoscopy.

Methods

FIG. 28 presents a flow diagram illustrating a method 2800 for providing stereoscopic images, which may be performed by graphical system 100 (FIG. 1) and, more generally, a computer system. During operation, the computer system generates the stereoscopic images (operation 2814) at a location corresponding to a viewing plane based on data having a discrete spatial resolution, where the stereoscopic images include image parallax. Then, the computer system scales objects in the stereoscopic images (operation 2816) so that depth acuity associated with the image parallax is increased, where the scaling (or stereopsis sealing is based on the spatial resolution and a viewing geometry associated with a display. For example, the objects may be scaled prior to the start of rendering. Next, the computer system provides the resulting stereoscopic images (operation 2818) to the display. For example, the computer system may render and provide the stereoscopic images.

Note that the spatial resolution may be associated with a voxel size in the data, along a direction between images in the data and/or any direction of discrete sampling.

Moreover, the viewing plane may correspond to the display. In some embodiments, the computer system optionally tracks positions of eyes (operation 2810) of an individual that views the stereoscopic images on the display. The stereoscopic images may be generated based on the tracked positions of the eyes of the individual. Furthermore, the computer system may optionally track motion Operation 2810) of the individual, and may optionally re-generate the stereoscopic images based on the tracked motion of the individual (operation 2818) so that the stereoscopic images include motion parallax. Additionally, the computer system may optionally track interaction (operation 2812) of the individual with information in the displayed stereoscopic images, and may optionally re-generate the stereoscopic images based on the tracked interaction so that the stereoscopic images include prehension by optionally repeating (operation 2820) one or more operations in method 2800. For example, the individual may interact with the information using one or more interaction tools. Thus, when generating the stereoscopic images (operation 2814) or preparing the stereoscopic images, information from optionally tracked motion (operation 2810) and/or the optionally tracked interaction may be used to generate or revise the view and projection matrices, Note that the stereoscopic images may include a first image to be viewed by a left eye of the individual and a second image to be viewed by a right eye of the individual. Moreover, the viewing geometry may include a distance from the display of the individual and/or a focal point of the individual.

In some embodiments, generating the stereoscopic images is based on: where the information in the stereoscopic images is located relative to the eyes of the individual that views the stereoscopic images on the display; and a first frustum for one of the eyes of the individual and a second frustum for another of the eyes of the individual that specify what the eyes of the individual observe when view the stereoscopic images on the display. Furthermore, generating the stereoscopic images may involve: adding monoscopic depth cues to the stereoscopic images; and rendering the stereoscopic images.

In some embodiments, the computer system optionally tracks a gaze direction (operation 2810) of the individual that views the stereoscopic images on the display. Moreover, an intensity of a given voxel in a given one of the stereoscopic images may be based on a transfer function that specifies a transparency of the given voxel and the gaze direction so that the stereoscopic images include foveated imaging.

Figure 36:
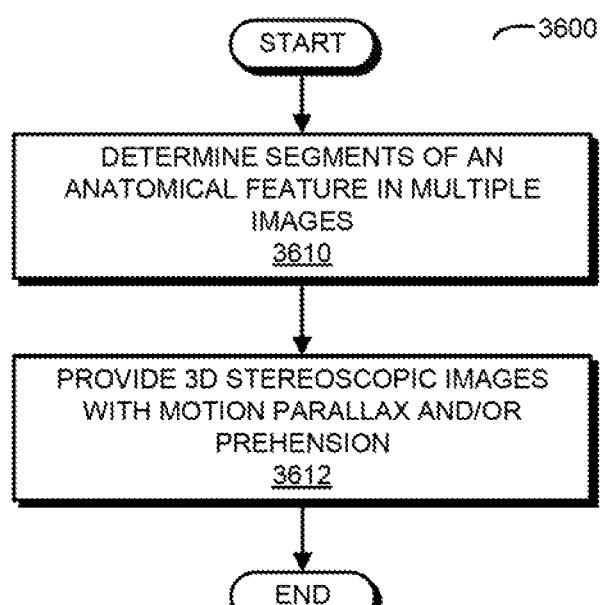
FIG. 36 is a flow diagram illustrating a method for determining segments of an anatomical feature in multiple images in accordance with an embodiment of the present disclosure.

FIG. 36 presents a flow diagram illustrating a method 3600 for determining segments of an anatomical feature in multiple images, which is sometimes referred to as 'segment navigation,' and which may be performed by graphical system 100 (FIG. 1) and, more generally, a computer system. During operation, the computer system determines segments of an anatomical feature in multiple images (operation 3610). These segments may describe the anatomical feature using the articulated model. Furthermore, the segments may have aspect ratios less than a pre-determined value. Using the segments, the computer system may provide 3D stereoscopic images with motion parallax and/or prehension (operation 3512). For example, the segments may facilitate: more compact storage of information corresponding to the anatomical feature, fast extraction of regions of interest by the computer system and faster rending of the 3D stereoscopic images by the computer system.

Figure 37:
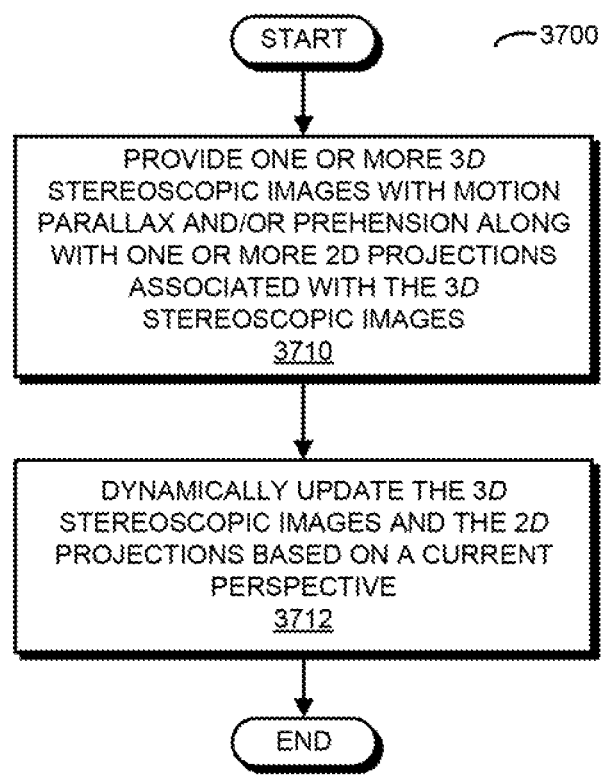
FIG. 37 is a flow diagram illustrating a method for providing 3D stereoscopic images and associated 2D projections in accordance with an embodiment of the present disclosure.

FIG. 37 presents a flow diagram illustrating a method 3700 for providing 3D stereoscopic images and associated 2D projections, which may be performed by graphical system 100 (FIG. 1) and, more generally, a computer system. During operation, the computer system provides one or more 3D stereoscopic images with motion parallax and/or prehension along with one or more 2D projections (or cross-sectional views) associated with the 3D stereoscopic images (operation 3710). The 3D stereoscopic images and the 2D projections may be displayed side by side on a common display. Moreover, as the user interacts with the 3D stereoscopic images and/or the one or more 2D projections and changes their viewing perspective, the computer system may dynamically update the 3D stereoscopic images and the 2D projections based on the current perspective (operation 3712). In some embodiments, note that the 2D projections are always presented along a perspective direction perpendicular to the user so that motion parallax is registered in the 2D projections.

Figure 38:
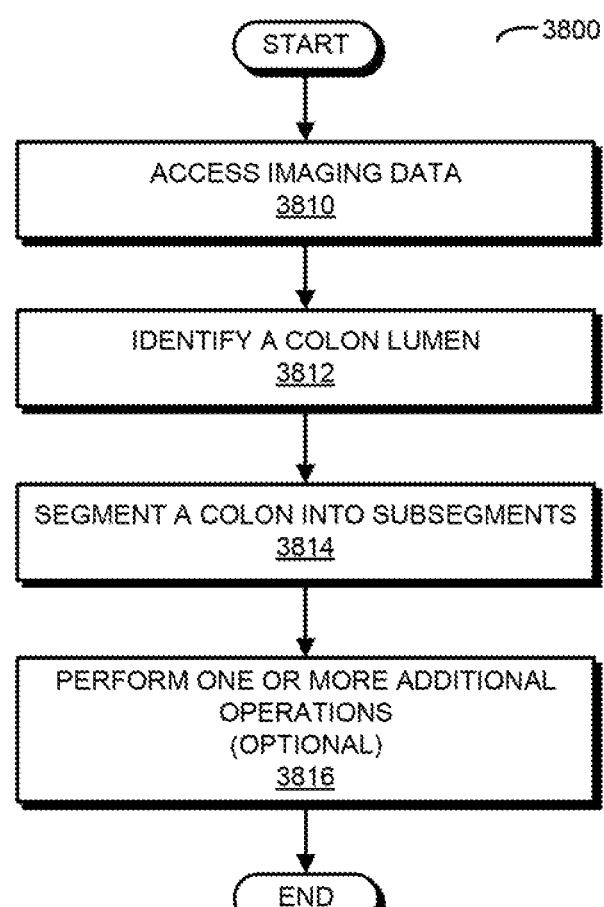
FIG. 38 is a flow diagram illustrating a method for segmenting a colon for a CTC in accordance with an embodiment of the present disclosure.

FIG. 38 presents a flow diagram illustrating a method 3800 for segmenting a colon for as CTC, which may be performed by graphical system 100 (FIG. 1) and, more generally, a computer system. During operation, the computer system accesses imaging data (operation 3810) having a spatial resolution. Then, the computer system identifies a colon lumen (operation 3812) based on probabilities for different tissue classes in the imaging data. Moreover, the computer system segments the colon into subsegments (operation 3814) based on an articulated object model that fits a tortuosity of the colon along a centerline of the colon, where the object model includes values, along the centerline, of one of: a basis set, curvature and torsion, and a local curvature scale, and where boundaries between subsegments are based on one of the curvature and the torsion; and the local curvature scale.

In some embodiments, the computer system optionally performs one or more additional operations (operation 3816). In particular, the computer system may receive navigation information specifying user navigation through the colon, and may receive position information specifying a position and an orientation of a head of a user. Then, the computer system may provide stereoscopic-acuity-scaled images of the subsegments of the colon with a cut plane across the colon at a pre-specified distance from the centerline based on the navigation information and the position information, where the pre-specified distance reduces an amount of rotation of a given subsegment needed to display the colon lumen. Moreover, the computer system rotates one or more of the subsegments of the colon to bring into view a clipped area of the colon lumen. Next, the computer system may receive a bookmark from the user of a region in the colon that includes a potential polyp. Furthermore, the computer system may provide a two-dimensional image of the colon along a normal direction to the bookmark, and may receive cross-sectional measurements of the potential polyp.

Figure 39:
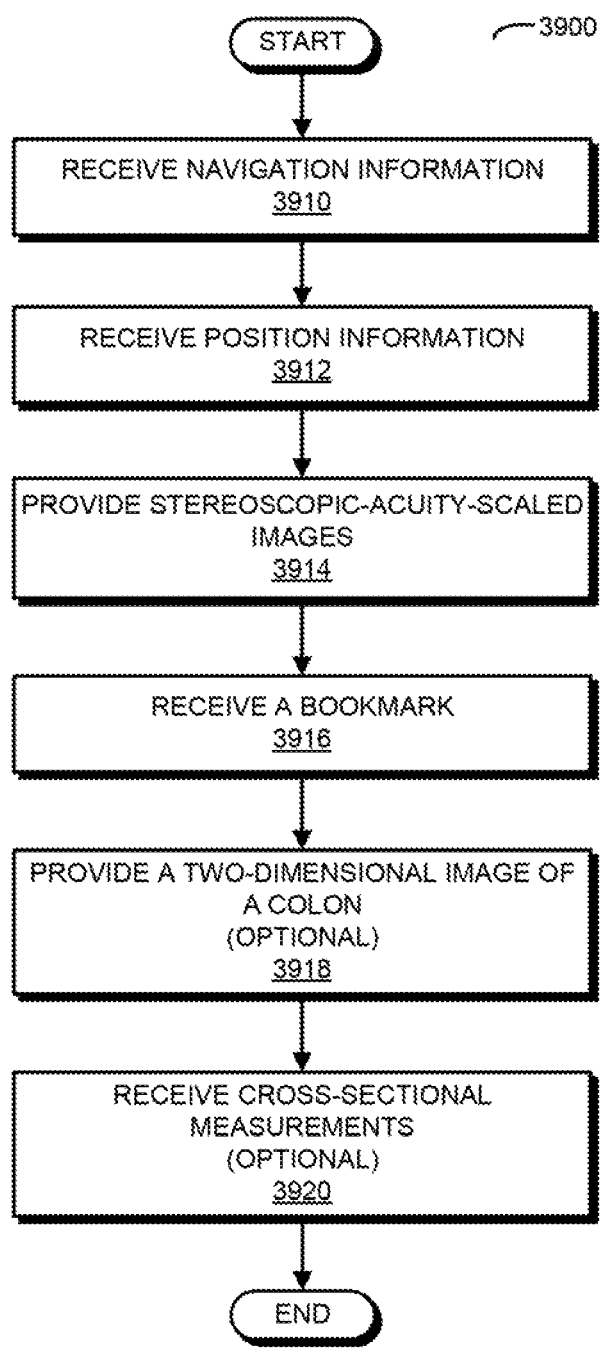
FIG. 39 is a flow diagram illustrating a method for navigating a colon in a CTC in accordance with an embodiment of the present disclosure.

FIG. 39 presents a flow diagram illustrating a method 3900 for navigating a colon in a CTC, which may be performed by graphical system 100 (FIG. 1) and more generally, a computer system. During operation, the computer system receives navigation information (operation 3940) specifying user navigation through the colon, and receives position information (operation 3912) specifying a position and an orientation of a head of a user. Then, the computer system provides stereoscopic-acuity-scaled images (operation 3914) of subsegments of the colon with a cut plane across the colon at a pre-specified distance from a centerline of the colon based on the navigation information and the position information. Next, the computer system receives a bookmark (operation 3916) from the user of a region in the colon that includes a potential polyp.

Moreover, the computer system may optionally provide a two-dimensional image of the colon (operation 3918) along a normal direction to the bookmark, and may optionally receive cross-sectional measurements (operation 3920) of the potential polyp.

In some embodiments of methods 2800, 3600, 3700, 3800 and/or 3900 there may be additional or fewer operations. Moreover, the order of the operations may be changed, and/or two or more operations may be combined into a single operation.

In the preceding description, we refer to 'some embodiments.' Note that 'some embodiments' describes a subset of all of the possible embodiments, but does not always specify the same subset of embodiments.

The foregoing description is intended to enable any person skilled m the art to make and use the disclosure, and is provided m the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to he accorded the widest scope consistent with the principles and features disclosed herein.

What is claimed is:

1. A method for segmenting a colon for a computed tomography colonography (CTC), wherein the method comprises:
   by a computer system:
   accessing imaging data having a spatial resolution;
   identifying a colon lumen based on probabilities for different tissue classes in the imaging data;
   determining boundaries between subsegments along a length of the colon based on one of: curvature and torsion of the colon; and a local curvature scale of the colon; and
   segmenting the colon into subsegments based on the boundaries and an object model that fits a tortuosity of the colon along a centerline of the colon, wherein the object model includes values, along the centerline, of one of: a basis set, the curvature and the torsion, and the local curvature scale.

2. The method of claim 1, wherein the tissue classes include: air, liquid and a boundary between air and liquid.

3. The method of claim 1, wherein identifying the colon lumen involves identifying a contrast liquid residing in the colon lumen and aggregating the contrast liquid into a volume mask using a digital subtraction bowel cleaning technique.

4. The method of claim 1, wherein the determining is performed iteratively.

5. The method of claim 1, wherein the subsegments include at least portions of: a rectum, a sigmoid, a descending colon, a transverse colon, an ascending colon and a cecum.

6. The method of claim 1, wherein the method further comprises:
receiving navigation information specifying user navigation through the colon;
receiving position information specifying a position and an orientation of a head of a user;
providing stereoscopic-acuity-scaled images of the subsegments of the colon with a cut plane across the colon at a pre-specified distance from the centerline based on the navigation information and the position information, wherein the pre-specified distance reduces an amount of rotation of a given subsegment needed to display the colon lumen;
rotating one or more of the subsegments of the colon to bring into view a clipped area of the colon lumen; and
receiving a bookmark from the user of a region in the colon that includes a potential polyp.

7. The method of claim 6, wherein the method further comprises:
providing a two-dimensional image of the colon along a normal direction to the bookmark; and
receiving cross-sectional measurements of the potential polyp.

8. The method of claim 1, wherein a given boundary between a pair of subsegments corresponds to local extremum values, over a length of the colon, of one of: the curvature and the torsion, and the local curvature scale.

9. The method of claim 8, wherein the local extremum values include one of: a minimum value of the curvature and a maximum value of the torsion; and local minimum and local maximum values of the local curvature scale.

10. The method of claim 1, wherein the subsegments are longer than a predefined first length and less than a predefined second length.

11. The method of claim 1, wherein there is overlap between the subsegments.

12. The method of claim 1, wherein maximum values, over a length of a given subsegment, of one of the curvature and the torsion, and the local curvature scale are less than predefined values so that the centerline of the given subsegment is approximately linear.

13. A non-transitory computer-readable storage medium for use in conjunction with a computer system, the computer-readable storage medium storing a program module, wherein, when executed by the computer system, the program module causes the computer system to segment a colon for a computed tomography colonography (CTC), by performing one or more operations comprising:
accessing imaging data having a spatial resolution;
identifying a colon lumen based on probabilities for different tissue classes in the imaging data;
determining boundaries between subsegments along a length of the colon based on one of: curvature and torsion of the colon; and a local curvature scale of the colon; and
segmenting the colon into subsegments based on the boundaries and an articulated object model that fits a tortuosity of the colon along a centerline of the colon, wherein the object model includes values, along the centerline, of one of: a basis set, the curvature and the torsion, and the local curvature scale.

14. The computer-readable storage medium of claim 13, wherein the tissue classes include: air, liquid and a boundary between air and liquid.

15. The computer-readable storage medium of claim 13, wherein the instructions for identifying the colon lumen include instructions for identifying a contrast liquid residing in the colon lumen and aggregating the contrast liquid into a volume mask using a digital subtraction bowel cleaning technique.

16. The computer-readable storage medium of claim 13, wherein the determining is performed iteratively.

17. The computer-readable storage medium of claim 13, wherein the one or more operations comprise:
receiving navigation information specifying user navigation through the colon;
receiving position information specifying a position and an orientation of a head of a user;
providing stereoscopic-acuity-scaled images of the subsegments of the colon with a cut plane across the colon at a pre-specified distance from the centerline based on the navigation information and the position information, wherein the pre-specified distance reduces an amount of rotation of a given subsegment needed to display the colon lumen;
rotating one or more of the subsegments of the colon to bring into view a clipped area of the colon lumen; and;
and
receiving a bookmark from the user of a region in the colon that includes a potential polyp.

18. The computer-readable storage medium of claim 17, wherein the one or more operations comprise:
providing a two-dimensional image of the colon along a normal direction to the bookmark; and
receiving cross-sectional measurements of the potential polyp.

19. The computer-readable storage medium of claim 13, wherein a given boundary between a pair of subsegments corresponds to local extremum values, over a length of the colon, of one of: the curvature and the torsion, and the local curvature scale; and
wherein the local extremum values include one of: a minimum value of the curvature and a maximum value of the torsion; and local minimum and local maximum values of the local curvature scale.

20. A computer system, comprising:
a processor; and
memory, wherein the memory stores a program module, and wherein, when executed by the processor, the program module causes the computer system to segment a colon for a computed tomography colonography (CTC) by performing one or more operations comprising:
accessing imaging data having a spatial resolution;
identifying a colon lumen based on probabilities for different tissue classes in the imaging data;
determining boundaries between subsegments along a length of the colon based on one of: curvature and torsion of the colon; and a local curvature scale of the colon; and
segmenting the colon into subsegments based on the boundaries and an articulated object model that fits a tortuosity of the colon along a centerline of the colon, wherein the object model includes values, along the centerline, of one of: a basis set, the curvature and the torsion, and the local curvature scale.

* * * * *